United States Patent
Mosher et al.

(10) Patent No.: US 11,596,694 B2
(45) Date of Patent: Mar. 7, 2023

(54) COMPOSITIONS AND METHODS FOR PREDICTING RESPONSE TO NAPI2B-TARGETED THERAPY

(71) Applicant: Mersana Therapeutics, Inc., Cambridge, MA (US)

(72) Inventors: Rebecca Mosher, Newton, MA (US); Laura L. Poling, Acton, MA (US); Donald A. Bergstrom, Winchester, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 403 days.

(21) Appl. No.: 16/136,706

(22) Filed: Sep. 20, 2018

(65) Prior Publication Data

US 2019/0160181 A1    May 30, 2019

Related U.S. Application Data

(60) Provisional application No. 62/718,692, filed on Aug. 14, 2018, provisional application No. 62/571,397, (Continued)

(51) Int. Cl.
*A61K 47/68*    (2017.01)
*C07K 16/28*    (2006.01)
(Continued)

(52) U.S. Cl.
CPC ...... *A61K 47/6803* (2017.08); *A61K 47/6849* (2017.08); *A61K 47/6857* (2017.08); *A61K 47/6869* (2017.08); *A61K 47/6889* (2017.08); *A61K 49/0004* (2013.01); *A61P 35/00* (2018.01); *C07K 16/28* (2013.01); *C07K 16/30* (2013.01); *G01N 33/574* (2013.01); *G01N 33/57423* (2013.01); *G01N 33/57449* (2013.01); *G01N 33/57492* (2013.01); *A61K 2039/505* (2013.01); *C07K 2317/24* (2013.01); (Continued)

(58) Field of Classification Search
None
See application file for complete search history.

(56) References Cited

U.S. PATENT DOCUMENTS 4,816,567 A  3/1989  Cabilly et al.
5,585,089 A  12/1996  Queen et al.
(Continued)

FOREIGN PATENT DOCUMENTS

EP  2 423 232 A1  2/2012
JP  2013-511993 A  4/2013
(Continued)

OTHER PUBLICATIONS

Soares et al., Applied Immunohistochemsitry and Molecular Morphology, vol. 20, No. 2, Mar. 1, 2012 (Mar. 1, 2012), pp. 165-172 (Year: 2012).*

(Continued)

*Primary Examiner* — Karl J Puttlitz
(74) *Attorney, Agent, or Firm* — Cooley LLP; Cynthia A. Kozakiewicz; Andrew Henderson

(57) ABSTRACT

This disclosure provides reagents and methods of predicting the responsiveness of a patient to NaPi2b-targeted antibody-drug conjugates (e.g., NaPi2b-targeted antibody-polymer-drug conjugates).

8 Claims, 22 Drawing Sheets

Specification includes a Sequence Listing.

Related U.S. Application Data filed on Oct. 12, 2017, provisional application No. 62/561,107, filed on Sep. 20, 2017.

(51) Int. Cl.

| | |
|---|---|
| *G01N 33/574* | (2006.01) |
| *C07K 16/30* | (2006.01) |
| *A61P 35/00* | (2006.01) |
| *A61K 49/00* | (2006.01) |
| *A61K 39/00* | (2006.01) |

(52) U.S. Cl.
CPC ...... *C07K 2317/94* (2013.01); *G01N 2800/52* (2013.01); *G01N 2800/56* (2013.01)

(56) References Cited

U.S. PATENT DOCUMENTS

| | | | |
|---|---|---|---|
| 5,614,367 A * | 3/1997 | Kaluza | G01N 33/54306 435/7.1 |
| 7,803,562 B2 | 9/2010 | Cannon et al. | |
| 8,383,799 B2 | 2/2013 | Guo et al. | |
| 8,535,675 B2 | 9/2013 | Dennis et al. | |
| 8,603,474 B2 | 12/2013 | Ritter et al. | |
| 8,703,714 B2 | 4/2014 | Doronina et al. | |
| 8,742,076 B2 | 6/2014 | Cohen et al. | |
| 8,802,094 B2 | 8/2014 | Cook et al. | |
| 8,809,359 B2 | 8/2014 | Lewis et al. | |
| 8,815,908 B2 | 8/2014 | Lewis et al. | |
| 8,815,910 B2 | 8/2014 | Lewis et al. | |
| 8,900,589 B2 | 12/2014 | Beria et al. | |
| 8,916,569 B2 | 12/2014 | Lewis et al. | |
| 9,045,533 B2 | 6/2015 | Ritter et al. | |
| 10,947,317 B2 | 3/2021 | Bergstrom et al. | |
| 2003/0039649 A1 | 2/2003 | Foote | |
| 2012/0321583 A1* | 12/2012 | Yurkovetskiy | A61K 47/6849 424/78.17 |
| 2015/0104407 A1 | 4/2015 | Yurkovetskiy et al. | |
| 2017/0266311 A1 | 9/2017 | Bergstrom et al. | |
| 2021/0301031 A1 | 9/2021 | Bergstrom et al. | |

FOREIGN PATENT DOCUMENTS

| | | |
|---|---|---|
| WO | WO 2003/060086 A2 | 7/2003 |
| WO | 2009097128 * | 8/2009 |
| WO | WO-2010122846 A1 | 10/2010 |
| WO | WO 2011/066503 A2 | 6/2011 |
| WO | WO 2012/171020 A1 | 12/2012 |
| WO | WO 2015/054669 A1 | 4/2015 |
| WO | WO-2016196792 A1 | 12/2016 |
| WO | WO 2017/068097 A1 | 4/2017 |
| WO | WO 2017/160753 | 9/2017 |
| WO | WO 2017/160754 | 9/2017 |
| WO | WO 2018/237262 A1 | 12/2018 |

OTHER PUBLICATIONS

Lin et al., Clin Cancer Res. Nov. 15, 2015;21(22):5139-50 (Year: 2015).*
"Chimeric Antibodies" at https://absoluteantibody.com/our-technology/formats-we-have-made/chimeric-antibodies/, downloaded Jul. 27, 2021 (Year: 2021).*
Tan et al., J Immunol 1985; 135:3564-3567 (Year: 1985).*
Bacus et al. "The Evaluation of Estrogen Receptor in Primary Breast Carcinoma by Computer-Assisted Image Analysis", Am J Clin Pathol, vol. 90, No. 3, p. 233-239, (1988).
Bowie et al., "A method to identify protein sequences that fold into a known three-dimensional structure", Science, vol. 253, p. 164-170 (1991).
Cerami et al. "The cBio Cancer Genomics Portal: An Open Platform for Exploring Multidimensional Cancer Genomics Data", Cancer Discovery, vol. 2, No. 5, p. 401-404 (2012).
Chotia et al. "Canonical Structures for the Hypervariable Regions of Immunoglobins", J MoI Biol, vol. 196, p. 901-917 (1987).
Chotia et al. "Conformations of immunoglobulin hypervariable regions", Nature, vol. 342, p. 878-883 (1989).
Chow et al., "Measurement of MAP Kinase Activation by Flow Cytometry Using Phospho-Specific Antibodies to MEK and ERK: Potential for Pharmacodynamic Monitoring of Signal Transduction Inhibitors", Cytometry (Communications in Clinical Cytometry), vol. 46, p. 72-78 (2001).
Cook, "Use and Misuse of the Receiver Operating Characteristic Curve in Risk Prediction," Circulation, vol. 115, p. 928-935 (2007).
Davies et al., "Antibody-Antigen Complexes", Annual Rev Biochem, vol. 59, p. 439-473 (1990).
Gao et al. "Integrative Analysis of Complex Cancer Genomics and Clinical Profiles Using the cBioPortal", Science Signaling, vol. 6, Issue 269, 20 pages, (2013).
Harvey et al. "Estrogen Receptor Status by Immunohistochemistry Is Superior to the Ligand-Binding Assay for Predicting Response to Adjuvant Endocrine Therapy in Breast Cancer", Ioumal of Clinical Oncology, vol. 17, p. 1474-1474, (1999).
Kabat et al. "Sequences of Proteins of Immunological Interest", 5th edit. NIH Publication No. 91-3242, U.S. Dept of Health & Human Services, iii-xcvi, p. 2130-2180, (1991).
Morrison "Success in Specification", Nature, vol. 368, No. 6474, p. 812-813, (1994).
Needleman et al. "A General Method Applicable to the Search for Similarities in the Amino Acid Sequence of Two Proteins", J. Mol. Biol. vol. 48, p. 443-453 (1970).
Malmqvist M. "Biosepcific interaction analysis using biosensor technology", Nature vol. 361, p. 186-187 (1993).
O'marcaigh A.S. et al. "Estimating The Predictive Value Of A Diagnostic Test, How To Prevent Misleading Or Confusing Results," Clinical Pediatrics vol. 32, No. 8, p. 485-491 (1993).
Pearson et al. "Improved tools for biological sequence comparison", Proc. Natl. Acad. Sci. USA, vol. 85, p. 2444-2448 (1988).
Shultz,"Clinical Interpretation Of Laboratory Procedures," chapter 14, in Teitz "Fundamentals of Clinical Chemistry", 4th edition, p. 192-199 (1996).
Smith et al. "Comparison of Biosequences", Advances in Applied Mathematics, vol. 2, p. 482-489 (1981).
Thornton et al. "Prediction of progress at last" Nature, vol. 354, p. 105 (1991).
Wilkerson et al. "Prediction of Lung Cancer Histological Types by RT-qPCR Gene Expression in FFPE Specimens", The Journal of Molecular Diagnostics, vol. 15, No. 4, p. 485-497 (2013).
Wilkinson D. "Ultimate Abs", The Scientist, vol. 14, No. 8 pp. 25-28 (2000).
Xu et al. "Molecular Cloning, Functional Characterization, Tissue Distribution, and Chromosomal Lozalization of a Human, Small Intenstinal Sodium-Phosphate (Na+ -$P_i$) Transporter (SLC34A2)", Genomics, vol. 62, p. 281-284 (1999).
Zweig et al., "ROC Curve Analysis: An Example Showing The Relationships Among Serum Lipid And Apolipoprotein Concentrations In Identifying Subjects With Coronary Artery Disease," Clin, Chem., vol. 38, No. 8, p. 1425-1428 (1992).
Bodyak N. et al. "Abstract 1194: Discovery and preclinical development of a highly potent NaPi2b-targeted antibody-drug conjugate (ADC) with significant activity in patient-derived non-small cell lung cancer (NSCLC) xenograft models", AACR 107th Annual Meeting 2016; Apr. 16-20, 2016; New Orleans, LA, vol. 76 (Suppl 14), 2016, 3 pages.
Gerber D.E. et al. "Safety, Pharmacokinetics, and Activity of the Anti-NaPi2b Antibody-Drug Conjugate DNIB0600A: A Phase I Study in Patients with Non-Small Cell Lung Cancer and Platinum-Resistant Ovarian Cancer", IASLC World Lung, 2013, 1 page.
Lin K. et al. " Preclinical Development of an Anti-NaPi2b (SLC34A2) Antibody-Drug Conjugate as a Therapeutic for Non-Small Cell Lung and Ovarian Cancers", Clinical Cancer Research, vol. 21, No. 22, 2015, pp. 5139-5150.
Mosher R. et al. "Abstract B119: Relationship of NaPi2b expression and efficacy of XMT-1536, a NaPi2b targeting antibody-drug conjugate (ADC), in an unselected panel of human primary ovarian

(56) References Cited

OTHER PUBLICATIONS mouse xenograft models", AACR-NCI-EORTC International Conference: Molecular Targets and Cancer Therapeutics, vol. 17(S1), 2018, 2 pages.

Soares, I. C. et al. "In Silico Analysis and Immunohistochemical Characterization of NaPi2b Protein Expression in Ovarian Carcinoma With Monoclonal Antibody Mx35" Applied Immunohistochemistry and Molecular Morphology, vol. 20, No. 2, 2012, p. 165-172.

Banerjee S. et al. "A Randomized, Open-Label, Phase II Study of Anti-NaPi2b Antibody-Drug Conjugate Lifastuzumab Vedotin (DNIB0600A) Compared to Pegylated Liposomal Doxorubicin in Patients with Platinum-Resistant Ovarian Cancer", ASCO Annual Meeting, Jun. 3-7, slide 5569, 1 page (2016).

Banerjee S., et al. "Anti-NaPi2b antibody-drug conjugate lifastuzumab vedotin (DN1B0600A) compared with pegylated liposomal doxorubicin in patients with platinum-resistant ovarian cancer in randomized, open-label, phase II study," Annals of Oncology, vol. 29, p. 917-923 (2018).

Bodyak, N. et al. "Discovery and preclinical development of a highly potent NaPi2b-targeted antibody-drug conjugate (ADC) with significant activity in patient-derived non-small cell lung cancer (NSCLC) xenograft models", Mersana Therapeutics (poster), 1 page (2016).

Bodyak et al. "The Dolaflexin-based antibody-drug conjugate XMT-1536 targets the solid tumor lineage antigen SLC34A2/NaPi2b, Mol Cancer Ther, American Association for Cancer Research", Author Manuscript Published OnlineFirst on Mar. 15, 2021, p. 1-27.

Burris, H. et al. "A phase I study of DNIB0600A, an antibody-drug conjugate (ADC) targeting NaPi2b, in patients (pts) with non-small cell lung cancer (NSCLC) or platinum-resistant ovarian cancer (OC)", J Clin Oncol 32, Abstract 2504, p. 1-4 (2014).

Carter et al. "Antibody-Drug Conjugates for Cancer Therapy", The Cancer Journal, vol. 14, No. 3, p. 154-169 (2008).

D' Arcangelo, M. et al. "Prevalence and prognostic significance of sodium-dependent phosphate transporter 2b (NaPi2b) protein expression in non-small cell lung cancer", Annals of Oncology, vol. 25, No. 4, 1 page (2014).

Degaki T.L., et al. "Generation of Humanized Rebmab 200," 9th PEAC Conference on Protein Expression in Animal Cells, Jackson Hole, Wyoming, USA, Sep. 19-23, 2009, p. 1-2.

Doronina et al. "Development of potent monoclonal antibody auristatin conjugates for cancer therapy", Nature Biotechnology, vol. 21, No. 7, 778-784 (2003).

Dos Santos et al. "Rebmab200, a Humanized Monoclonal Antibody Targeting the Sodium Phosphate Transporter NaPi2b Displays Strong Immune Mediated Cytotoxicity against Cancer: A Novel Reagent for Targeted Antibody Therapy of Cancer", PLOS One, vol. 8, No. 7, e70332, p. 1-10 (2013).

Dos Santos, M. L. et al. "Generation of a Stable Cell Line for Rebmab 200 MAB," 22nd ESACT Meeting Vienna, Austria, May 15-18, 2011, p. 1-2.

Dos Santos, M. L. et al. "Flow cytometry characteristics of Rebmab 200," 9th PEAC Conference, Jackson Hole, Wyoming, USA, Sep. 19-23, 2009, p. 1-2.

Dos Santos, M. L. et al., "Stability analysis of Humanized Rebmab 100 monoclonal antibody," 9th PEAC Conference, Jackson Hole, Wyoming, USA, Sep. 19-23, 2009, p. 1-2.

Eisenhauer E.A., et al. "New response evaluation criteria in solid tumors: Revised RECIST guideline (version 1.1)," European Journal of Cancer, vol. 45, p. 228-247 (2009).

Fisher et al., "Gene expression profiling of clear cell papillary renal cell carcinoma: comparison with clear cell renal cell carcinoma and papillary renal cell carcinoma", Modern Pathology, vol. 27, p. 222-230, (2014).

Forster, I. et al. "Phosphate transporters of the SLC20 and SLC34 families", Molecular Aspects of Medicine, 34, p. 386-395 (2013).

Gordon et al. "A phase I study of the safety and pharmacokinetics of DNIB0600A, an anti-NaPi2b antibody-drug-conjugate (ADC), in patients (pts) with non-small cell lung cancer (NSCLC) and platinum-resistant ovarian cancer (OC)", Journal of Clinical Oncology, vol. 31, No. 15, suppl., Abstract No. 2507, p. 1-4 (2013).

Grill, et al. "Hypercalcemia of Malignancy", Reviews in Endocrine & Metabolic Disorders, vol. 1, p. 253-263 (2000).

Ikezoe, "Pathogenesis of disseminated intravascular coagulation in patients with acute promyelocytic leukemia, and its treatment using recombinant human soluble thrombomodulin", Journal of Hematology, vol. 100, p. 27-37 (2014).

Kim, et al., "Microarray Analysis of Papillary Thyroid Cancers in Korean", The Korean Journal of Internal Medicine. Vol. 25, No. 4, p. 399-407, (2010).

Kiyamova, R. et al. "Immunohistochemical Analysis of NAPI2B Protein (MX35 Antigen) Expression and Subcellular Localization in Human Normal and Cancer Tissues", Experimental Oncology, vol. 33, No. 3, p. 157-161 (2011).

Kunik et al., "Structural Consensus among Antibodies Defines the Antigen Binding Site", PLoS Computational Biology, vol. 8, Issue 2, 12 pages, (2012).

Lindegren S., et al. "Binding Affinity, Specificity and Comparative Biodistribution of the Parental Murine Monoclonal Antibody MX35 (Anti-NaPi2b) and Its Humanized Version Rebmab200", PLOS One, p. 1-16 (2015).

Mattes, M. et al. "Mouse Monoclonal Antibodies to Human Epithelial Differentiation Antigens Expressed on the Surface of Ovarian Carcinoma Ascites Cells", Cancer Research, 47, p. 6741-6750(1987).

Mersana Therapeutics, Clinical Trial. Identifier: NCT03319628, "First-in-Human Study of XMT-1536 in Cancers Likely to Express NaPi2b", First Posted Oct. 24, 2017, 12 pages.

Rangel, L. et al. "Characterization of novel human ovarian cancer-specific transcripts (HOSTs) identified by serial analysis of gene expression", Oncogene, 22, p. 7225-7232 (2003).

Saber H., et al. "An FDA oncology analysis of antibody-drug conjugates," Regulatory Toxicology and Pharmacology, vol. 71, p. 444-452 (2015).

Thornton et al. "Prediction of progress at last" Nature, vol. 354, p. 105-106 (1991).

Wagner, C. et al. "The SLC34 family of sodium-dependent phosphate transporters", Eur J Physiol, 466, p. 139-153 (2014).

Yin, B. W.T et al. "Monoclonal antibody MX35 detects the membrane transporter NaPi2b (SLC34A2) in human carcinomas", Cancer Immunity, vol. 8, 1-9, (2008).

Yurkovetskiy et al., "Abstract 48: Non-clinical pharmacokinetics of XMT-1522, a HER2 targeting auristatin-based antibody drug conjugate", AACR Annual meeting 2017, Apr. 2017, poster presentation, Cancer Research, 77(13 supplem), 2017, 1 page.

\* cited by examiner

Figure 1

Mers67 Full length heavy chain:

EcoRI - Kozak sequence - Artificial signal peptide - heavy chain variable region (Human) - Rabbit IgG1 constant region - HindIII Heavy chain sequence: 461aa MGWSCIILFLVATATGVHSQVQLVQSGAEVVKPGASVKMSCKASGYTFTGYNIHWVKQAPGQGLEWIGAIYPGNGDTSYKQKFRGRATL
TADTSTSTVYMELSSLRSEDSAVYYCARGETARAYFAYWGQGTLVTVSSGQPKAPSVFPLAPCCGDTPSSTVTLGCLVKGYLPEPVTV
TWNSGTLTNGVRTFPSVRQSSGLYSLSSVVSVTSSSQPVTCNVAHPATNTKVDKTVAPSTCSKPTCPPPELLGGPSVFIFPPKPKDTLMI
SRTPEVTCVVVDVSQEDPEVQFTWYINNEQVRTARPPLREQQFNSTIRVVSTLPIAHQDWLRGKEFKCKVHNKALPAPIEKTISKARG
QPLEPKVYTMGPPREELSSRSVSLTCMINGFYPSDISVEWEKNGKAEDNYKTTPAVLDSDGSYFLYSKLSVPTSEWQRGDVFTCSVMHEA
LHNHYTQKSISRSPGK

Gene sequence: 1410bp (codon optimization for HEK293)

GAATTCCGCCGCCACCATGGGCTGGTCCTGCATCATTCTGTTTCTGGTGGCCACAGCCACCGGCGTGCACTCTCAAGTTCAGCTGGTT
CAGTCTGGCGCCGAGGTTGTGAAACCTGGCGCCTCTGTGAAGATGAGCTGCAAGGCCAGCGGCTACACCTTCACCGGCTACAACATCCA
CTGGGTCAAGCAGGCCCCTGGACAGGGACTCGAATGGATCGGAGCCATCTATCCCGGCAACGGCGACACCAGCTACAAGCAGAAGTTCC
GGGGCAGAGCCACACTGACCGCCGATACAAGCACCAGCACCGTGTACATGGAACTGAGCAGCCTGAGAAGCGAGGACAGCGCCGTGTAC
TATTGCGCCAGAGGCGAAACAGCCAGAGCTACTTTGCCTATTGGGGCCAGGGAACCCTGGTCACCGTTAGCTCTGCACAGCCTAAGGC
TCCAGCGTGTTCCCTCTGGCTCCTTGCTGTGGCGATACCCCTAGCAGCACAGTGACATTGGCTGTCTGGTGAAGGGCTACCTGCCTG
AGCCTGTGACGGTGGACTGGAATAGCGGCACCCTGACCAACGGCGTGCGGACATTCCCTAGCGTGAGACAGAGCAGCGGCCTGTACTCT
CTGAGCAGCGTGGTGTCTGTGACCAGCAGCTCTCAACCTGTGACCTGCAATGTGGCCCATCCTGCTACTAATACAAGGTGGACAAAAC
CGTGGCTCCTTCTACAAGCTCACATGTCTTCCACCAGAGCTGCTCGAAGCCTGTGCGTCGTTCCAACCTAAGCCTA
AGACACCTGATGATCAGCAGAACCCCTGAGGTGACCTGGGTGGTGGACGTGTCCGAGGATGATCCTGAGGTGCAGTTCACCTGG
TACATTAACAACGAGCAAGTGCGGACTGCCAGAACTCCTCTGAGAGAGCAGCAGTTCAACAGCACTATTAGAGTGGTGTCTATCCTGT
TACCGTCACGGCATGGCGTGCGGTGCAAGCATTCAAGTGCAGGTGCACAACAAGGCCTGCCTGCCTGCTCCGACAAAACATCT
CTAAGGCCAGAGGCCAGCCCTCGAGCCTAAGGTGTACACTATGGGCCCTCCAAGAGAGGAACTGTCCAGCAGATCCGTGTCTCTGACC
TGCATGATTAACGGCTTCTACCCCAGCGACATCAGCGTGGAATGGGAGAAAAATGGCAAGGCTGAGGACAACTACAAGACAACCCCTG
CCGTGCTGGATAGCGACGGCAGCTACTTCCTGTACAGCAAGCTGAGCGTGCCCACCTCTGAATGGCAACGGGGAGATGTGTTCACTTGCA
GCGTGATGCACGAGGCCCTGCACAACCACTACACCCAGAAGTCCATCAGCAGGTCTCCAGGTAAATAAGCTT

Mers67 Full length light chain:

EcoRI - Kozak sequence - Artificial signal peptide - light chain variable region (human) - Rabbit Ig kappa-b4 chain C region - HindIII Light chain sequence: 230aa MGWSCIILFLVATATGVHSDIQMTQSPSSLSASVGDRVTITCSASQDIGHYLNWYQQKPGKTVKVLIYYTSSLYSGVPSRFSGSGSGTD
YTLTISSLQPEDFATYYCQQISKLPLTFGQGTRLELKRDPVAPTVLIFPPAADQVATGTVTIVCVANKYFPDVTVTWEVDGTTQTTGIE
NSKTPQNSADCTYNLSSTLTLTSTQYNSHKEYTCKVTQGTTSVVQSFNRGDC

Gene sequence: 717bp (codon optimization for HEK293)

GAATTCCGCCGCCACCATGGGCTGGTCCTGCATCATTCTGTTTCTGGTGGCCACAGCCACCGGCGTGCACAGCGATATTCAGATGACA
CAGAGCCCCAGCAGCCTGTCTGCCTCTGTGGGAGACAGAGTGACCATCACCTGTAGCGCCAGCCAGGATATCGGACACTTCCTGAACTG
GTATCAGCAGAAACCCGGCAAGACCGTGAAGGTGCTGATCTACTACACATCCAGCCTGTACAGCGGCGTGCCCAGCAGATTTTCTGGCA
GCGGCTCTGGCACCGACTACACCCTGACCATATCTAGCCTGCAGCCTGAGGACTTCGCCACCTACTACTGCCAGCAGTACAGCAAGCTG
CCCCTGACATTTGGCCAGGGCACCAAGCTGGAACTGAAGCGGGATCCTGTGGCCCCAACCGTGCTGATTTTCCACCCTGCTGCTGATCA
GGTGGCCACTGGCACAGTGACAATCGTGTGCGTGGCCAACAAGTACTTCCCTGACGTGACTGTGACCTGGGAAGTCGATGGCACCACAC
AGACCACAGGCATCGAGAACAGCAAGACCCCTCAGAACAGCGCCGACTGCACCTACAACCTGAGCAGCACCCTGACACTGACCAGCACA
CAGTACAACAGCCACAAAGAGTACACCTGTAAAGTCACCCAGGGCACAACCAGCGTGGTGCAGAGCTTCAACAGGGCGATTGCTA
AGCTT

Lane M: Protein Marker
Lane 1: Reducing conditions
Lane 2: Non-reducing conditions
Lane P: IgG from rabbit serum (Sigma, Cat.No.15006) as positive control Figure 4
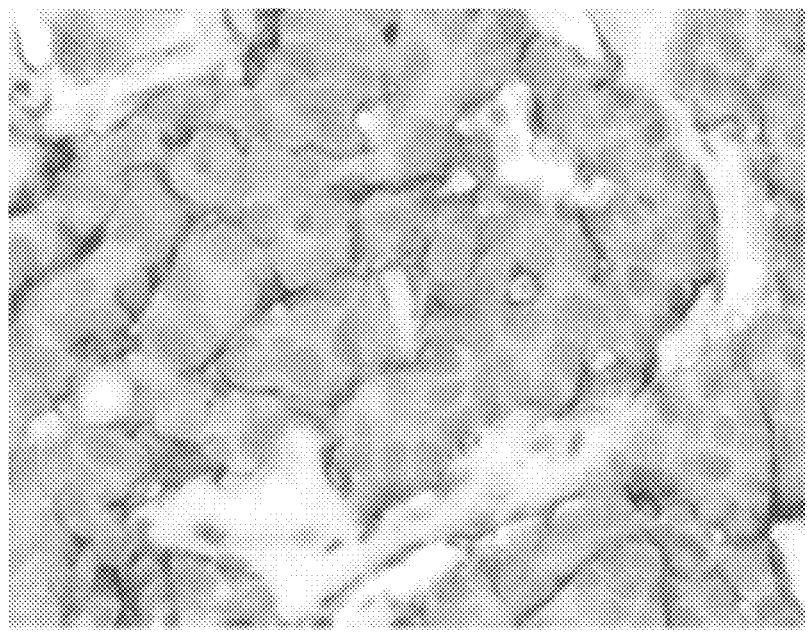
OVCAR3
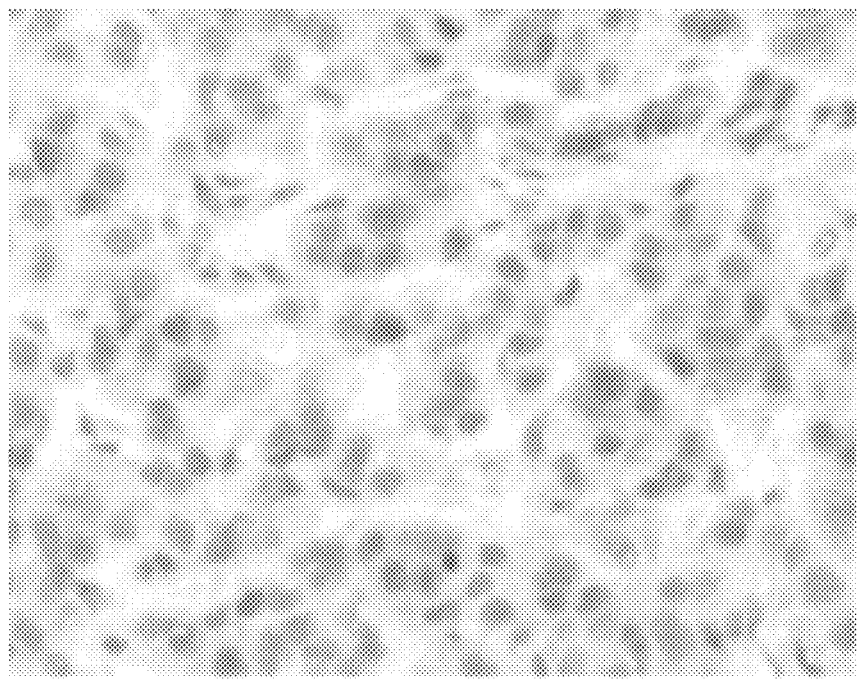
JIMT-1

Figure 5
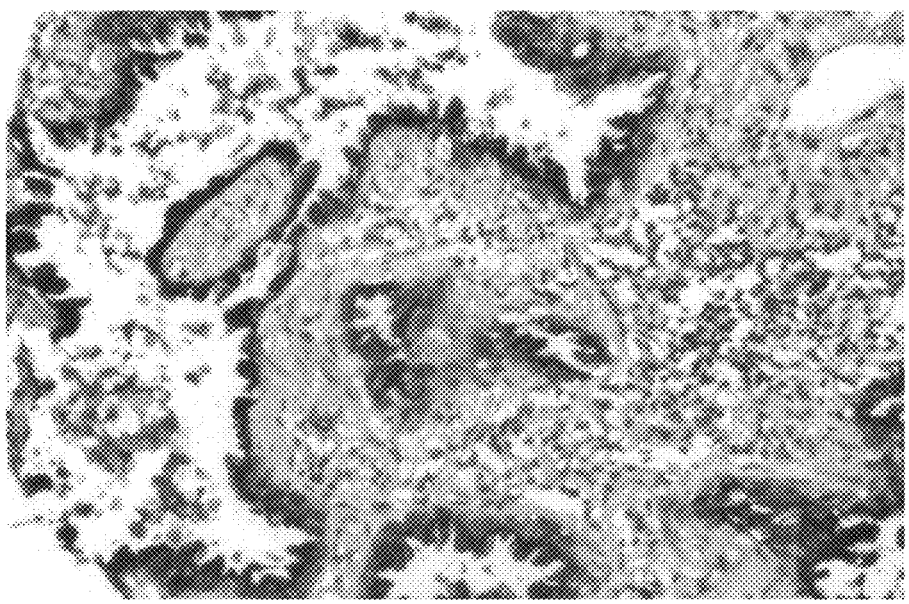
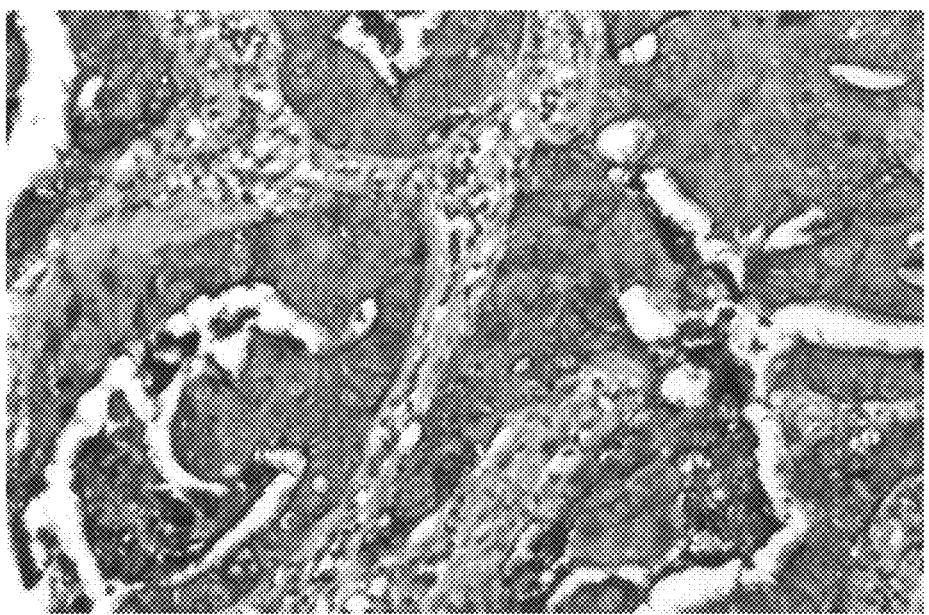

Figure 11
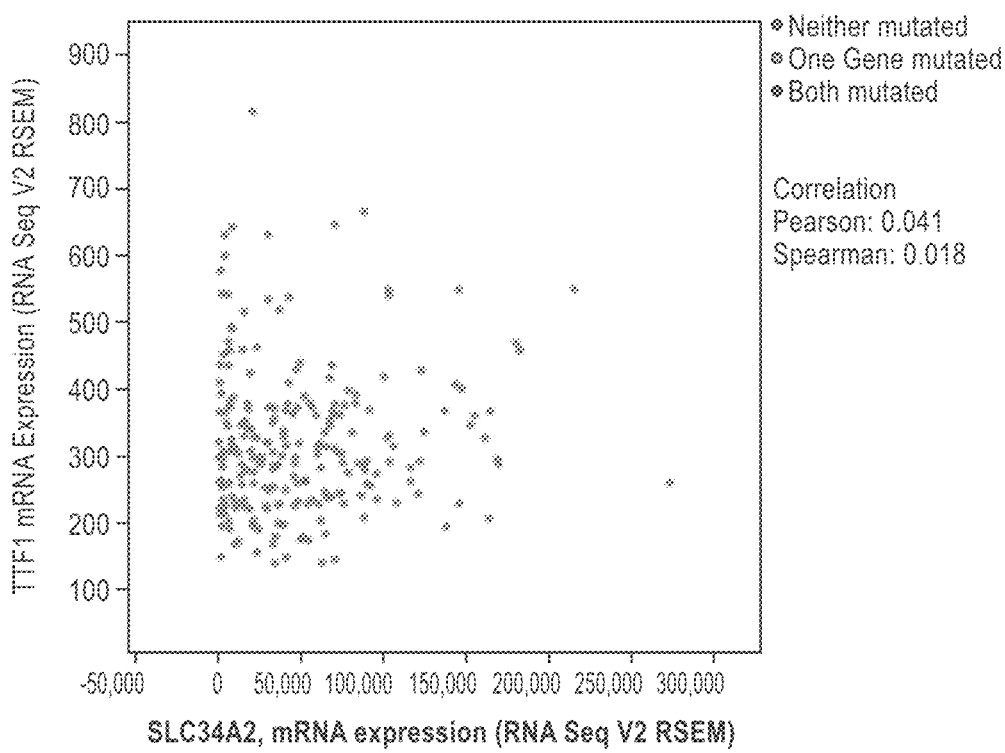
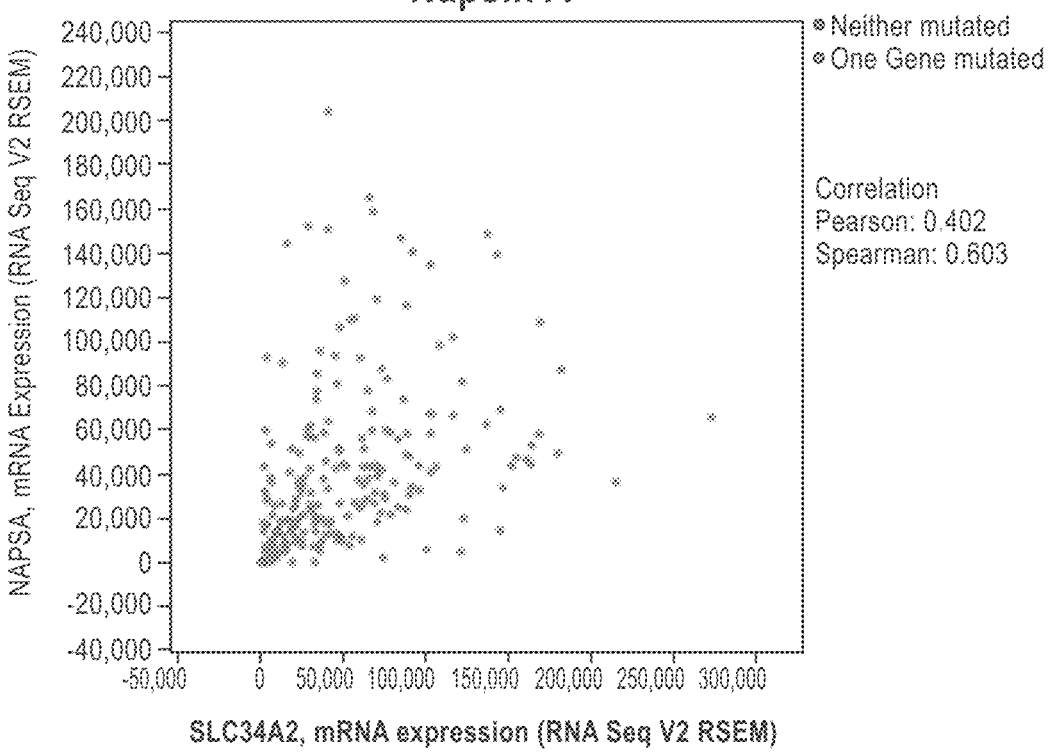

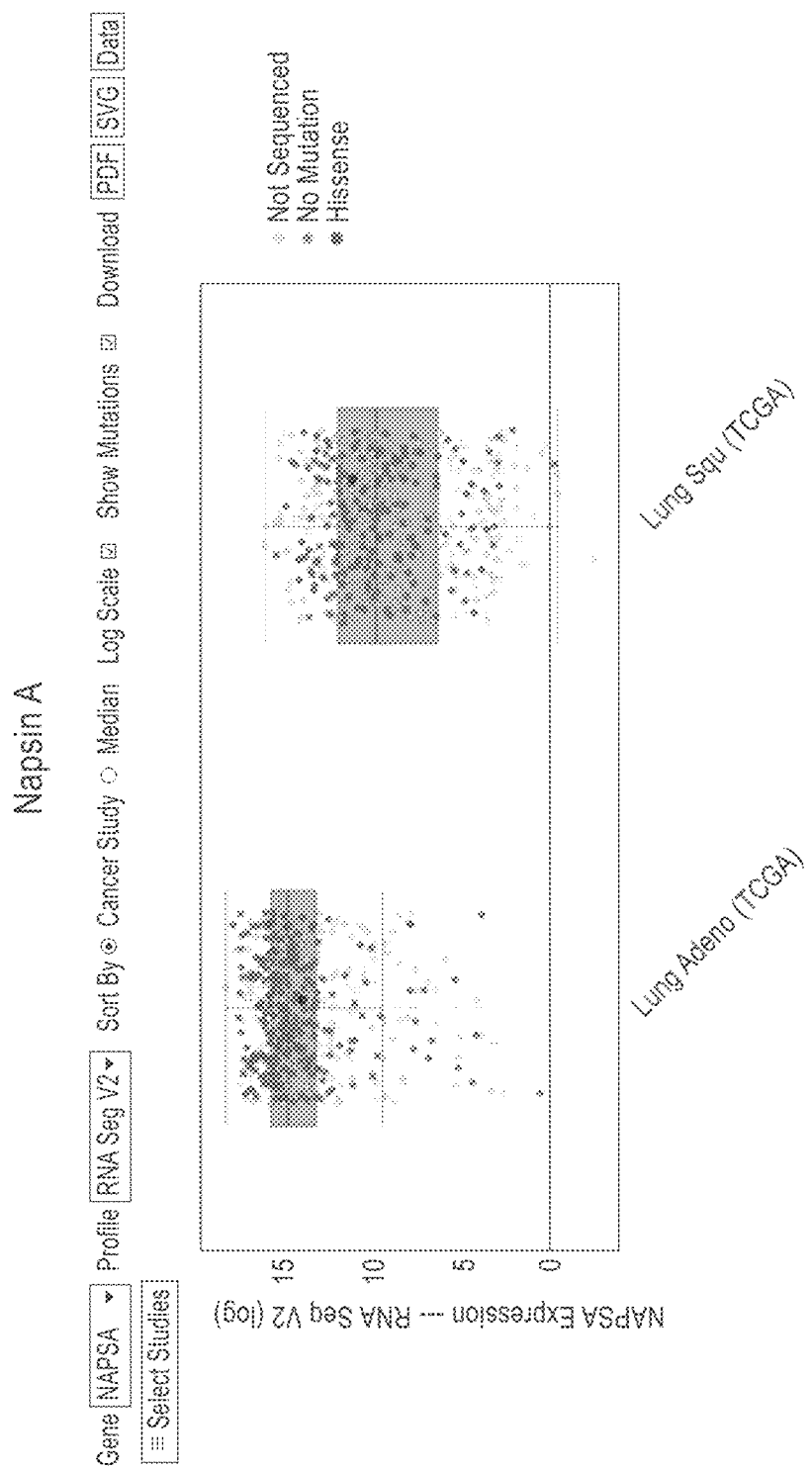

COMPOSITIONS AND METHODS FOR PREDICTING RESPONSE TO NAPI2B-TARGETED THERAPY

RELATED APPLICATIONS

This application claims benefit of, and priority to, U.S. Ser. No. 62/561,107 filed on Sep. 20, 2017, U.S. Ser. No. 62/571,397 filed on Oct. 12, 2017 and U.S. Ser. No. 62/718,692 filed on Aug. 14, 2918; the contents of each are hereby incorporated by reference in their entireties.

INCORPORATION OF SEQUENCE LISTING

This contents of the text filed named "MRSN-023_001US_SeqList_ST25.txt" which was created on Sep. 19, 2018 and is 19 KB in size, are hereby incorporated by reference in their entirety.

FIELD OF THE INVENTION

The invention relates generally to compositions and methods for stratifying responders and non-responders to treatment with NaPi2b-targeted antibody-polymer-drug conjugates. Also provided are methods of subtyping non-small cell lung carcinoma.

BACKGROUND OF THE INVENTION

NaPi2b (SLC34A2, NaPiIIb, Npt2), a multi-transmembrane, sodium-dependent phosphate transporter (Xu et al. Genomics 62:281-284 (1999)), is normally expressed at the brush border membrane of mammalian small intestine and participates in the transcellular inorganic phosphate (Pi) absorption, contributing to the maintenance of phosphate homeostasis in the body. The expression of NaPi2b at the protein level has been detected in the liver, at the apical surface of epithelial cells of mammary, salivary glands, and in the lungs, testis, salivary gland, thyroid gland, small intestine, and uterus. Mutations in NaPi2b have been associated with clinical syndromes of alveolar and testicular microlithiasis. NaPi2b is highly expressed in non-squamous non-small cell lung cancer (NSCLC), non-mucinous ovarian cancer and papillary thyroid cancer. NaPi2b-positive tissue immunoreactivity is present in 61% of NSCLC, and 92% of ovarian cancer specimens.

Ovarian cancer is one of the most common gynecologic malignancies and the fifth most frequent cause of cancer death in women. The high mortality rate results in part from the frequent diagnosis of ovarian cancer at advanced stages and the mortality rate is approximately 65% of the incidence rate. Epithelial tumors of ovary comprise 58% of all ovarian neoplasms and more than 90% of malignant tumors of ovary. Debulking surgery and platinum-based combination chemotherapy (including taxanes) are current treatment modalities; however, the majority of patients with relapsed epithelial ovarian cancer eventually succumb to the disease. There is a need for novel treatment modalities in ovarian cancer, including targeted therapies such as immunotherapy with monoclonal antibodies or cancer vaccine-based approaches.

NSCLC is any type of epithelial lung cancer other than small cell lung carcinoma (SCLC). NSCLC accounts for about 85% of all lung cancers. As a class, NSCLCs are relatively insensitive to chemotherapy, compared to small cell carcinoma. When possible, they are primarily treated by surgical resection with curative intent, although chemotherapy is increasingly being used both pre-operatively (neoadjuvant chemotherapy) and post-operatively (adjuvant chemotherapy). In the metastatic or inoperative setting, chemotherapy and/or immunotherapy is used, although the disease at this stage is largely incurable and survival times remains short. There is a need for novel treatment modalities in NSCLC, including targeted therapies such as immunotherapy with monoclonal antibodies or cancer vaccine-based approaches.

Additionally, there exists a need for diagnostic methods and kits to predict the response to therapies that target the biological activities of NaPi2b.

SUMMARY

In various aspects the invention provides methods of predicting the responsiveness of a cancer patient to treatment with a NaPi2b-targeted antibody drug conjugate detecting whether NaPi2b is present in a tumor sample obtained from the patient by contacting the tumor sample with an anti-NaPi2b antibody; detecting binding between NaPi2b and the antibody; and predicting that the patient with be responsive to treatment when the presence of NaPi2b in the tumor sample is detected.

In another aspect the invention provides methods of predicting the responsiveness of a cancer patient to treatment with a NaPi2b-targeted antibody drug conjugate by detecting whether NaPi2b is present in a tumor sample obtained from the patient by contacting the tumor sample with an anti-NaPi2b antibody; detecting binding between NaPi2b and the antibody; and scoring the detection pathologically. The pathology score correlates with responsiveness to treatment.

In yet a further aspect the invention provides methods of predicting the responsiveness of a cancer patient to treatment with a NaPi2b-targeted antibody drug conjugate by measuring the expression level of NaPi2b in a tumor sample obtained from the patient by contacting the tumor sample with an anti-NaPi2b antibody and predicting that the patient with be responsive to treatment when the expression level of NaPi2b in the tumor sample is higher than a predetermined cut-off point.

In various aspects of the methods of the invention, the methods further includes administering a NaPi2b-targeted antibody drug conjugate to the subject predicted to be responsive to treatment.

In another aspect the invention provides methods of treating a cancer in a subject with a NaPi2b-targeted antibody drug conjugate by detecting whether NaPi2b is present in a tumor sample obtained from the patient by contacting the tumor sample with an anti-NaPi2b antibody; detecting binding between NaPi2b and the antibody; predicting that the patient with be responsive to treatment with a NaPi2b-targeted antibody drug conjugate when the presence of NaPi2b in the tumor sample is detected; and administering a NaPi2b-targeted antibody drug conjugate to a subject predicted to be responsive.

In the various methods the predicting is accomplished by scoring the detection of NaPi2b protein pathologically. The pathology score correlates with responsiveness to treatment. The pathology score is a quantitative or a semi quantitative score. For example, the pathology score is determined by light microscopy or image analysis.

Alternatively, the predicting is accomplished by determining that the expression level of NaPi2b in the tumor sample is higher than a predetermined cut-off point. The predetermined cut-off point is calculated by for example, the H-score method.

In a further aspect the invention provides methods of subtyping a non-small cell lung carcinoma as adenocarcinoma by detecting whether NaPi2b is present in a non-small cell lung carcinoma sample by contacting the sample with an anti-NaPi2b antibody and detecting binding between NaPi2b and the antibody; and subtyping a non-small cell lung carcinoma as adenocarcinoma when the presence of NaPi2b in the sample is detected. Optionally, the method further includes detecting one or more of TTF-1, NapsinA, p63, p40 or CK5/6 in the a non-small cell lung carcinoma sample.

The cancer is a NaPi2b-expressing cancer. Example of include but are not limited to lung cancer, ovarian cancer, breast cancer, colorectal cancer, kidney cancer, thyroid cancer, renal cancer, salivary duct adenocarcinoma, endometrial cancer, cholangiocarcinoma, papillary thyroid cancer or papillary renal cancer. The lung cancer is for example, non-small lung carcinoma (NSCLC). In some aspects the NSCLC is non-squamous NSCLC. In some aspects the NSCLC is sub-typed as adenocarcinoma. The ovarian cancer is for example, epithelial ovarian cancer. The ovarian cancer is for example platinum-sensitive ovarian cancer. The ovarian cancer is for example platinum-refractory ovarian cancer.

The antibody of the NaPi2b-targeted antibody drug conjugate is XMT-1535. Preferably, the antibody of the NaPi2b-targeted antibody drug conjugate comprises: a variable heavy chain complementarity determining region 1 (CDRH1) comprising the amino acid sequence GYTFTGYNIH (SEQ ID NO: 3), a variable heavy chain complementarity determining region 2 (CDRH2) comprising the amino acid sequence AIYPGNGDTSYKQKFRG (SEQ ID NO: 4), a variable heavy chain complementarity determining region 3 (CDRH3) comprising the amino acid sequence GETARATFAY (SEQ ID NO: 5), a variable light chain complementarity determining region 1 (CDRL1) comprising the amino acid sequence SASQDIGNFLN (SEQ ID NO: 6), a variable light chain complementarity determining region 2 (CDRL2) comprising the amino acid sequence YTSSLYS (SEQ ID NO: 7), a variable light chain complementarity determining region 3 (CDRL3) comprising the amino acid sequence QQYSKLPLT (SEQ ID NO: 8).

The NaPi2b-targeted antibody drug conjugate is for example, an auristatin based NaPi2b-targeted antibody drug conjugate.

The NaPi2b-targeted antibody drug conjugate has the following formula:

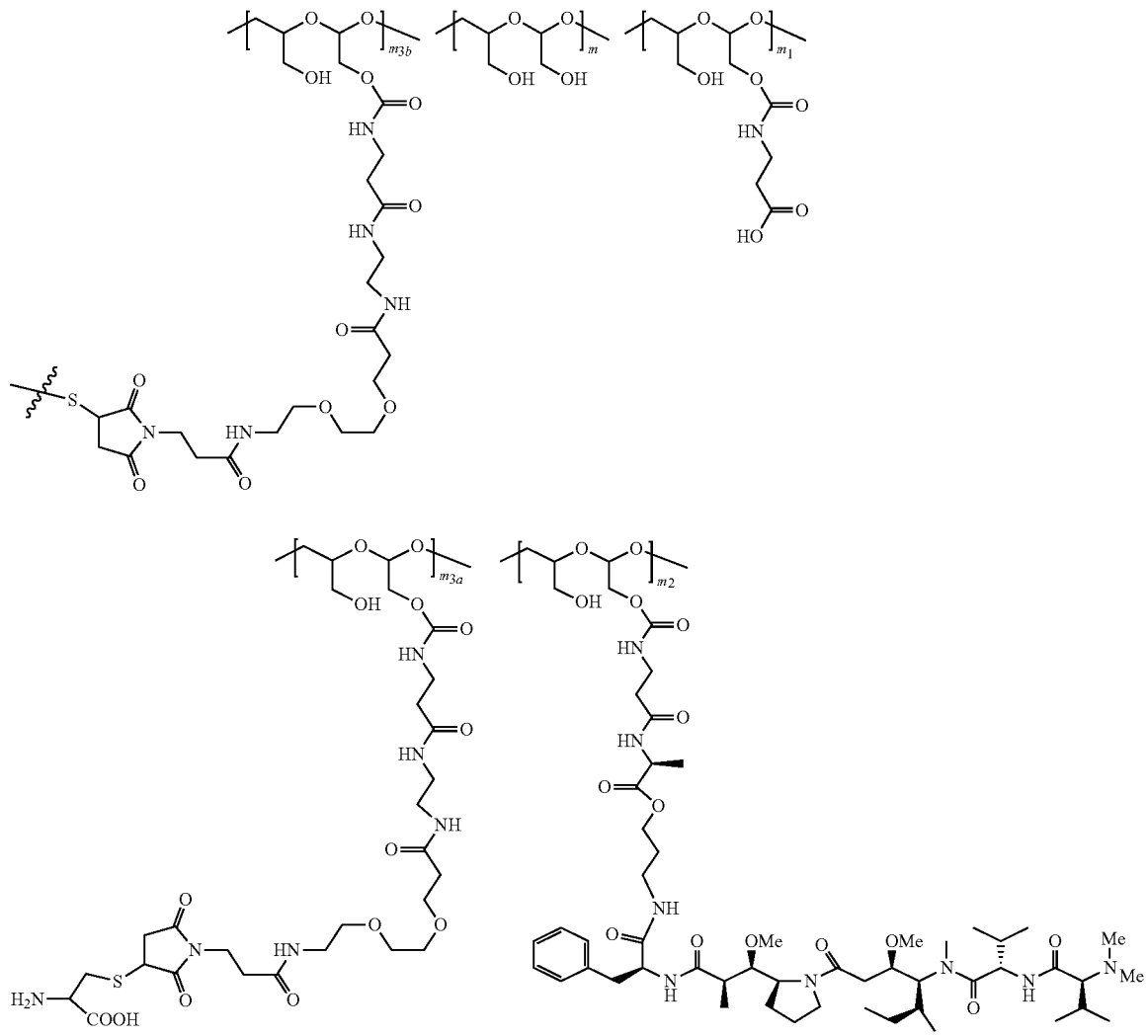

wherein:
m is an integer from 1 to about 300,
$m_1$ is an integer from 1 to about 140,
$m_2$ is an integer from 1 to about 40,
$m_{3a}$ is an integer from 0 to about 17,
$m_{3b}$ is an integer from 1 to about 8;
the sum of $m_{3a}$ and $m_{3b}$ ranges from 1 and about 18; and
the sum of m, $m_1$, $m_2$, $m_{3a}$, and $m_{3b}$ ranges from 15 to about 300;
the terminal

denotes the attachment of one or more polymeric scaffolds to the NaPi2b-targeted antibody XMT-1535.

Detecting is performed for example, immunohistochemically. Preferably, the anti-NaPi2b antibody is detected using a labeled secondary antibody.

The anti-NaPi2b antibody is a chimeric antibody. The chimeric antibody comprising a human variable region and a non-human constant region. The chimeric antibody comprises the variable region of antibody XMT-1535. The non-human constant region is rabbit.

The sample is for example but not limited to a formalin-fixed paraffin-embedded sample.

The invention further provide a chimeric antibody comprising: a variable heavy chain complementarity determining region 1 (CDRH1) comprising the amino acid sequence GYTFTGYNIH (SEQ ID NO: 3), a variable heavy chain complementarity determining region 2 (CDRH2) comprising the amino acid sequence AIYPGNGDTSYKQKFRG (SEQ ID NO: 4), a variable heavy chain complementarity determining region 3 (CDRH3) comprising the amino acid sequence GETARATFAY (SEQ ID NO: 5), a variable light chain complementarity determining region 1 (CDRL1) comprising the amino acid sequence SASQDIGNFLN (SEQ ID NO: 6), a variable light chain complementarity determining region 2 (CDRL2) comprising the amino acid sequence YTSSLYS (SEQ ID NO: 7), a variable light chain complementarity determining region 3 (CDRL3) comprising the amino acid sequence QQYSKLPLT (SEQ ID NO: 8). In some aspects the chimeric antibody includes the variable heavy chain of SEQ ID No: 1 and the variable light chain of SEQ ID No:2. The constant region is for example but not limited to, a rabbit constant region. For example, the chimeric antibody includes a rabbit IgG1 heavy chain constant region and a rabbit kappa constant region light chain. In preferred embodiments the chimeric antibody has the heavy chain constant region of SEQ ID No: 11 and the light chain constant region of SEQ ID NO: 12

Also include in the invention are plasmids containing the nucleic acid of SEQ ID NO: 17 and/or SEQ ID NO: 18 and cells containing the plasmid.

Also included in the invention are methods treating papillary thyroid cancer, papillary renal cancer, salivary duct adenocarcinoma, endometrial cancer or cholangiocarcinoma comprising administering to the subject NaPi2b-targeted antibody drug conjugate in an amount sufficient to alleviate the symptom of the cancer. The NaPi2b-targeted antibody drug conjugate is for example any conjugate disclosed in WO 2017/160754. For example the NaPi2b-targeted antibody drug conjugate is:

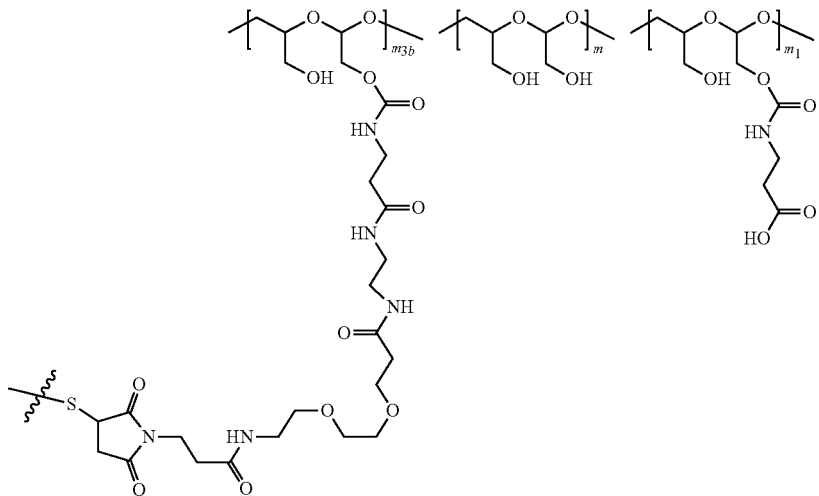

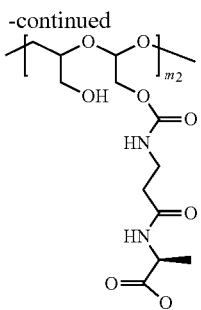
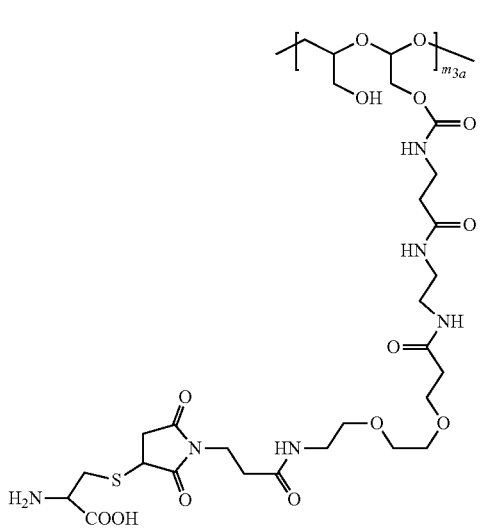
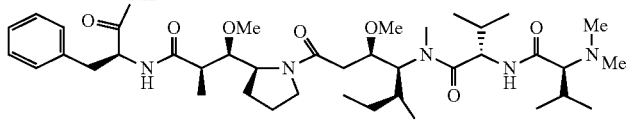

wherein:
m is an integer from 1 to about 300,
$m_1$ is an integer from 1 to about 140,
$m_2$ is an integer from 1 to about 40,
$m_{3a}$ is an integer from 0 to about 17,
$m_{3b}$ is an integer from 1 to about 8;
the sum of $m_{3a}$ and $m_{3b}$ ranges from 1 and about 18;
the sum of m, $m_1$, $m_2$, $m_{3a}$, and $m_{3b}$ ranges from 15 to about 300; and
the terminal

denotes the attachment of one or more polymeric scaffolds to the NaPi2b-targeted antibody XMT-1535.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE DRAWINGS

FIG. 1 illustrates the design of a chimeric antibody based upon humanized anti-NaPi2b antibody, XMT-1535. The chimeric antibody is referred to herein as MERS67.

FIG. 4 is a photograph showing representative immunohistochemical staining in OVCAR3 and JIMT-1 xenografts FIG. 5 shows immunohistochemical staining in two human lung adenocarcinomas.

DETAILED DESCRIPTION

Figure 2:
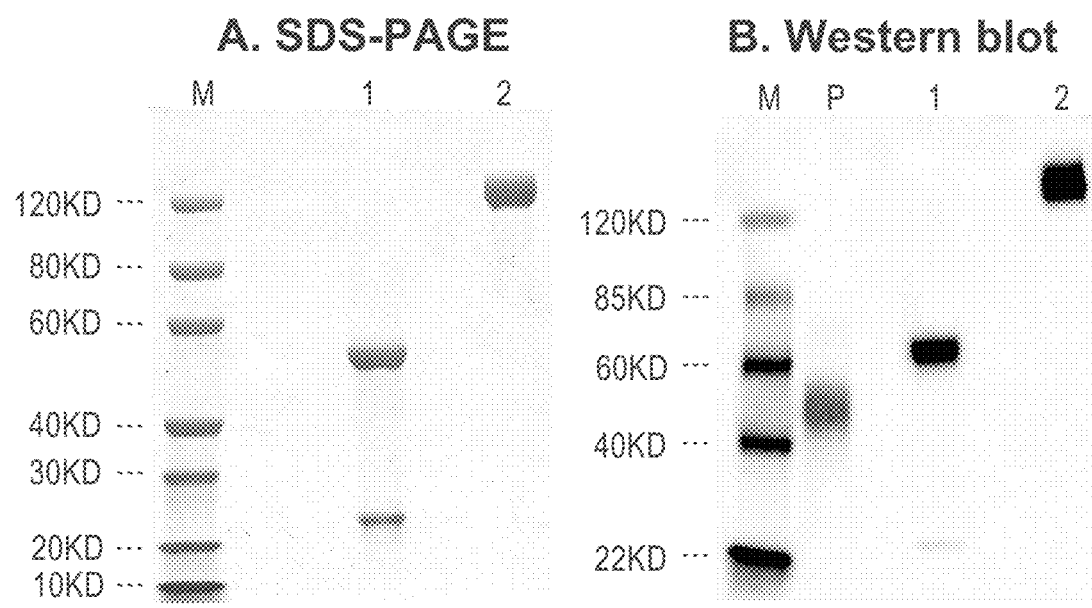
FIG. 2 is a photograph showing SDS-PAGE and Western blot analysis of Mers67 antibody.

The present in provides composition and methods of identifying subject whom would respond to a NaPi2b-targeted antibody-drug conjugate (such as NaPi2b antibody-polymer-drug conjugate).

The present invention is based in part upon the discovery of that a NaPi2b antibody-polymer-drug conjugate, (ADC) comprised of a fully humanized IgG1 antibody against NaPi2b, XMT-1535, has shown anti-tumor effect in models of both lung and ovarian cancer. (See, WO 2017/160754, the contents of which are incorporated by reference in its entirety). Efficacy of an ADC is due, at least in part, to the degree or pattern of target expression in a tumor or tumor model. In order to accurately describe the pattern of NaPi2b expression in models of human tumors and in primary human tumors a reagent, MERS67 (aka MER67) was developed and validated for immunohistochemistry (IHC). Understanding the NaPi2b expression in human tumors will provide a more rational and personalized therapy for patients having cancers that express NaPi2b.

MERS67 is a human rabbit chimera antibody that was based upon humanized anti-NaPi2b antibody, XMT-1535. XMT-1535 is the antibody portion of ADC disclosed in WO 2017/160754. Specifically, MERS67 contains the human and heavy light chain region of XMT-1535 joined to a rabbit IgG1 constant region or the rabbit Ig kappa-b4 chain C region, respectively.

Accordingly, the present invention provides in part, a NaPi2b chimeric antibody. More specifically, the present invention provides a NaPi2b chimeric antibody based upon the variable regions of XMT-1535. The invention further provides methods of predicting the responsiveness of a cancer patient to treatment with a NaPi2b-targeted polymer antibody-drug conjugate disclosed in WO 2017/160754 by determining the expression levels of NaPi2b of the tumor sample. In specific embodiments, expression levels of NaPi2b of the tumor sample is determined immunohistochemically using MERS67.

The present invention also provides in part a method of identifying patients who would benefit from treatment with a NaPi2b-targeted polymer antibody-drug conjugate disclosed in WO 2017/160754 by (i) determining the expression levels of NaPi2b of the tumor sample as determined immunohistochemically using MERS67 and (ii) informing the patient that they would benefit from treatment with a NaPi2b-targeted polymer antibody-drug conjugate.

The present invention also provides in part a method of predicting the responsiveness of a cancer patient to treatment with a NaPi2b-targeted polymer antibody-drug conjugate comprising the steps of (i) determining the expression levels of NaPi2b of the tumor sample as determined immunohistochemically using MERS67 and (ii) classifying the patient as having a high likelihood of responding to the treatment wherein a level of NaPi2b in the tumor sample obtained from the patient at or higher than a predetermined cut-off point indicates that the patient has increased likelihood of benefit from treatment with a NaPi2b-targeted polymer antibody-drug conjugate. The present invention also provides in part a method for determining the likelihood that a patient with cancer will exhibit benefit from treatment with a NaPi2b-targeted polymer antibody-drug conjugate, the method comprising: determining an expression level of NaPi2b in a sample obtained from the patient, wherein a level of NaPi2b in the sample obtained from the patient at or higher than a predetermined cut-off point indicates that the patient has increased likelihood of benefit from the anti-cancer therapy.

The present invention also provides in part a method for optimizing the therapeutic efficacy of an anti-cancer therapy comprising a NaPi2b-targeted polymer antibody-drug conjugate, the method comprising: determining expression levels of NaPi2b in a tumor sample obtained from the patient, wherein a level of NaPi2b in the sample obtained from the patient at or higher than a predetermined cut-off point indicates that the patient has increased likelihood of benefit from the NaPi2b-targeted polymer antibody-drug conjugate therapy.

The present invention also provides in part a method for treating cancer in a patient, the method comprising determining that a tumor sample obtained from the patient has a level of NaPi2b at or above the level of NaPi2b in a reference sample and administering an effective amount of a NaPi2b-targeted polymer antibody-drug conjugate to said patient, whereby the cancer is treated.

The present invention also provides in part a method for monitoring effectiveness of treating cancer in a patient, the method comprising determining that a tumor sample obtained from the patient has a level of NaPi2b at or above the level of NaPi2b in a reference sample and administering an effective amount of a NaPi2b-targeted polymer antibody-drug conjugate to said patient, whereby the cancer is treated The present invention enables oncologists to increase monitoring of and/or provide more aggressive and optimal preventive interventions or treatments to specific subsets of patients.

Chimeric NaPi2b Antibodies

The present invention provide chimeric antibodies having human variable regions and non-human constant regions. Specifically the chimeric antibodies described herein specifically recognize NaPi2b expression. Exemplary human variable regions used in the chimeric antibodies disclosed herein include, for example, the variable regions of the anti-NaPi2b antibody described in WO 2017/160754 and referred to XMT-1535. XMT-1535 antibodies show specificity for human NaPi2b and they have been shown to inhibit the functional activity of NaPi2b in vitro.

A specific chimeric NaPi2b antibody according to the invention includes a heavy chain variable region (VH) and a light chain variable region (VL), as shown in the amino acid and nucleic acid sequences presented below.

The complementarity regions (CDRs) of the heavy chain and the light chain are underlined in the amino acid sequences presented below. The amino acids encompassing the complementarity determining regions (CDRs) for the XMT-1535 antibody are as defined by E. A. Kabat et al. (See Kabat, E. A., et al., Sequences of Protein of immunological interest, Fifth Edition, US Department of Health and Human Services, US Government Printing Office (1991)) and are disclosed in U.S. Pat. No. 8,603,474, and the amino acids encompassing the CDRs for the 10H1.11.4B antibody are as defined in U.S. Pat. No. 8,535,675.

The constant region of the chimeric antibodies according to the invention can be derived from any species other than human. For example, the heavy and light chain constant regions derived from for example, but not limited to a rabbit, mouse, rat, horse, cow, or chicken.

In some aspects, the chimeric antibody according to the invention includes a rabbit heavy chain constant region and a rabbit light chain constant region. For example, the chimeric antibody according to the invention includes a rabbit IgG1 constant region and a rabbit IG kappa constant region.

```
XMT-1535 Heavy chain variable region amino acid sequence
                                                              (SEQ ID NO: 1)
QVQLVQSGAEVVKPGASVKMSCKASGYTFTGYNIHWVKQAPGQGLEWIGAIYPGNGDTSYKQKFRGRATLTADTSTSTV

YMELSSLRSEDSAVYYCARGETARATFAYWGQGTLVTVSSG

CDRH1:
                                                              (SEQ ID NO: 3)
GYTFTGYNIH

CDRH2:
                                                              (SEQ ID NO: 4)
AIYPGNGDTSYKQKFRG

CDRH3:
                                                              (SEQ ID NO: 5)
GETARATFAY

XMT-1535 Heavy chain variable region nucleic acid sequence
                                                              (SEQ ID NO: 9)
CAAGTTCAGCTGGTTCAGTCTGGCGCCGAGGTTGTGAAACCTGGCGCCTCTGTGAAGATGAGCTGCAAGGCCAGCGGCT

ACACCTTCACCGGCTACAACATCCACTGGGTCAAGCAGGCCCCTGGACAGGGACTCGAATGGATCGGAGCCATCTATCC

CGGCAACGGCGACACCAGCTACAAGCAGAAGTTCCGGGGCAGAGCCACACTGACCGCCGATACAAGCACCAGCACCGTG

TACATGGAACTGAGCAGCCTGAGAAGCGAGGACAGCGCCGTGTACTATTGCGCCAGAGGCGAAACAGCCAGAGCCACCT

TTGCCTATTGGGGCCAGGGAACCCTGGTCACCGTTAGCTCT

XMT-1535 Light chain variable region amino acid sequence
                                                              (SEQ ID NO: 2)
DIQMTQSPSSLSASVGDRVTITCSASQDIGNFLNWYQQKPGKTVKVLIYYTSSLYSGVPSRFSGSGSGTDYTLTISSLQ

PEDFATYYCQQYSKLPLTFGQGTKLELKR

CDRL1:
                                                              (SEQ ID NO: 6)
SASQDIGNFLN

CDRL2:
                                                              (SEQ ID NO: 7)
YTSSLYS

CDRL3:
                                                              (SEQ ID NO: 8)
QQYSKLPLT

XMT-1535 Light chain variable region nucleic acid sequence
                                                              (SEQ ID NO: 10)
GATATTCAGATGACACAGAGCCCCAGCAGCCTGTCTGCCTCTGTGGGAGACAGAGTGACCATCACCTGTAGCGCCAGCC

AGGATATCGGCAACTTCCTGAACTGGTATCAGCAGAAACCCGGCAAGACCGTGAAGGTGCTGATCTACTACACCTCCAG

CCTGTACAGCGGCGTGCCCAGCAGATTTTCTGGCAGCGGCTCTGGCACCGACTACACCCTGACCATATCTAGCCTGCAG

CCTGAGGACTTCGCCACCTACTACTGCCAGCAGTACAGCAAGCTGCCCCTGACATTTGGCCAGGGCACCAAGCTGGAAC

TGAAG
```

In a preferred embodiment the chimeric antibody according to the invention includes a rabbit heavy chain constant region (VH), and a light chain variable region (VL), as shown in the amino acid and nucleic acid sequences presented below.

```
Rabbit IgG1 Constant Region Amino Acid Sequence
                                                            (SEQ ID NO: 11)
GQPKAPSVFPLAPCCGDTPSSTVTLGCLVKGYLPEPVTVTWNSGTLTNGVRTFPSVRQSSGLYSLSSVVSVTSSSQPVTCNV AHPATNTKVDKTVAPSTCSKPTCPPPELLGGPSVFIFPPKPKDTLMISRTPEVTCVVVDVSEDDPEVQFTWYINNEQVRTAR PPLREQQFNSTIRVVSTLPIAHEDWLRGKEFKCKVHNKALPAPIEKTISKARGQPLEPKVYTMGPPREELSSRSVSLTCMIN

GFYPSDISVEWEKNGKAEDNYKTTPAVLDSDGSYFLYSKLSVPTSEWQRGDVFTCSVMHEALHNHYTQKSISRSPGK

Rabbit Ig kappa-b4 Constant Region Amino Acid Sequence
                                                            (SEQ ID NO: 12)
RDPVAPTVLIFPPAADQVATGTVTIVCVANKYFPDVTVTWEVDGTTQTTGIENSKTPQNSADCTYNLSSTLTLTSTQYNSHKE

YTCKVTQGTTSVVQSFNRGDC

Rabbit IgG1 Constant Region Nucleic Acid Sequence
                                                            (SEQ ID NO: 13)
GGACAGCCTAAGGCTCCCAGCGTGTTCCCTCTGGCTCCTTGCTGTGGCGATACCCCTAGCAGCACAGTGACACTGGGCTGTC TGGTCAAGGGCTACCTGCCTGAACCTGTGACCGTGACCTGGAATAGCGGCACCCTGACCAACGGCGTGCGGACATTTCCTAG CGTCAGACAGAGCAGCGGCCTGTACTCTCTGAGCAGCGTGGTGTCTGTGACCAGCAGCTCTCAGCCTGTGACCTGCAATGTG GCCCATCCTGCCACCAACACCAAGGTGGACAAAACCGTGGCTCCCTCCACCTGTAGCAAGCCCACATGTCCTCCACCAGAGC TGCTCGGAGGCCCCTCCGTGTTTATCTTCCCACCTAAGCCTAAGGACACCCTGATGATCAGCAGAACCCCTGAAGTGACCTG CGTGGTGGTGGACGTGTCCGAGGATGATCCTGAGGTGCAGTTCACCTGGTACATCAACAACGAGCAAGTGCGGACCGCCAGA CCTCCTCTGAGAGAGCAGCAGTTCAACAGCACCATCAGAGTGGTGTCTACCCTGCCTATCGCTCACGAGGATTGGCTGCGGG GCAAAGAGTTCAAGTGCAAGGTGCACAACAAGGCCCTGCCTGCTCCTATCGAGAAAACCATCTCCAAGGCCAGAGGCCAGCC ACTGGAACCCAAGGTGTACACAATGGGCCCTCCAAGAGAGGAACTGTCCAGCAGATCCGTGTCTCTGACCTGCATGATCAAC GGCTTCTACCCCAGCGACATCAGCGTGGAATGGGAGAAGAATGGCAAGGCCGAGGACAACTACAAGACAACCCCTGCCGTGC TGGATAGCGACGGCAGCTACTTCCTGTACAGCAAGCTGAGCGTGCCCACCTCTGAATGGCAACGGGGAGATGTGTTTACCTG

CAGCGTGATGCACGAGGCCCTGCACAACCACTACACCCAGAAGTCCATCAGCAGGTCCCCAGGCAAA

Rabbit Ig kappa-b4 Constant Region Nucleic Acid Sequence
                                                            (SEQ ID NO: 14)
AGGGATCCTGTGGCTCCCACCGTGCTGATTTTTCCACCAGCCGCTGATCAGGTGGCCACTGGCACAGTGACAATCGTGTGCGTG GCCAACAAGTACTTCCCCGACGTGACCGTGACCTGGGAAGTCGATGGCACCACACAGACCACAGGCATCGAGAACAGCAAGACC CCTCAGAACAGCGCCGACTGCACCTACAACCTGAGCAGCACCCTGACACTGACCAGCACACAGTACAACAGCCACAAAGAGTAC

ACCTGTAAAGTCACCCAGGGCACAACCAGCGTGGTGCAGAGCTTCAACAGAGGCGATTGC
```

In a more preferred embodiment, the chimeric NaPi2b antibody, MERS67, includes a heavy and light chain amino acid and nucleic acid sequence presented below.

```
Chimeric NaPi2b antibody heavy chain amino acid
sequence
                                    (SEQ ID NO: 15)
QVQLVQSGAEVVKPGASVKMSCKASGYTFTGYNIHWVKQAPGQGLEWIGA

IYPGNGDTSYKQKFRGRATLTADTSTSTVYMELSSLRSEDSAVYYCARGE

TARATFAYWGQGTLVTVSSGQPKAPSVFPLAPCCGDTPSSTVTLGCLVKG

YLPEPVTVTWNSGTLTNGVRTFPSVRQSSGLYSLSSVVSVTSSSQPVTCN

VAHPATNTKVDKTVAPSTCSKPTCPPPELLGGPSVFIFPPKPKDTLMISR

TPEVTCVVVDVSEDDPEVQFTWYINNEQVRTARPPLREQQFNSTIRVVST

LPIAHEDWLRGKEFKCKVHNKALPAPIEKTISKARGQPLEPKVYTMGPPR

EELSSRSVSLTCMINGFYPSDISVEWEKNGKAEDNYKTTPAVLDSDGSYF

LYSKLSVPTSEWQRGDVFTCSVMHEA LHNHYTQKSISRSPGK

Chimeric NaPi2b antibody light chain amino acid
sequence
                                    (SEQ ID NO: 16)
DIQMTQSPSSLSASVGDRVTITCSASQDIGNFLNWYQQKPGKTVKVLIYY

TSSLYSGVPSRFSGSGSGTDYTLTISSLQPEDFATYYCQQYSKLPLTFGQ
```

-continued
GTKLELKRDPVAPTVLIFPPAADQVATGTVTIVCVANKYFPDVTVTWEVD

GTTQTTGIE NSKTPQNSADCTYNLSSTLTLTSTQYNSHKEYTCKVTQGT

TSVVQSFNRGDC

Chimeric NaPi2b antibody heavy chain nucleic acid
sequence
(SEQ ID NO: 17)
CAAGTTCAGCTGGTTCAGTCTGGCGCCGAGGTTGTGAAACCTGGCGCCTC

TGTGAAGATGAGCTGCAAGGCCAGCGGCTACACCTTCACCGGCTACAACA

TCCACTGGGTCAAGCAGGCCCCTGGACAGGGACTCGAATGGATCGGAGCC

ATCTATCCCGGCAACGGCGACACCAGCTACAAGCAGAAGTTCCGGGGCAG

AGCCACACTGACCGCCGATACAAGCACCAGCACCGTGTACATGGAACTGA

GCAGCCTGAGAAGCGAGGACAGCGCCGTGTACTATTGCGCCAGAGGCGAA

ACAGCCAGAGCCACCTTTGCCTATTGGGGCCAGGGAACCCTGGTCACCGT

TAGCTCTGGACAGCCTAAGGCTCCCAGCGTGTTCCCTCTGGCTCCTTGCT

GTGGCGATACCCCTAGCAGCACAGTGACACTGGGCTGTCTGGTCAAGGGC

TACCTGCCTGAACCTGTGACCGTGACCTGGAATAGCGGCACCCTGACCAA

CGGCGTGCGGACATTTCCTAGCGTCAGACAGAGCAGCGGCCTGTACTCTC

TGAGCAGCGTGGTGTCTGTGACCAGCAGCTCTCAGCCTGTGACCTGCAAT

GTGGCCCATCCTGCCACCAACACCAAGGTGGACAAAACCGTGGCTCCCTC

CACCTGTAGCAAGCCCACATGTCCTCCACCAGAGCTGCTCGGAGGCCCCT

CCGTGTTTATCTTCCCACCTAAGCCTAAGGACACCCTGATGATCAGCAGA

ACCCCTGAAGTGACCTGCGTGGTGGTGGACGTGTCCGAGGATGATCCTGA

GGTGCAGTTCACCTGGTACATCAACAACGAGCAAGTGCGGACCGCCAGAC

CTCCTCTGAGAGAGCAGCAGTTCAACAGCACCATCAGAGTGGTGTCTACC

CTGCCTATCGCTCACGAGGATTGGCTGCGGGGCAAAGAGTTCAAGTGCAA

GGTGCACAACAAGGCCCTGCCTGCTCCTATCGAGAAAACCATCTCCAAGG

CCAGAGGCCAGCCACTGGAACCCAAGGTGTACACAATGGGCCCTCCAAGA

GAGGAACTGTCCAGCAGATCCGTGTCTCTGACCTGCATGATCAACGGCTT

CTACCCCAGCGACATCAGCGTGGAATGGGAGAAGAATGGCAAGGCCGAGG

ACAACTACAAGACAACCCCTGCCGTGCTGGATAGCGACGGCAGCTACTTC

CTGTACAGCAAGCTGAGCGTGCCCACCTCTGAATGGCAACGGGGAGATGT

GTTTACCTGCAGCGTGATGCACGAGGCCCTGCACAACCACTACACCCAGA

AGTCCATCAGCAGGTCCCCAGGCAAA

Chimeric NaPi2b antibody light chain nucleic acid
sequence
(SEQ ID NO: 18)
GATATTCAGATGACACAGAGCCCCAGCAGCCTGTCTGCCTCTGTGGGAGA

CAGAGTGACCATCACCTGTAGCGCCAGCCAGGATATCGGCAACTTCCTGA

ACTGGTATCAGCAGAAACCCGGCAAGACCGTGAAGGTGCTGATCTACTAC

ACCTCCAGCCTGTACAGCGGCGTGCCCAGCAGATTTTCTGGCAGCGGCTC

TGGCACCGACTACACCCTGACCATATCTAGCCTGCAGCCTGAGGACTTCG

CCACCTACTACTGCCAGCAGTACAGCAAGCTGCCCCTGACATTTGGCCAG

GGCACCAAGCTGGAACTGAAGAGGGATCCTGTGGCTCCCACCGTGCTGAT

TTTTCCACCAGCCGCTGATCAGGTGGCCACTGGCACAGTGACAATCGTGT

GCGTGGCCAACAAGTACTTCCCCGACGTGACCGTGACCTGGGAAGTCGAT

GGCACCACACAGACCACAGGCATCGAGAACAGCAAGACCCCTCAGAACAG

CGCCGACTGCACCTACAACCTGAGCAGCACCCTGACACTGACCAGCACAC

AGTACAACAGCCACAAAGAGTACACCTGTAAAGTCACCCAGGGCACAACC

AGCGTGGTGCAGAGCTTCAACAGAGGCGATTGC

In some embodiments the chimeric NaPi2b antibody includes a variable heavy chain complementarity determining region 1 (CDRH1) comprising an amino acid sequence at least 90%, 91%, 92%, 93%, 94%, 95%, 96%, 97% 98%, 99% or more identical to the amino acid sequence GYTFTGYNIH (SEQ ID NO: 3); a variable heavy chain complementarity determining region 2 (CDRH2) comprising an amino acid sequence at least 90%, 91%, 92%, 93%, 94%, 95%, 96%, 97% 98%, 99% or more identical to the amino acid sequence AIYPGNGDTSYKQKFRG (SEQ ID NO: 4); and a variable heavy chain complementarity determining region 3 (CDRH3) comprising an amino acid sequence at least 90%, 91%, 92%, 93%, 94%, 95%, 96%, 97% 98%, 99% or more identical to the amino acid sequence GETARATFAY (SEQ ID NO: 5).

In some embodiments the chimeric NaPi2b antibody includes a variable light chain complementarity determining region 1 (CDRL1) comprising an amino acid sequence at least 90%, 91%, 92%, 93%, 94%, 95%, 96%, 97% 98%, 99% or more identical to the amino acid sequence SASQDIGNFLN (SEQ ID NO: 6); a variable light chain complementarity determining region 2 (CDRL2) comprising an amino acid sequence at least 90%, 91%, 92%, 93%, 94%, 95%, 96%, 97% 98%, 99% or more identical to the amino acid sequence YTSSLYS (SEQ ID NO: 7); and a variable light chain complementarity determining region 3 (CDRL3) comprising an amino acid sequence at least 90%, 91%, 92%, 93%, 94%, 95%, 96%, 97% 98%, 99% or more identical to the amino acid sequence QQYSKLPLT (SEQ ID NO: 8).

In some embodiments the chimeric NaPi2b antibody includes a CDRH1 comprising an amino acid sequence at least 90%, 91%, 92%, 93%, 94%, 95%, 96%, 97% 98%, 99% or more identical to the amino acid sequence GYTFTGYNIH (SEQ ID NO: 3); a CDRH2 comprising an amino acid sequence at least 90%, 91%, 92%, 93%, 94%, 95%, 96%, 97% 98%, 99% or more identical to the amino acid sequence AIYPGNGDTSYKQKFRG (SEQ ID NO: 4); a CDRH3 comprising an amino acid sequence at least 90%, 91%, 92%, 93%, 94%, 95%, 96%, 97% 98%, 99% or more identical to the amino acid sequence GETARATFAY (SEQ ID NO: 5); a CDRL1 comprising an amino acid sequence at least 90%, 91%, 92%, 93%, 94%, 95%, 96%, 97% 98%, 99% or more identical to the amino acid sequence SASQDIGNFLN (SEQ ID NO: 6); a CDRL2 comprising an amino acid sequence at least 90%, 91%, 92%, 93%, 94%, 95%, 96%, 97% 98%, 99% or more identical to the amino acid sequence YTSSLYS (SEQ ID NO: 7); and a CDRL3 comprising an amino acid sequence at least 90%, 91%, 92%, 93%, 94%, 95%, 96%, 97% 98%, 99% or more identical to the amino acid sequence QQYSKLPLT (SEQ ID NO: 8).

In some embodiments the chimeric NaPi2b antibody includes a variable heavy chain (VH) region comprising an amino acid sequence at least 90%, 91%, 92%, 93%, 94%, 95%, 96%, 97% 98%, 99% or more identical to the amino acid sequence of SEQ ID NO: 1. In some embodiments the chimeric NaPi2b antibody includes a variable light chain (VL) region comprising an amino acid sequence at least 90%, 91%, 92%, 93%, 94%, 95%, 96%, 97% 98%, 99% or more identical to the amino acid sequence of SEQ ID NO: 2.

In some embodiments the chimeric NaPi2b antibody includes a VH region comprising an amino acid sequence at least 90%, 91%, 92%, 93%, 94%, 95%, 96%, 97% 98%, 99% or more identical to the amino acid sequence of SEQ ID NO: 15, and a VL region comprising an amino acid sequence at least 90%, 91%, 92%, 93%, 94%, 95%, 96%, 97% 98%, 99% or more identical to the amino acid sequence of SEQ ID NO: 16.

In some embodiments the chimeric NaPi2b antibody includes a variable heavy chain complementarity determining region 1 (CDRH1) comprising an amino acid sequence at least 85%, 86%, 87% 88%, 89%, 90%, 91%, 92%, 93%, 94%, 95%, 96%, 97% 98%, 99% or more identical to the amino acid sequence GYTFTGYNIH (SEQ ID NO: 3); a variable heavy chain complementarity determining region 2 (CDRH2) comprising an amino acid sequence at least 85%, 86%, 87% 88%, 89%, 90%, 91%, 92%, 93%, 94%, 95%, 96%, 97% 98%, 99% or more identical to the amino acid sequence AIYPGNGDTSYKQKFRG (SEQ ID NO: 4); and a variable heavy chain complementarity determining region 3 (CDRH3) comprising an amino acid sequence at least 85%, 86%, 87% 88%, 89%, 90%, 91%, 92%, 93%, 94%, 95%, 96%, 97% 98%, 99% or more identical to the amino acid sequence GETARATFAY (SEQ ID NO: 5).

In some embodiments the chimeric NaPi2b antibody includes a variable light chain complementarity determining region 1 (CDRL1) comprising an amino acid sequence at least 85%, 86%, 87% 88%, 89%, 90%, 91%, 92%, 93%, 94%, 95%, 96%, 97% 98%, 99% or more identical to the amino acid sequence SASQDIGNFLN (SEQ ID NO: 6); a variable light chain complementarity determining region 2 (CDRL2) comprising an amino acid sequence at least 85%, 86%, 87% 88%, 89%, 90%, 91%, 92%, 93%, 94%, 95%, 96%, 97% 98%, 99% or more identical to the amino acid sequence YTSSLYS (SEQ ID NO: 7); and a variable light chain complementarity determining region 3 (CDRL3) comprising an amino acid sequence at least 85%, 86%, 87% 88%, 89%, 90%, 91%, 92%, 93%, 94%, 95%, 96%, 97% 98%, 99% or more identical to the amino acid sequence QQYSKLPLT (SEQ ID NO: 8).

In some embodiments the chimeric NaPi2b antibody includes a CDRH1 comprising an amino acid sequence at least 85%, 86%, 87% 88%, 89%, 90%, 91%, 92%, 93%, 94%, 95%, 96%, 97% 98%, 99% or more identical to the amino acid sequence GYTFTGYNIH (SEQ ID NO: 3); a CDRH2 comprising an amino acid sequence at least 85%, 86%, 87% 88%, 89%, 90%, 91%, 92%, 93%, 94%, 95%, 96%, 97% 98%, 99% or more identical to the amino acid sequence AIYPGNGDTSYKQKFRG (SEQ ID NO: 4); a CDRH3 comprising an amino acid sequence at least 85%, 86%, 87% 88%, 89%, 90%, 91%, 92%, 93%, 94%, 95%, 96%, 97% 98%, 99% or more identical to the amino acid sequence GETARATFAY (SEQ ID NO: 5); a CDRL1 comprising an amino acid sequence at least 85%, 86%, 87% 88%, 89%, 90%, 91%, 92%, 93%, 94%, 95%, 96%, 97% 98%, 99% or more identical to the amino acid sequence SASQDIGNFLN (SEQ ID NO: 6); a CDRL2 comprising an amino acid sequence at least 85%, 86%, 87% 88%, 89%, 90%, 91%, 92%, 93%, 94%, 95%, 96%, 97% 98%, 99% or more identical to the amino acid sequence YTSSLYS (SEQ ID NO: 7); and a CDRL3 comprising an amino acid sequence at least 85%, 86%, 87% 88%, 89%, 90%, 91%, 92%, 93%, 94%, 95%, 96%, 97% 98%, 99% or more identical to the amino acid sequence QQYSKLPLT (SEQ ID NO: 8).

In some embodiments the chimeric NaPi2b antibody includes a variable heavy chain (VH) region comprising an amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 1. In some embodiments the chimeric NaPi2b antibody includes a variable light chain (VL) region comprising an amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 2.

In some embodiments the chimeric NaPi2b antibody includes a VH region comprising an amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 15, and a VL region comprising an amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 16.

Those skilled in the art will recognize that it is possible to determine, without undue experimentation, if a chimeric antibody has the same specificity as a chimeric antibody disclosed herein (e.g., MERS67) by ascertaining whether the former prevents the latter from binding to a natural binding partner or other molecule known to be associated with NaPi2b. If the antibody being tested competes with the chimeric antibody disclosed herein, as shown by a decrease in binding by the chimeric antibody disclosed herein, then the two antibodies bind to the same, or a closely related, epitope.

An alternative method for determining whether a monoclonal antibody has the specificity of monoclonal antibody disclosed herein is to pre-incubate the chimeric antibody disclosed herein with soluble NaPi2b (with which it is normally reactive), and then add the antibody being tested to determine if the antibody being tested is inhibited in its ability to bind NaPi2b. If the antibody being tested is inhibited then, in all likelihood, it has the same, or functionally equivalent, epitopic specificity as the chimeric antibody disclosed herein.

Screening of chimeric antibodies disclosed herein, can also be carried out, e.g., by measuring NaPi2b-mediated activity, and determining whether the test chimeric antibody is able to modulate, block, inhibit, reduce, antagonize, neutralize or otherwise interfere with NaPi2b activity.

Chimeric antibodies can be made by recombinant DNA methods, such as those described in U.S. Pat. No. 4,816,567. DNA encoding the monoclonal antibodies disclosed herein can be readily isolated and sequenced using conventional procedures (e.g., by using oligonucleotide probes that are capable of binding specifically to genes encoding the heavy and light chains of murine antibodies). The hybridoma cells disclosed herein serve as a preferred source of such DNA. Once isolated, the DNA can be placed into expression vectors, which are then transfected into host cells such as simian COS cells, HEK293 cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody disclosed herein, or can be substituted for the variable domains of one antigen-combining site of an antibody disclosed herein to create a chimeric bivalent antibody.

A chimeric NaPi2b antibody is generated, for example, using the procedures described in the Examples provided below.

The chimeric NaPi2b antibodies disclosed herein can be expressed by a plasmid or vector containing a DNA segment encoding the antibody described above. The plasmid or vectors can be transfected in cells for expression. For example, the cells are HEK293 cells or CHO cells.

These vectors, plasmid and cells can be used to express large quantities of antibodies that can be used in a variety of ways. For example, to detect the presence of NaPi2b in a sample.

Antibodies are purified by well-known techniques, such as affinity chromatography using protein A or protein G, which provide primarily the IgG fraction of immune serum. Subsequently, or alternatively, the specific antigen that is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Chimeric antibodies disclosed herein are also useful in the detection of NaPi2b in patient samples and accordingly are useful as diagnostics. For example, NaPi2b antibodies disclosed herein are used in in vitro assays, e.g., IHC, ELISA, to detect NaPi2b levels in a patient sample.

NaPi2b-Targeted Polymer Antibody-Drug Conjugate

In some embodiments, the NaPi2b-targeted antibody, XMT-1535, can be connected with an agent to form a conjugate. In some embodiments, the agent is a therapeutic agent. In some embodiments, the agent is an antineoplastic agent. In some embodiments, the agent is a toxin or fragment thereof. In some embodiments, the agent is (a) an auristatin compound; (b) a calicheamicin compound; (c) a duocarmycin compound; (d) SN38, (e) a pyrrolobenzodiazepine; (f) a vinca compound; (g) a tubulysin compound; (h) a non-natural camptothecin compound; (i) a maytansinoid compound; (j) a DNA binding drug; (k) a kinase inhibitor; (l) a MEK inhibitor; (m) a KSP inhibitor; (n) a topoisomerase inhibitor; (o) a DNA-alkylating drug; (p) a RNA polymerase inhibitor; or analogues thereof. In some embodiments, the agent is conjugated to the NaPi2b-targeted antibody via a linker. In some embodiments, the linker is a cleavable linker. In some embodiments, the linker is a non-cleavable linker. In some embodiments, the agent is any of the toxins described herein.

In one aspect, the NaPi2b-targeted antibody conjugate described herein includes an isolated NaPi2b-targeted antibody, XMT-1535, connected directly or indirectly to one or more therapeutic or diagnostic agents ("D"). In some embodiments, the NaPi2b-targeted antibody conjugate also includes one or more polymeric scaffolds connected to the antibody, wherein each of the one or more D is independently connected to the antibody via the one or more polymeric scaffolds. In some embodiments the one or more D is AF-HPA.

In some embodiments, each of the one or more polymeric scaffolds that are connected to XMT-1535 comprises poly (1-hydroxymethylethylene hydroxymethyl-formal) (PHF), e.g., PHF having a molecular weight ranging from about 2 kDa to about 40 kDa. In other embodiments, the PHF having a molecular weight ranging from about 2 kDa to about 20 kDa. In some embodiments, the PHF having a molecular weight ranging from about 3 kDa to about 15 kDa. In other embodiments, the PHF having a molecular weight ranging from about 5 kDa to about 10 kDa.

In some embodiments, the PHF has a molecular weight ranging from about 6 kDa to about 8 kDa.

In some embodiments, the PHF has a molecular weight ranging from about 6 kDa to about 7 kDa.

In some embodiments, each of the one or more polymeric scaffolds independently is of Formula (I):

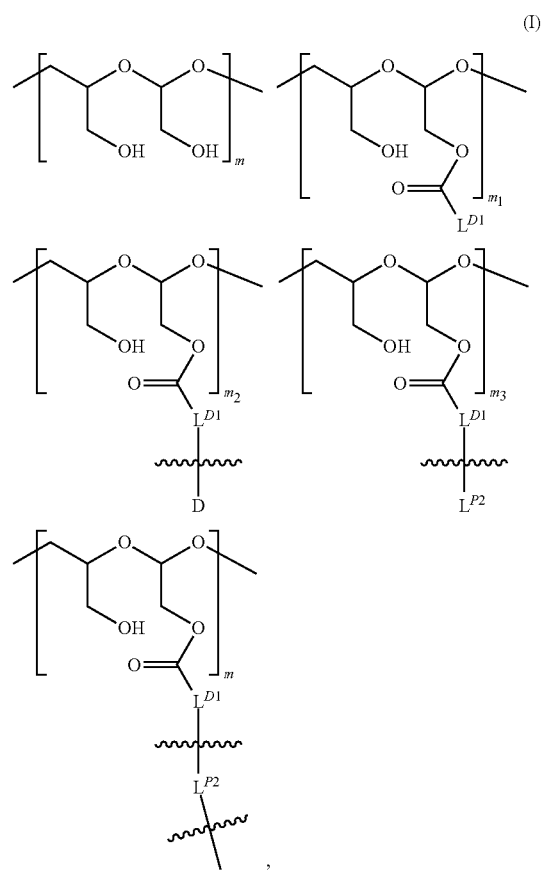

wherein:

$L^{D1}$ is a carbonyl-containing moiety;

each occurrence

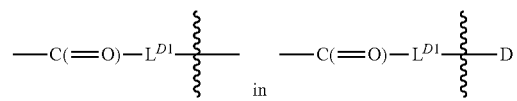

is independently a first linker that contains a biodegradable bond so that when the bond is broken, D is released in an active form for its intended therapeutic effect; and the

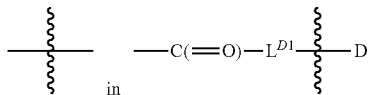

between $L^{D1}$ and D denotes direct or indirect attachment of D to $L^{D1}$;

each occurrence of

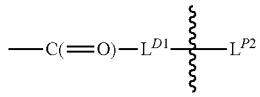

is independently a second linker not yet connected to the isolated antibody, in which $L^{P2}$ is a moiety containing a functional group that is yet to form a covalent bond with a functional group of the isolated antibody and the

between $L^{D1}$ and $L^{P2}$ denotes direct or indirect attachment of $L^{P2}$ to $L^{D1}$, and each occurrence of the second linker is distinct from each occurrence of the first linker;

each occurrence of

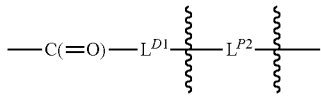

is independently a third linker that connects each D-carrying polymeric scaffold to the isolated antibody in which the terminal

attached to $L^{P2}$ denotes direct or indirect attachment of $L^{P2}$ to the isolated antibody upon formation of a covalent bond between a functional group of $L^{P2}$ and a functional group of the isolated antibody; and each occurrence of the third linker is distinct from each occurrence of the first linker;

m is an integer from 1 to about 300,
$m_1$ is an integer from 1 to about 140,
$m_2$ is an integer from 1 to about 40,
$m_3$ is an integer from 0 to about 18,
$m_4$ is an integer from 1 to about 10;
the sum of m, $m_1$, $m_2$, $m_3$, and $m_4$ ranges from about 15 to about 300; and
the total number of $L^{P2}$ connected to the isolated antibody is 10 or less.

The conjugate described herein can include one or more of the following features: For example, in Formula (I), $m_1$ is an integer from 1 to about 120 (e.g., about 1-90) and/or $m_3$ is an integer from 1 to about 10 (e.g., about 1-8).

For example, when the PHF in Formula (I) has a molecular weight ranging from about 6 kDa to about 20 kDa (i.e., the sum of m, $m_1$, $m_2$, $m_3$, and $m_4$ ranging from about 45 to about 150), $m_2$ is an integer from 2 to about 20, $m_3$ is an integer from 0 to about 9, $m_4$ is an integer from 1 to about 10, and/or $m_1$ is an integer from 1 to about 75 (e.g., $m_1$ being about 4-45).

For example, when the PHF in Formula (I) has a molecular weight ranging from about 8 kDa to about 15 kDa (i.e., the sum of m, $m_1$, $m_2$, $m_3$, and $m_4$ ranging from about 60 to about 110), $m_2$ is an integer from 2 to about 15, $m_3$ is an integer from 0 to about 7, $m_4$ is an integer from 1 to about 10, and/or $m_1$ is an integer from 1 to about 55 (e.g., $m_1$ being about 4-30).

For example, when the PHF in Formula (I) has a molecular weight ranging from about 2 kDa to about 20 kDa (i.e., the sum of m, $m_1$, $m_2$, $m_3$, and $m_4$ ranging from about 15 to about 150), $m_2$ is an integer from 1 to about 20, $m_3$ is an integer from 0 to about 10 (e.g., $m_3$ ranging from 0 to about 9), $m_4$ is an integer from 1 to about 8, and/or $m_1$ is an integer from 1 to about 70, and the total number of $L^{P2}$ connected to the isolated antibody ranges from about 2 to about 8 (e.g., about 2, 3, 4, 5, 6, 7, or 8).

For example, total number of $L^{P2}$ connected to the isolated antibody ranges from about 2 to about 6 (e.g., about 2, 3, 4, 5 or 6).

For example, total number of $L^{P2}$ connected to the isolated antibody ranges from about 3 to about 6 (e.g., about 3, 4, 5 or 6).

For example, total number of $L^{P2}$ connected to the isolated antibody ranges from about 3 to about 5 (e.g., about 3, 4, or 5).

For example, total number of $L^{P2}$ connected to the isolated antibody ranges from about 2 to about 4 (e.g., about 2, 3 or 4).

For example, total number of $L^{P2}$ connected to the isolated antibody ranges from about 3 to about 4 (e.g., about 3 or 4).

For example, when the PHF in Formula (I) has a molecular weight ranging from about 3 kDa to about 15 kDa (i.e., the sum of m, $m_1$, $m_2$, $m_3$, and $m_4$ ranging from about 20 to about 110), $m_2$ is an integer from 2 to about 15, $m_3$ is an integer from 0 to about 8 (e.g., $m_3$ ranging from 0 to about 7), $m_4$ is an integer from 1 to about 8, and/or $m_1$ is an integer from 2 to about 50, and the total number of $L^{P2}$ connected to the isolated antibody ranges from about 2 to about 8 (e.g., about 2, 3, 4, 5, 6, 7, or 8).

For example, when the PHF in Formula (I) has a molecular weight ranging from about 5 kDa to about 10 kDa, (i.e., the sum of m, $m_1$, $m_2$, $m_3$ and $m_4$ ranges from about 40 to about 75), $m_2$ is an integer from about 2 to about 10 (e.g., $m_2$ being about 3-10), $m_3$ is an integer from 0 to about 5 (e.g., $m_3$ ranging from 0 to about 4), $m_4$ is an integer from 1 to about 8 (e.g., $m_4$ ranging from 1 to about 5), and/or $m_1$ is an integer from about 2 to about 35 (e.g., $m_1$ being about 5-35), and the total number of $L^{P2}$ connected to the isolated antibody ranges from about 2 to about 8 (e.g., about 2, 3, 4, 5, 6, 7, or 8).

For example, each occurrence of D independently is a therapeutic agent, e.g., having a molecular weight of ≤5 kDa.

For example, each occurrence of D independently is a diagnostic agent or a label.

For example, some occurrences of D independently are therapeutic agents (e.g., having a molecular weight of ≤5 kDa) and the other occurrences of D are diagnostic agents or labels.

For example, each occurrence of D independently is an anti-cancer drug, for example, selected from vinca alkaloids, auristatins, tubulysins, duocarmycins, non-natural camptothecin compounds, maytansinoids, calicheamicin compounds, topoisomerase inhibitors, pyrrolobenzodiazepines, DNA binding drugs, DNA-alkylating drugs, RNA polymerase inhibitors, kinase inhibitors, MEK inhibitors, KSP inhibitors, and analogs thereof.

For example, each occurrence of the auristatin compound is auristatin, dolastatin (e.g., dolastatin 10 or dolastatin 15), monomethylauristatin E (MMAE), monomethylauristatin F (MMAF), auristatin F hydroxypropyl amide (AF HPA), monomethylauristatin F hydroxypropyl amide (AF HPA), or auristatin F phenylenediamine (AFP).

For example, each occurrence of the duocarmycin or analog thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

For example, each occurrence of the camptothecin compound is camptothecin, CPT-11 (irinotecan), SN-38, or topotecan.

For example, each occurrence of the pyrrolobenzodiazepine compound is a pyrrolobenzodiazepine monomer, a symmetrical pyrrolobenzodiazepine dimer or an unsymmetrical pyrrolobenzodiazepine dimer.

For example, each

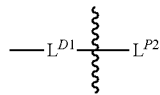

when not connected to the isolated antibody, independently comprises a terminal group $W^P$, in which each $W^P$ independently is:

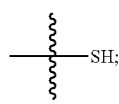

(1)

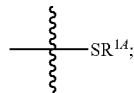

(2)

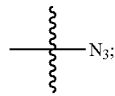

(3)

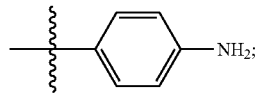

(4)

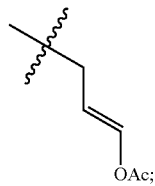

(5)

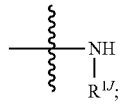

(6)

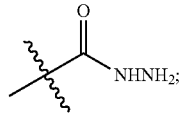

(7)

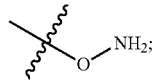

(8)

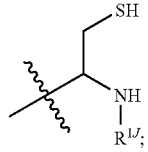

(9)

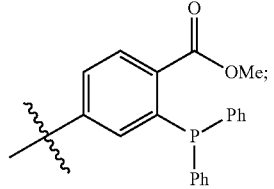

(10)

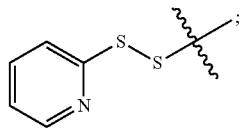

(11)

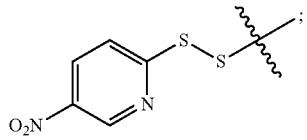

(12)

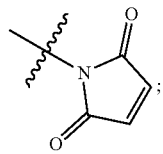

(13)

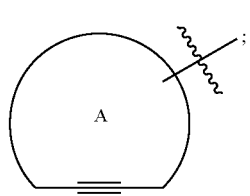

(14)

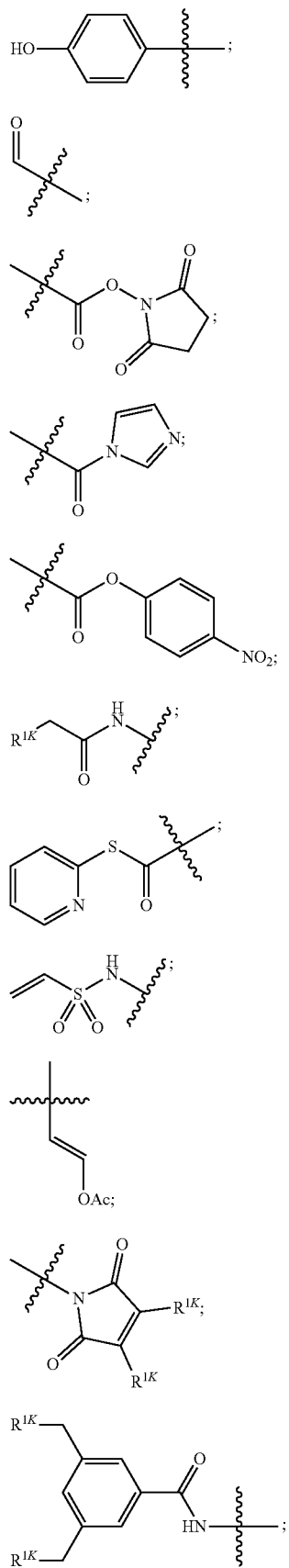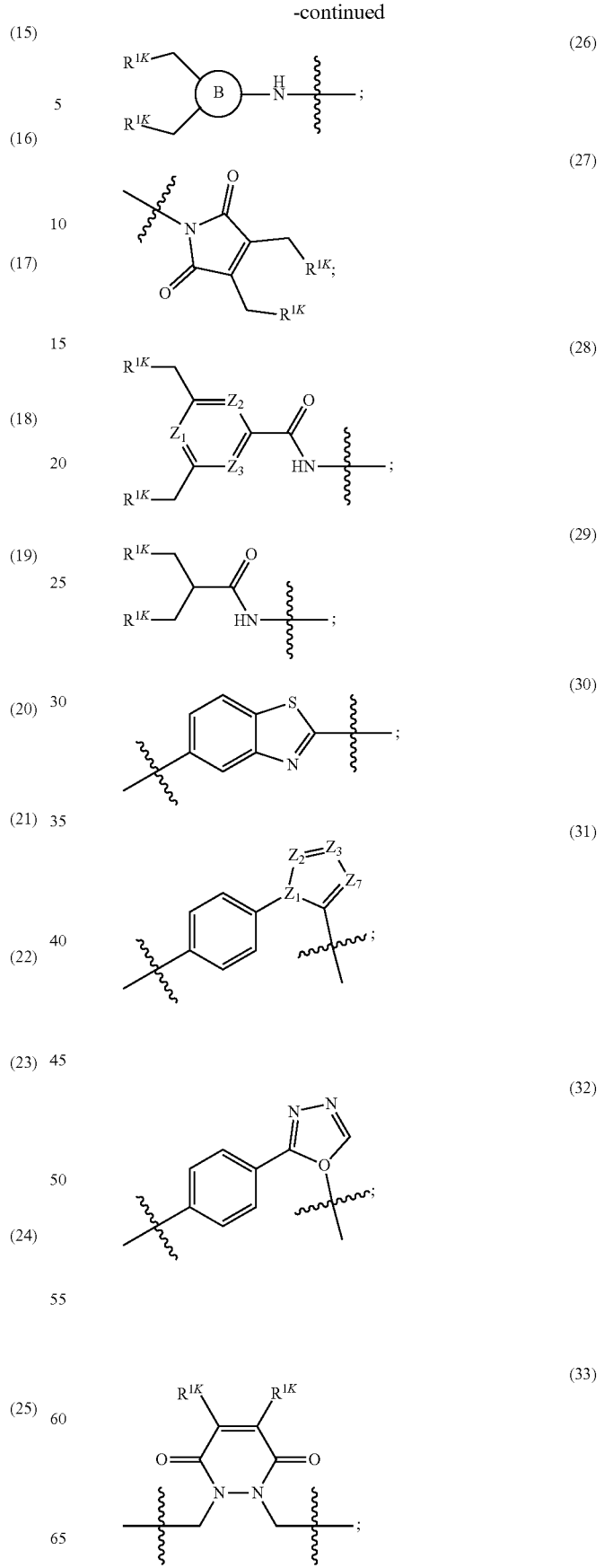

(34) 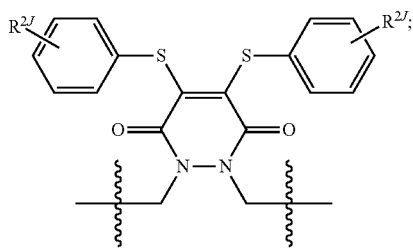

(35) 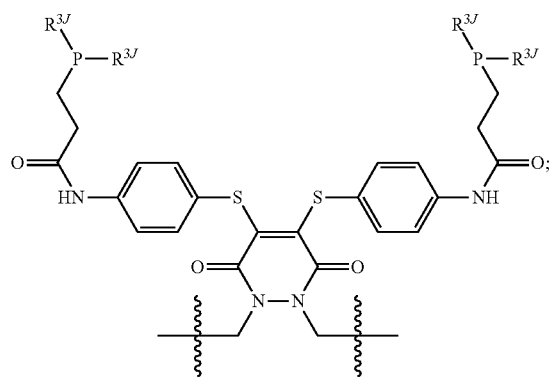

(36) 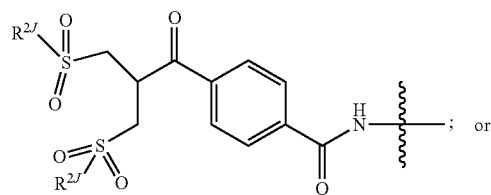

(37) 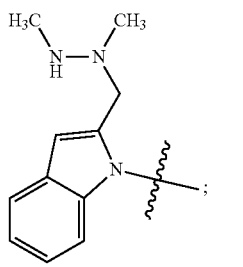

(38) 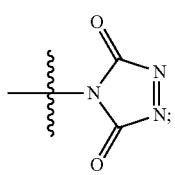

(39) 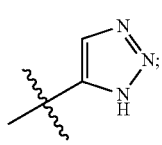

(40) 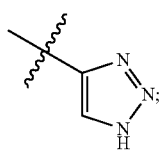

(41) 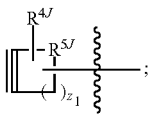

(43) 

wherein
ring A is cycloalkyl or heterocycloalkyl;
ring B is cycloalkyl, heterocycloalkyl, aryl, or heteroaryl;
$R^{1K}$ is a leaving group;
$R^{1A}$ is a sulfur protecting group;
$R^{1J}$ is hydrogen, an aliphatic, heteroaliphatic, carbocyclic, or heterocycloalkyl moiety;
$R^{2J}$ is hydrogen, an aliphatic, aryl, heteroaliphatic, or carbocyclic moiety;
$R^{3J}$ is $C_{1-6}$ alkyl and each of $Z_1$, $Z_2$, $Z_3$ and $Z_7$ is independently a carbon or nitrogen atom;
$R^4$ is hydrogen, halogen, OR, —$NO_2$, —CN, —$S(O)_2R$, $C_{1-24}$ alkyl (e.g., $C_{1-6}$ alkyl), or 6-24 membered aryl or heteroaryl, wherein the $C_{1-24}$ alkyl (e.g., $C_{1-6}$ alkyl), or 6-24 membered aryl or heteroaryl, is optionally substituted with one or more aryl or heteroaryl; or two $R^{4j}$ together form an annelated cycloalkyl, heterocycloalkyl, aryl, or heteroaryl; R is hydrogen, alkyl, heteroalkyl, cycloalkyl, or heterocycloalkyl;
$R^{5j}$ is $C(R^{4j})_2$, O, S or NR; and
$z_1$ is an integer 1, 2, 3, 4, 5, 6, 7, 8, 9 or 10.

For example, each $R^{1A}$ independently is

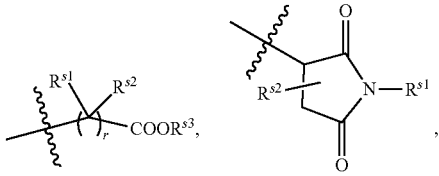

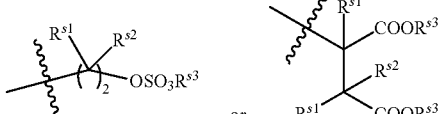

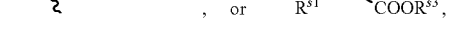

in which r is 1 or 2 and each of $R^{s1}$, $R^{s2}$, and $R^{s3}$ is hydrogen, an aliphatic, heteroaliphatic, carbocyclic, or heterocycloalkyl moiety.

For example, ring A can be

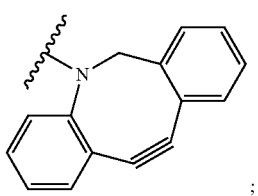 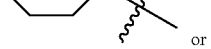 or

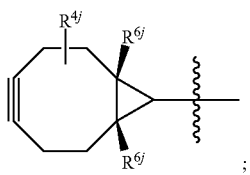

wherein R⁶ is hydrogen, halogen, $C_{1-24}$ alkyl (e.g., $C_{1-6}$ alkyl), or 6-24 membered aryl or heteroaryl, wherein the $C_{1-24}$ alkyl (e.g., $C_{1-6}$ alkyl), or 6-24 membered aryl or heteroaryl, is optionally substituted with one or more aryl or heteroaryl.

For example, ring A can be

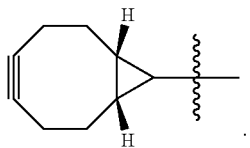 [SMILES: *C1[C@H]2CCC#CCC[C@@H]12]

For example, the functional group of $L^{P2}$ that is yet to form a covalent bond with a functional group of the isolated antibody (such as a functional group or a reactive moiety on an amino acid residue of the antibody, for example, a functional group on a cysteine residue or a lysine residue of the antibody), is selected from $—SR^P$, $—S—S-LG$,

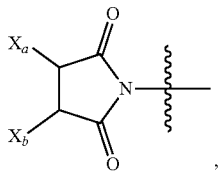

and halo, in which LG is a leaving group, $R^P$ is H or a sulfur protecting group, and one of $X_a$ and $X_b$ is H and the other is a water-soluble maleimido blocking moiety, or $X_a$ and $X_b$, together with the carbon atoms to which they are attached for a carbon-carbon double bond. For example, the functional group of $L^{P2}$ that is yet to form a covalent bond is a functional group that is not reacted with a functional group of the isolated antibody, e.g.,

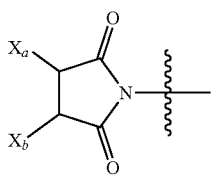

as the functional group of $L^{P2}$, in which one of $X_a$ and $X_b$ is H and the other is a water-soluble maleimido blocking moiety, or $X_a$ and $X_b$.

For example, $L^{D1}$ comprises $—X—(CH_2)_v—C(=O)—$ with X directly connected to the carbonyl group of

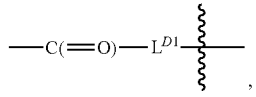

in which X is $CH_2$, O, or NH, and v is an integer from 1 to 6.

For example, each occurrence of

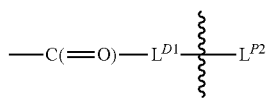

is independently $—C(=O)—X—(CH_2)_v—C(=O)—NH—(CH_2)_u—NH—C(=O)—(CH_2)_w—(OCH_2)_x—)—(CH_2)—(CH_2)_y$-M, in which X is $CH_2$, O, or NH, each of v, u, w, x and y independently is an integer from 1 to 6, and M is

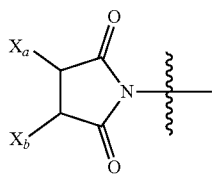

wherein one of $X_a$ and $X_b$ is H and the other is a water-soluble maleimido blocking moiety, or $X_a$ and $X_b$, together with the carbon atoms to which they are attached for a carbon-carbon double bond.

For example, each of v, u, w, x and y is 2.

For example, the ratio between D and the isolated NaPi2b-targeted antibody, XMT-1535, is about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6; 1, 5:1, 4:1, 3:1, 2:1 or 1:1.

For example, the ratio between D and the isolated NaPi2b-targeted antibody, XMT-1535, is about 20:1, 15:1, 10:1, 5:1, 2:1 or 1:1.

For example, the ratio between D and the isolated NaPi2b-targeted antibody, XMT-1535, is about 16:1, 15:1, 14:1, 13:1, 12:1, 11:1 or 10:1.

For example, the ratio between D and the isolated NaPi2b-targeted antibody, XMT-1535, is about 15:1, 14:1, 13:1, 12:1 or 11:1.

For example, the ratio between D and the isolated NaPi2b-targeted antibody, XMT-1535, is about 15:1, 14:1, 13:1 or 12:1.

For example, the ratio between D and the isolated NaPi2b-targeted antibody, XMT-1535, is about 14:1, 13:1 or 12:1.

For example, the ratio between D and the isolated NaPi2b-targeted antibody, XMT-1535, is about 13:1 or 12:1.

For example, the ratio between D and the isolated NaPi2b-targeted antibody, XMT-1535, is about 12:1.

For example, the ratio between D and the isolated NaPi2b-targeted antibody, XMT-1535, is about 14:1, 13:1, 12:1, 11:1, 10:1 or 9:1.

For example, the ratio between D and the isolated NaPi2b-targeted antibody, XMT-1535, is about 13:1, 12:1, 11:1, 10:1 or 9:1.

For example, the ratio between D and the isolated NaPi2b-targeted antibody, XMT-1535, is about 12:1, 11:1, 10:1 or 9:1.

For example, the ratio between D and the isolated NaPi2b-targeted antibody, XMT-1535, is about 11:1, 10:1 or 9:1.

For example, each of the one or more D-carrying polymeric scaffolds independently is of Formula (II):

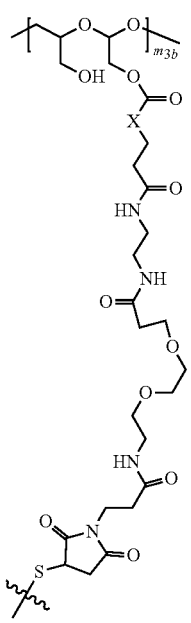

(II)

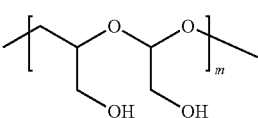

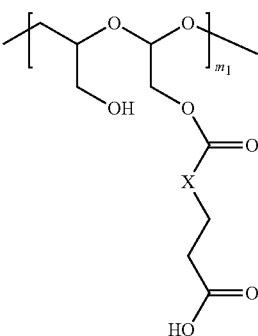

-continued

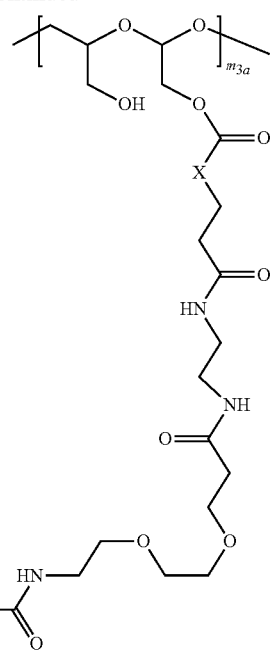

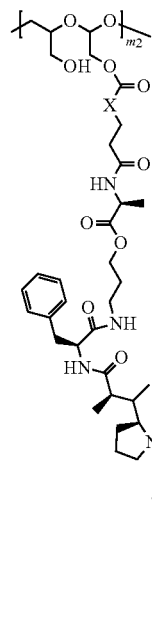

wherein
  $m_{3a}$ is an integer from 0 to about 17,
  $m_{3b}$ is an integer from 1 to about 8, and
  the terminal

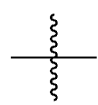

denotes the direct attachment of the one or more polymeric scaffolds to the isolated NaPi2b-targeted antibody, XMT-1535. The scaffold of Formula (II) can include one or more of the following features:

The sum of $m_{3a}$ and $m_{3b}$ is between 1 and 18.

When the PHF in Formula (II) has a molecular weight ranging from about 2 kDa to about 40 kDa, the sum of m, $m_1$, $m_2$, $m_{3a}$ and $m_{3b}$ ranges from about 15 to about 300, $m_1$ is an integer from 1 to about 140, $m_2$ is an integer from 1 to about 40, $m_{3a}$ is an integer from 0 to about 17, $m_{3b}$ is an integer from 1 to about 8, the sum of $m_{3a}$ and $m_{3b}$ ranges from 1 and about 18, and the ratio between the PHF and the isolated NaPi2b-targeted antibody, XMT-1535, is 10 or less.

When the PHF in Formula (II) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8, the sum of $m_{3a}$ and $m_{3b}$ ranges from 1 and about 10, and the ratio between the PHF and the isolated NaPi2b-targeted antibody, XMT-1535, is an integer from 2 to about 8 (e.g., from about 2 to about 6 or from about 2 to about 4).

When the PHF in Formula (II) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8, the sum of $m_{3a}$ and $m_{3b}$ ranges from 1 and about 8; and the ratio between the PHF and the isolated NaPi2b-targeted antibody, XMT-1535, is an integer from 2 to about 8 (e.g., from about 2 to about 6 or from about 2 to about 4).

When the PHF in Formula (II) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of $m_{3a}$ and $m_{3b}$ ranges from 1 and about 5; and the ratio between the PHF and the isolated NaPi2b-targeted antibody, XMT-1535, is an integer from 2 to about 8 (e.g., from about 2 to about 6 or from about 2 to about 4).

In certain embodiments, the ratio between auristatin F hydroxypropyl amide ("AF HPA") and the isolated NaPi2b-targeted antibody, XMT-1535, can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In certain embodiments, the ratio between AF HPA and the isolated NaPi2b-targeted antibody, XMT-1535, can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and the isolated NaPi2b-targeted antibody, XMT-1535, can be about 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and isolated NaPi2b-targeted antibody can be about 16:1, 15:1, 14:1, 13:1, 12:1, 11:1 or 10:1.

In some embodiments, the ratio between AF HPA and isolated NaPi2b-targeted antibody can be about 15:1, 14:1, 13:1, 12:1 or 11:1.

In some embodiments, the ratio between AF HPA and isolated NaPi2b-targeted antibody can be about 15:1, 14:1, 13:1 or 12:1.

In some embodiments, the ratio between AF HPA and isolated NaPi2b-targeted antibody can be about 14:1, 13:1 or 12:1.

In some embodiments, the ratio between AF HPA and isolated NaPi2b-targeted antibody can be about 13:1 or 12:1.

In some embodiments, the ratio between AF HPA and isolated NaPi2b-targeted antibody can be about 12:1.

In some embodiments, the ratio between AF HPA and isolated NaPi2b-targeted antibody can be about 14:1, 13:1, 12:1, 11:1, 10:1 or 9:1.

In some embodiments, the ratio between AF HPA and isolated NaPi2b-targeted antibody can be about 13:1, 12:1, 11:1, 10:1 or 9:1.

In some embodiments, the ratio between AF HPA and isolated NaPi2b-targeted antibody can be about 12:1, 11:1, 10:1 or 9:1.

In some embodiments, the ratio between AF HPA and isolated NaPi2b-targeted antibody can be about 11:1, 10:1 or 9:1.

In certain embodiments, the ratio between PHF and isolated NaPi2b-targeted antibody can be about 10:1, 9:1, 8:1, 7:1, 6:1, 5:1, 4:1, 3:1, 2:1 or 1:1.

In certain embodiments, the ratio between PHF and isolated NaPi2b-targeted antibody can be about 8:1, 7:1, 6:1, 5:1, 4:1, 3:1 or 2:1.

In other embodiments, the ratio between PHF and isolated NaPi2b-targeted antibody can be about 6:1, 5:1, 4:1, 3:1, 2:1 or 1:1.

In other embodiments, the ratio between PHF and isolated NaPi2b-targeted antibody can be about 6:1, 5:1, 4:1, 3:1 or 2:1.

In other embodiments, the ratio between PHF and isolated NaPi2b-targeted antibody can be about 6:1, 5:1, 4:1 or 3:1.

In some embodiments, the ratio between PHF and isolated NaPi2b-targeted antibody can be about 5:1, 4:1 or 3:1.

In some embodiments, the ratio between PHF and isolated NaPi2b-targeted antibody can be about 4:1, 3:1 or 2:1.

In some embodiments, the ratio between PHF and isolated NaPi2b-targeted antibody can be about 4:1 or 3:1.

The water-soluble maleimido blocking moieties (e.g., $X_a$ or $X_b$) are moieties that can be covalently attached to one of the two olefin carbon atoms upon reaction of the maleimido group with a thiol-containing compound of Formula (II):

$$R_{90}-(CH_2)_d-SH \qquad (II)$$

wherein:

$R_{90}$ is $NHR_{91}$, OH, $COOR_{93}$, $CH(NHR_{91})COOR_{93}$ or a substituted phenyl group;

$R_{93}$ is hydrogen or $C_{1-4}$ alkyl;

$R_{91}$ is hydrogen, $CH_3$ or $CH_3CO$ and d is an integer from 1 to 3.

In one embodiment, the water-soluble maleimido blocking compound of Formula (II) can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, $PO_3H$, and the like.

In another aspect, the water-soluble maleimido blocking group is $-S-(CH_2)_d-R_{90}$, in which, $R_{90}$ is OH, COOH, or $CH(NHR_{91})COOR_{93}$;

$R_{93}$ is hydrogen or $CH_3$;

$R_{91}$ is hydrogen or $CH_3CO$; and d is 1 or 2.

In another embodiment, the water-soluble maleimido blocking group is —S—CH$_2$—CH(NH$_2$)COOH.

In certain embodiments, the conjugate described herein comprises one or more D-carrying PHF, each of which independently is of Formula (III), wherein the PHF has a molecular weight ranging from about 2 kDa to about 40 kDa:

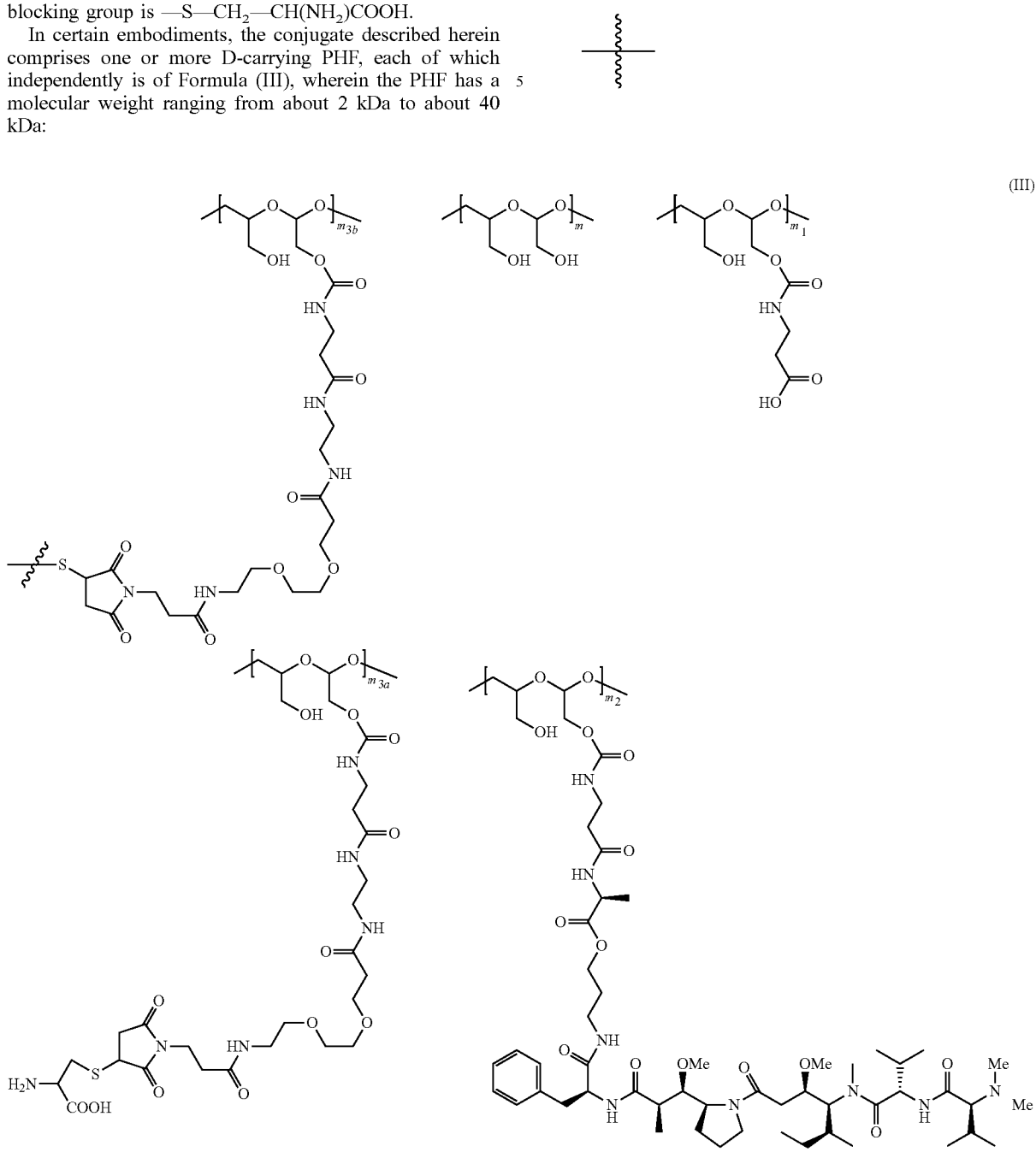

wherein:

m is an integer from 1 to about 300, m$_1$ is an integer from 1 to about 140, m$_2$ is an integer from 1 to about 40, m$_{3a}$ is an integer from 0 to about 17, m$_{3b}$ is an integer from 1 to about 8;

the sum of m$_{3a}$ and m$_{3b}$ ranges from 1 and about 18;

the sum of m, m$_1$, m$_2$, m$_{3a}$, and m$_{3b}$ ranges from about 15 to about 300;

the terminal denotes the attachment of one or more PHF polymeric scaffolds to the isolated NaPi2b-targeted antibody, XMT-1535, the ratio between the PHF and the antibody is 10 or less.

The scaffold of Formula (III) can include one or more of the following features:

When the PHF in Formula (III) has a molecular weight ranging from about 2 kDa to about 20 kDa, the sum of m, m$_1$, m$_2$, m$_{3a}$ and m$_{3b}$ ranges from about 15 to about 150, m$_1$ is an integer from 1 to about 70, m$_2$ is an integer from 1 to about 20, m$_{3a}$ is an integer from 0 to about 9, m$_{3b}$ is an integer from 1 to about 8, the sum of m$_{3a}$ and m$_{3b}$ ranges from 1 and about 10, and the ratio between the PHF and the antibody is an integer from 2 to about 8.

When the PHF in Formula (III) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8, the sum of $m_{3a}$ and $m_{3b}$ ranges from 1 and about 8; and the ratio between the PHF and the antibody is an integer from 2 to about 8 (e.g., from about 2 to about 6 or from about 2 to about 4).

When the PHF in Formula (III) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of $m_{3a}$ and $m_{3b}$ ranges from 1 and about 5; and the ratio between the PHF and the antibody is an integer from 2 to about 8 (e.g., from about 2 to about 6 or from about 2 to about 4).

In certain embodiments, the ratio between auristatin F hydroxypropyl amide ("AF HPA") and the antibody can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In certain embodiments, the ratio between AF HPA and the antibody can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and the antibody can be about 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and the antibody can be about 16:1, 15:1, 14:1, 13:1, 12:1, 11:1 or 10:1.

In some embodiments, the ratio between AF HPA and the antibody can be about 15:1, 14:1, 13:1, 12:1 or 11:1.

In some embodiments, the ratio between AF HPA and the antibody can be about 15:1, 14:1, 13:1 or 12:1.

In some embodiments, the ratio between AF HPA and the antibody can be about 14:1, 13:1 or 12:1.

In some embodiments, the ratio between AF HPA and the antibody can be about 13:1 or 12:1.

In some embodiments, the ratio between AF HPA and the antibody can be about 12:1.

In some embodiments, the ratio between AF HPA and the antibody can be about 14:1, 13:1, 12:1, 11:1, 10:1 or 9:1.

In some embodiments, the ratio between AF HPA and the antibody can be about 13:1, 12:1, 11:1, 10:1 or 9:1.

In some embodiments, the ratio between AF HPA and the antibody can be about 12:1, In certain embodiments, the ratio between PHF and the antibody can be about 10:1, 9:1, 8:1, 7:1, 6:1, 5:1, 4:1, 3:1, 2:1 or 1:1.

In certain embodiments, the ratio between PHF and the antibody can be about 8:1, 7:1, 6:1, 5:1, 4:1, 3:1 or 2:1.

In other embodiments, the ratio between PHF and the antibody can be about 6:1, 5:1, 4:1, 3:1, 2:1 or 1:1.

In other embodiments, the ratio between PHF and the antibody can be about 6:1, 5:1, 4:1, 3:1 or 2:1.

In other embodiments, the ratio between PHF and the antibody can be about 6:1, 5:1, 4:1 or 3:1.

In some embodiments, the ratio between PHF and the antibody can be about 5:1, 4:1 or 3:1.

In some embodiments, the ratio between PHF and the antibody can be about 4:1, 3:1 or 2:1.

In some embodiments, the ratio between PHF and the antibody can be about 4:1 or 3:1.

In certain embodiments, in the conjugate described herein, the D-carrying polymeric scaffold of Formula (III) is of Formula (IV), wherein the polymer is PHF that has a molecular weight ranging from about 5 kDa to about 10 kDa:

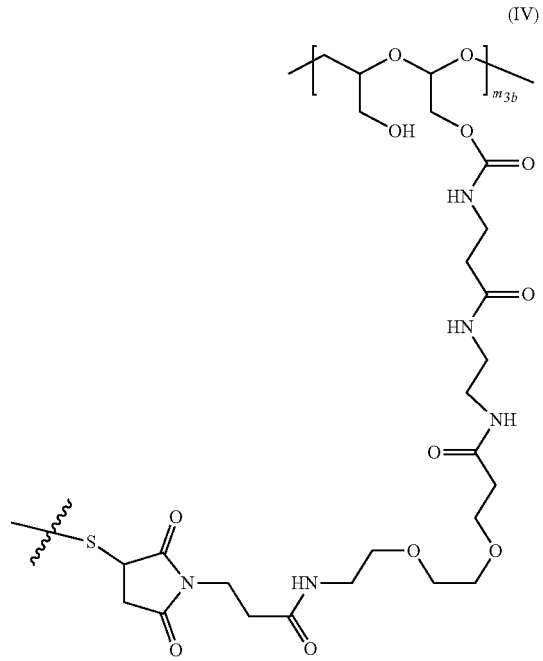

(IV)

-continued
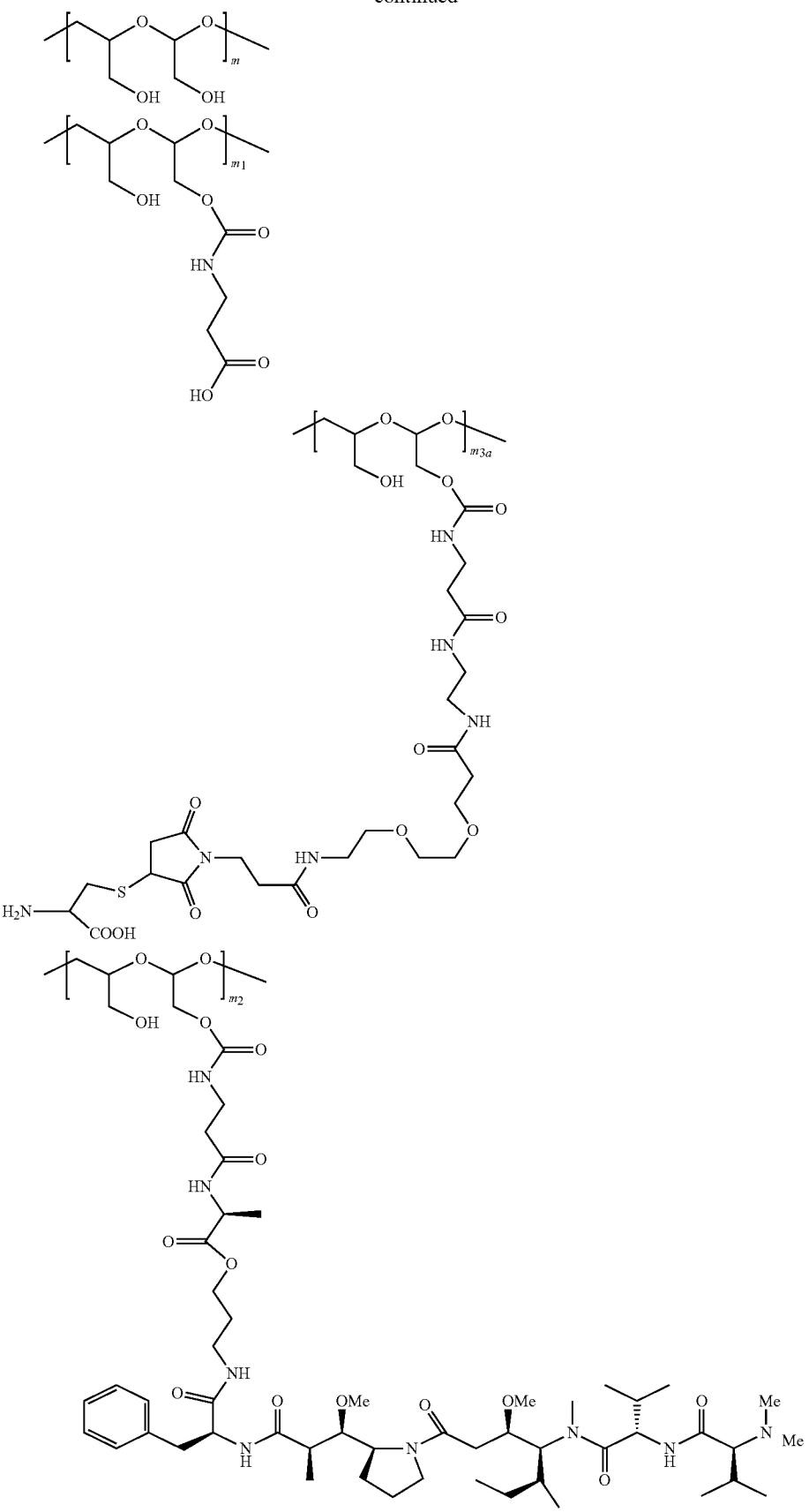

wherein:
m is an integer from 30 to about 35,
$m_1$ is an integer from 8 to about 10,
$m_2$ is an integer from 2 to about 5,
$m_{3a}$ is an integer from 0 to about 1,
$m_{3b}$ is an integer from 1 to about 2;
the sum of $m_{3a}$ and $m_{3b}$ ranges from 1 and about 4;
the terminal

denotes the attachment of one or more PHF polymeric scaffolds to the isolated NaPi2b-targeted antibody, XMT-1535,
the ratio between the PHF and the antibody is about 3 to about 5.

Diagnostic, Predictive, and Prognostic Methods of the Invention

In various aspect the invention provides a method for identifying a cancer patient amenable to NaiPi2b targeted therapy by measuring the status NaPi2b expression in a tumor sample obtained from the patient, and identifying the patient for treatment based on the expression of NaPi2b in the tumor sample.

Specifically the invention provides methods of discriminating between cancer patients that will respond to NaPi2b-targeted, e.g. treatment with the NaPi2b-targeted polymer antibody-drug conjugate disclosed in WO2017/160754 from those that will not respond based upon the expression levels of NaPi2b. The NaPi2b expression profile correlates with (and so are able to discriminate between) patients with good or poor response to treatment.

In other embodiments, the invention includes a method to compare NaPi2b expression in a sample of cancer cells from a patient to a control NaPi2b profile to determine the likely clinical or treatment outcome for the patient, or natural biological result. These embodiments of the invention may be advantageously used to meet an important unmet diagnostic need for the ability to predict whether a patient will likely benefit from a given treatment type or whether a patient will be better off with another type of treatment. For example, a high NaPi2b expression level value might be strongly associated with response to NaPi2b-targeted polymer antibody-drug conjugates disclosed in WO 2017/160574.

The methods of the invention provides objective protein expression patterns, which may be used alone or in combination with subjective criteria to provide a more accurate assessment of patient outcomes, including survival and the recurrence of cancer.

In various aspects the invention provided method for identifying and/or treating a diseases or disorders related to aberrant NaPi2b expression by measuring NaPi2b expression in a tumor sample obtained from the patient.

The methods of the invention provides objective protein expression patterns, which may be used alone or in combination with subjective criteria to provide a more accurate diagnosis of NSCLC. For example, the invention provides methods diagnosing NSCLC in a patient by measuring NaPi2b expression in a tumor sample obtained from the patient. Specifically, the invention provides methods for subtyping a NSCLC by measuring NaPi2b expression in tumor sample obtained from the patient and identifying the NSCLC as being adenocarcinoma based on NaPi2b expression in the tumor sample. Optionally, the expression levels of one or more of TTF-1, Napsin A, p63, p40 or CH5/6 are further determined.

The cancer patient has a disease or disorders related to aberrant NaPi2b activity and/or expression. Diseases or disorders related to aberrant NaPi2b activity and/or expression include but not limited to cancer. The cancer can be ovarian cancer such as epithelial ovarian cancer, thyroid cancer, colorectal cancer, lung cancer, non-small cell lung cancer (NSCLC) such as non-squamous NSCLC, breast cancer, kidney cancer, salivary duct carcinoma, papillary thyroid cancer, papillary renal cancer, salivary duct adenocarcinoma, endometrial cancer, and cholangiocarcinoma.

The subject is refractory to chemotherapy, including standard, front-line chemotherapeutic agents. In some embodiments, the subject has platinum-sensitive ovarian cancer. In some embodiments, the subject has platinum-refractory ovarian cancer. In some embodiments, the subject has advanced ovarian cancer and has not received any prior therapy for treating cancer (e.g., ovarian cancer). In some embodiments, the subject has advanced ovarian cancer and has not received any prior chemotherapy for treating cancer (e.g., ovarian cancer).

The sample is derived from a subject having or suspected of having cancer. The sample of cancer cells is dissected from tissue removed or obtained from the subject.

In some embodiments, the test cell population is derived from fresh, unfrozen tissue from a biopsy sample. In other embodiments, the test cell population is derived from a primary or metastatic site. In some embodiments, the test cell population is derived from a fresh or frozen tissue from a biopsy or surgical sample or ascetic fluid or pleural fluid. In some embodiments, the test cell population is derived from a fixed tissue (e.g., formalin fixation or formalin-fixed paraffin-embedded (FFPE)) from a biopsy or surgical sample or cell block derived from a fluid specimen. The tissue sample may be frozen or fresh.

NaPi2b targeted therapy includes NaPi2b-targeted antibody drug conjugate (ADC) therapy. For example, such NaPi2b-targeted antibody drug conjugate (ADC) therapy as described in WO 2017/160754.

The requisite level of NaPi2b expression may be that which is identified by the any methods known in the art and more specifically by the methods described herein.

For example, the level of NaPi2b expression can be measured by conducting a known immunological assay, such as an enzyme immunoassay, radioimmunoassay, competitive immunoassay, double antibody sandwich assay, fluoroimmunoassay, ELISA, Western blotting technique, agglutination assay, cytofluorometry (e.g. flow cytometry), or immunohistochemical staining assay, using an antibody that specifically recognizes NaPi2b (e.g., the chimeric antibodies according to the invention). Cell-based assays, such flow cytometry (FC), immuno-histochemistry (IHC), or immunofluorescence (IF) are particularly desirable in practicing the methods of the invention, since such assay formats are clinically-suitable. Accordingly, in some embodiment, the methods of the invention are implemented in a flow-cytometry (FC), immuno-histochemistry (IHC), or immunofluorescence (IF) assay format. Preferably, the methods are implemented in an IHC format Flow cytometry (FC) may be employed to determine cell surface expression of NaPi2b in a tumor sample before, during, and after treatment with a drug targeted at inhibiting NaPi2b expression. For example, tumor cells may be analyzed by flow cytometry for NaPi2b, as well as for markers identifying cancer cell types, etc., if so desired. Flow cytometry may be carried out according to standard methods. See, e.g. Chow et al., Cytometry (Communications in Clinical Cytometry) 46: 72-78 (2001). Briefly and by way of example, the following protocol for cytometric analysis may be employed: fixation of the cells with 2% paraformaldehyde for 10 minutes at 37.° C. followed by permeabilization in 90% methanol for 30 minutes on ice. Cells may then be stained with NaPi2b-specific antibody, washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed NaPi2b in the tumor.

Immunohistochemical (IHC) staining may be also employed to determine the expression of NaPi2b in a tumor sample before, during, and after treatment with a drug targeted at inhibiting activity. IHC may be carried out according to well-known techniques. See, e.g., ANTIBODIES; A LABORATORY MANUAL, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary polypeptide antibody and secondary antibody; and finally detecting using ABC avidin/biotin method according to manufacturer's instructions.

Immunofluorescence (IF) assays may be also employed to determine the expression of NaPi2b tumor sample before, during, and after treatment with a drug targeted at inhibiting activity. IF may be carried out according to well-known techniques. See, e.g., J. M. Polak and S. Van Noorden (1997) INTRODUCTION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with the primary antibody against polypeptide followed by a secondary antibody labeled with a fluorescent dye such as Alexa 488 and analyzed with an epifluorescent microscope.

Antibodies employed in the above-described assays may be advantageously conjugated to fluorescent dyes (e.g. Alexa488, PE), or other labels, such as quantum dots, for use in multi-parametric analyses along with other signal transduction (phospho-AKT, phospho-Erk 1/2) and/or cell marker (cytokeratin) antibodies.

In a preferred embodiment the expression of NaPi2b in a sample from a tumor is determined immunohistochemically. In even a more preferred embodiment, the expression of NaPi2b in a sample from a tumor is determined immunohistochemically (IHC) using the chimeric antibody described herein.

Alternatively, the assay may include preparing RNA from the sample, optionally for use in PCR (polymerase chain reaction) or other analytical methodology. The PCR methodology is optionally, for example, RT-PCR (reverse transcription-PCR) or quantitative PCR, such as, for example, real-time RT-PCR, RNAseq and the like. Alternatively, the assaying may be conducted by use of an array, such as a microarray as known in the relevant field.

Patients are identified as being responsive to treatment, wherein the treatment is monitored or cancer is detected by detecting and/or measuring the expression level of NaPi2b in a sample.

The detection/measurement of the expression level of NaPi2b is determined by calculating a NaPi2b score. The NaPi2b score is quantitative or semi quantitative. For example detection is scored pathologically to arrive at a pathology score. It is contemplated that any scoring methods known in the art may be used in the methods of the invention. In particular, any histological scoring methods known in the art.

The methods for assessing the measurement results obtained by immunohistochemical staining assays include, for example, the H-score method. The H-score is determined by the following calculation formula (Am J Clin Pathol. 1988; 90 (3): 233-9). H-Score=((% at <1+)×0)+((% at 1+)×1)+((% at 2+)×2)+((% at 3+)×3) where staining intensity 0 is unstained; staining intensity 1 is weak staining; staining intensity 2 is moderate staining; and staining intensity 3 is strong staining.

In some embodiments, the H-score can be a value of 0 to 300, and when the H-score is higher than a cut-off point, anti-tumor effects maybe observed in chemotherapy that uses the NaPi2b-targeted antibody drug conjugate of the present invention. For example, when the subject has an H-score of 50, 60, 70, 80, 90, 100, 110, 120, 130 or higher the subject is responsive to treatment with a NaPi2b-targeted antibody drug conjugate (ADC) as described herein and in WO 2017/160754

In assessment by the H-score method, only cancer cell portions are used. For negative or positive controls for staining intensity, formalin-fixed paraffin-embedded cell lines or xenografts (lines whose protein expression levels are known in advance) may be employed. When there are no control specimens, a plurality of specimens are assessed simultaneously to confirm the overall distribution of staining intensity of the specimens, and then staining intensity may be set.

In addition to the H-score method, other scoring methods, such as the Allred method (Harvey, et al. Journal of Clinical Oncology 17, no. 5 (May 1999) 1474-1474), can also be used. Cut-off points are required to be set in each method. Allred score=score of percentage of positive cells+staining intensity score. Specimens could also be scored semi-quantitatively as having a scoring of 1+ or 2+ or 3+ for NaPi2b expression.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic, predictive, or prognostic test, assay, or method concerns the ability of the test, assay, or method to distinguish between subjects responsive to chemotherapeutic treatment and those that are not, is based on whether the subjects have an "effective amount" or a "significant alteration" in the levels of NaPi2b. By "effective amount" or "significant alteration," it is meant that the measurement NaPi2b is different than the predetermined cut-off point (or threshold value) and therefore indicates that the subject responsiveness to therapy or disease free/overall survival for which the NaPi2b. is a determinant.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points.

Construction of Clinical Algorithms

Any formula may be used to combine NaPi2b results into indices useful in the practice of the invention. As indicated above, and without limitation, such indices may indicate, among the various other indications, the probability, likelihood, absolute or relative chance of responding to, for example, chemotherapy or chemoradiotherapy, i.e. NaPi2b-targeted therapy, e.g. treatment with the NaPi2b-targeted polymer antibody-drug conjugate described herein and disclosed in WO 2017/160754. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from NaPi2b. results in the relevant training population. Amongst other uses, such formula may be intended to map the feature space derived from one or more inputs to a set of subject classes (e.g. useful in predicting class membership of subjects as normal, responders and non-responders), to derive an estimation of a probability function of risk using a Bayesian approach (e.g. the risk of cancer or a metastatic event), or to estimate the class-conditional probabilities, then use Bayes' rule to produce the class probability function as in the previous case.

Methods of Treatment

Once selected for treatment the patient receives a therapeutically effective amount of a NaPi2b antibody conjugate (e.g. NaPi2b-targeted polymer antibody-drug conjugate described herein or disclosed in WO 2017/160754).

Accordingly, the present invention also provides methods of treating, preventing, delaying the progression of or otherwise ameliorating a symptom of a cancer selected from the group consisting of epithelial ovarian cancer, thyroid cancer, colorectal cancer, lung cancer, non-small cell lung cancer (NSCLC) such as non-squamous NSCLC, adenocarcinoma, breast cancer, kidney cancer, salivary duct carcinoma, papillary thyroid cancer, papillary renal cancer, salivary duct adenocarcinoma, endometrial cancer, and cholangiocarcinoma by administering a NaPi2b antibody conjugate (e.g., NaPi2b-targeted polymer antibody-drug conjugate described herein or disclosed in WO 2017/160753) to a subject identified by the methods described herein. The subject to be treated is, e.g., human. The conjugate is administered in an amount sufficient to treat, prevent or alleviate a symptom associated with the pathology.

By therapeutically effective amount relates generally to the amount needed to achieve a therapeutic objective. The amount required to be administered will furthermore depend on the binding affinity of the antibody for its specific antigen, and will also depend on the rate at which an administered antibody is depleted from the free volume other subject to which it is administered. The dosage regimen utilizing the conjugates disclosed herein is also selected in accordance with a variety of other factors including type, species, age, weight, sex and medical condition of the patient; the severity of the condition to be treated; the route of administration; the renal and hepatic function of the patient; and the particular conjugate employed. An ordinarily skilled physician or veterinarian can readily determine and prescribe the effective amount of the conjugate required to prevent, counter or arrest the progress of the condition.

Common ranges for therapeutically effective dosing of a NaPi2b antibody conjugate disclosed herein may be, by way of nonlimiting example, from about 0.1 mg/kg body weight to about 50 mg/kg body weight, from about 0.1 mg/kg body weight to about 100 mg/kg body weight or from about 0.1 mg/kg body weight to about 150 mg/kg body weight. Ranges disclosed herein are expressed as amount administered based on the subject's weight, and one skilled in the art can easily express it as amount administered per body surface area of the subject. For example, 1 mg/kg body weight for a human adult is equivalent to about 37 mg/m$^2$ and 1 mg/kg body weight for a human child is equivalent to about 25 mg/m$^2$.

Common dosing frequencies may range, for example, from twice daily to once a month (e.g., once daily, once weekly; once every other week; once every 3 weeks, once every 4 weeks or monthly). For example, conjugates of XMT-1535 disclosed herein can be administered (e.g., as a single dose weekly, every 2 weeks, every 3 weeks, every 4 weeks or monthly) at about 0.1 mg/kg to about 20 mg/kg (e.g., 0.2 mg/kg, 0.4 mg/kg, 0.5 mg/kg, 0.67 mg/kg, 0.8 mg/kg, 1 mg/kg, 1.25 mg/kg, 1.67 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg). For example, conjugates of XMT-1535 disclosed herein can be administered (e.g., as a single dose weekly, every 2 weeks, every 3 weeks, every 4 weeks or monthly) at about 0.1 mg/kg to about 20 mg/kg (e.g., 0.2 mg/kg, 0.4 mg/kg, 0.5 mg/kg, 0.67 mg/kg, 0.8 mg/kg, 1 mg/kg, 1.25 mg/kg, 1.67 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg) for treating NaPi2b-expressing ovarian cancer or NaPi2b-expressing NSCLC cancer.

Common dosing frequencies may range, for example, from twice daily to once a month (e.g., once daily, once weekly; once every other week; once every 3 weeks, once every 4 weeks or monthly). For example, conjugates of XMT-1535 disclosed herein can be administered (e.g., as a single dose weekly, every 2 weeks, every 3 weeks, every 4 weeks or monthly) at about 3 mg/m$^2$ to about 53 m$^2$ (e.g., 3 mg/m$^2$, 6 mg/m$^2$, 12 mg/m$^2$, 20 mg/m$^2$, 25 mg/m$^2$, 30 mg/m$^2$, 35 mg/m$^2$, 40 mg/m$^2$, or 53 mg/m$^2$. For example, conjugates of XMT-1535 disclosed herein can be administered (e.g., as a single dose weekly, every 2 weeks, every 3 weeks, every 4 weeks or monthly) at about 3 mg/m$^2$ to about 53 mg/m$^2$ (e.g., 3 mg/m$^2$, 6 mg/m$^2$, 12 mg/m$^2$, 20 mg/m$^2$, 25 mg/m$^2$, 30 mg/m$^2$, 35 mg/m$^2$, 40 mg/m$^2$, or 53 mg/m$^2$) for treating NaPi2b-expressing ovarian cancer or NaPi2b-expressing NSCLC cancer.

Efficaciousness of treatment is determined in association with any known method for diagnosing or treating the particular NaPi2b-related disorder. Alleviation of one or more symptoms of the NaPi2b-related disorder indicates that the antibody confers a clinical benefit.

Kits

The invention provides kits comprising the chimeric NaPi2b antibodies (e.g., MERS67) that detects the level of NaPi2b expression in a patient sample (e.g., the number of antigens per cell) and a therapeutic composition comprising an effective amount of a NaPi2b-targeted polymer antibody-drug conjugate as described herein or disclosed in WO 2017/160754. If desired, the kit further comprises directions for detecting the level of NaPi2b expression and determining whether or not the NaPi2b-targeted polymer antibody-drug conjugate disclosed in WO 2017/160754 would be effective if administered to the patient. Preferably, the kit is an immunohistochemical test kit. Optionally, the kit further comprises instructions for administering a NaPi2b-targeted polymer antibody-drug conjugate as described herein or disclosed in WO 2017/160754 to a patient selected to receive such treatment.

Definitions

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the terms "NaPi2b" (also known as sodium-dependent phosphate transport protein 2B, SLC34A2, NaPiIIb, Npt2, Na(+)-dependent phosphate cotransporter 2B; sodium/phosphate cotransporter 2B; Na(+)/Pi cotransporter 2B; NaPi3b; solute carrier family 34 member 2), when used herein, refers to human NaPi2b (e.g., GenBank Accession No. 095436.3) and includes any variants, isoforms and species homologs of NaPi2b which are naturally expressed by cells, including tumor cells, or are expressed on cells transfected with the NaPi2b gene. These terms are synonymous and may be used interchangeably.

As used herein, the term "NaPi2b antibody" or "anti-NaPi2b antibody" is an antibody that binds specifically to the antigen NaPi2b.

When used herein in the context of two or more antibodies, the term "competes with" or "cross-competes with" indicates that the two or more antibodies compete for binding to NaPi2b, e.g., compete for NaPi2b binding in any art-recognized assay. An antibody "blocks" or "cross-blocks" one or more other antibodies from binding to NaPi2b if the antibody competes with the one or more other antibodies 25% or more, with 25%-74% representing "partial block" and 75%-100% representing "full block", as determined using any art-recognized assay. For some pairs of antibodies, competition or blocking in any art-recognized assay is only observed when one antibody is coated on the plate and the other is used to compete, and not vice versa. Unless otherwise defined or negated by context, the terms "competes with", "cross-competes with", "blocks" or "cross-blocks" when used herein is also intended to cover such pairs of antibodies.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal and chimeric antibodies.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. Monoclonal antibodies (mAbs) contain an antigen-binding site capable of immunoreacting with a particular epitope of the antigen characterized by a unique binding affinity for it.

As used herein the term "chimeric" means that the antibody or antigen-binding portion includes sequences from two different species. Chimeric antibodies are immunoglobulin molecules comprising a human and non-human portion. More specifically, the antigen combining region (variable region) of a chimeric antibody is derived from a human source and the constant region of the chimeric antibody which confers biological effector function to the immunoglobulin is derived from a non-human source. The chimeric antibody should have the antigen binding specificity of the human antibody molecule and the effector function conferred by the non-human antibody molecule. Methods of producing chimeric antibodies according to the invention will be familiar to persons skilled in the art, see for example, U.S. Pat. Nos. 4,816,567, 5,585,089 and US 20030039649 which are incorporated herein by reference in their entirety. Such methods require the use of standard recombinant techniques.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM; e.g., $\leq 100$ nM, preferably $\leq 10$ nM and more preferably $\leq 1$ nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to NaPi2b, when the equilibrium dissociation constant ($K_d$ or $K_D$) is $\leq 1$ µM, preferably $\leq 100$ nM, more preferably $\leq 10$ nM, and most preferably $\leq 100$ pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxyribonucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides disclosed herein are either sense or antisense oligonucleotides.

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Green, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions that are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present disclosure, providing that the variations in the amino acid sequence maintain at least 75%, more preferably at least 80%, 85%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Analogs of antibodies or immunoglobulin molecules can be readily prepared by those of ordinary skill in the art. Preferred amino- and carboxy-termini of analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}n$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. For example, a polymeric scaffold of a certain formula includes all the monomer units shown in the formula and may also include additional monomer units not shown in the formula. Additionally whenever "comprising" or another open-ended term is used in an embodiment, it is to be understood that the same embodiment can be more narrowly claimed using the intermediate term "consisting essentially of" or the closed term "consisting of."

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

"Drug": As used herein, the term "drug" refers to a compound which is biologically active and provides a desired physiological effect following administration to a subject in need thereof (e.g., an active pharmaceutical ingredient).

"Anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. The angiogenesis inhibitor includes those agents that bind and block the angiogenic activity of the angiogenic factor or its receptor. For example, an anti-angiogenesis agent is an antibody or other antagonist to an angiogenic agent as including, but not limited to, antibodies to VEGF-A or to the VEGF-A receptor (e.g., KDR receptor or Flt-1 receptor), VEGF-trap, anti-PDGFR inhibitors such as Gleevec™ (Imatinib Mesylate). Anti-angiogenesis agents also include native angiogenesis inhibitors, e.g., angiostatin, endostatin, and the like.

"Cytotoxic": As used herein the term "cytotoxic" means toxic to cells or a selected cell population (e.g., cancer cells). The toxic effect may result in cell death and/or lysis. In certain instances, the toxic effect may be a sublethal destructive effect on the cell, e.g., slowing or arresting cell growth. In order to achieve a cytotoxic effect, the drug or prodrug may be selected from a group consisting of a DNA damaging agent, a microtubule disrupting agent, or a cytotoxic protein or polypeptide, amongst others.

"Cytostatic": As used herein the term "cytostatic" refers to a drug or other compound that inhibits or stops cell growth and/or multiplication.

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred embodiments, the small molecule is a drug and the small molecule is referred to as "drug molecule" or "drug" or "therapeutic agent". In certain embodiments, the drug molecule has MW less than or equal to about 5 kDa. In other embodiments, the drug molecule has MW less than or equal to about 1.5 kDa. In embodiments, the drug molecule is selected from vinca alkaloids, auristatins, duocarmycins, tubulysins, non-natural camptothecin compounds, topoisomerase inhibitors, DNA binding drugs, kinase inhibitors, MEK inhibitors, KSP inhibitors, calicheamicins, SN38, pyrrolobenzodiazepines, and analogs thereof. Preferably, though not necessarily, the drug is one that has already been deemed safe and effective for use by an appropriate governmental agency or body, e.g., the FDA. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered suitable for use with the present hydrophilic polymers.

"Drug derivative" or "modified drug" or the like as used herein, refers to a compound that comprises the drug molecule intended to be delivered by the conjugate disclosed herein and a functional group capable of attaching the drug molecule to the polymeric carrier.

"Active form" as used herein refers to a form of a compound that exhibits intended pharmaceutical efficacy in vivo or in vitro. In particular, when a drug molecule intended to be delivered by the conjugate disclosed herein is released from the conjugate, the active form can be the drug itself or its derivatives, which exhibit the intended therapeutic properties. The release of the drug from the conjugate can be achieved by cleavage of a biodegradable bond of the linker that attaches the drug to the polymeric carrier. The active drug derivatives accordingly can comprise a portion of the linker.

"PHF" refers to poly(1-hydroxymethylethylene hydroxymethyl-formal).

As used herein, the terms "polymer unit", "monomeric unit", "monomer", "monomer unit", "unit" all refer to a repeatable structural unit in a polymer.

As used herein, "molecular weight" or "MW" of a polymer or polymeric carrier/scaffold or polymer conjugates refers to the weight average molecular weight of the unmodified polymer unless otherwise specified.

As used herein, "treating" or "treat" describes the management and care of a patient for the purpose of combating a disease, condition, or disorder and includes the administration of a conjugate of the disclosure, or a pharmaceutical composition thereof, to alleviate the symptoms or complications of a disease, condition or disorder, or to eliminate the disease, condition or disorder.

As used herein, "prevention" or "prophylaxis" refers to reduction in the risk of developing a disease or condition, or reduction or elimination of the onset of the symptoms or complications of the disease, condition or disorder.

The term "effective amount" or "sufficient amount", as it refers to an active agent, refers to the amount necessary to elicit the desired biological response. As used herein, a "therapeutically effective amount" or a "therapeutically effective dose" refers to an amount or quantity of an agent, compound, material, or composition containing a compound that is at least sufficient to produce a detectable therapeutic effect. The effect can be detected by any assay method known in the art. The precise effective amount for a subject will depend upon the subject's body weight, size, and health; the nature and extent of the condition; and the therapeutic selected for administration.

A "subject" includes a human as well as a non-human animal, at any stage of development, including, for example, e.g., any mammal, a human, primate, bird, mouse, rat, fowl, dog, cat, cow, horse, goat, camel, sheep or a pig. Preferably, the non-human animal is a mammal (e.g., a rodent, a mouse, a rat, a rabbit, a monkey, a dog, a cat, a primate, or a pig). An animal may be a transgenic animal or a human clone. Preferably, the mammal is a human. The term "subject" encompasses animals.

As used herein a "kit" refers to a combination of components, such as a combination of the compositions herein and another item for a purpose including, but not limited to, reconstitution, activation and instruments/devices for delivery, administration, diagnosis and assessment of a biological activity or property. Kits optionally include instructions of use.

As used herein "contacting" refers to reacting, exposing, incubating a tumor sample or specimen with an anti-NaPi2b antibody As used herein "patent response" or "response" or "benefit" from treatment can be assessed using any endpoint indicating a benefit to the patient, including, without limitation, (1) inhibition, to some extent, of disease progression including, but not limited to, disease progression, including slowing down and complete arrest (2) reduction in the number of disease episodes and/or symptoms (3) reduction in tumor size (4) inhibition (i.e. reduction, slowing down or complete stopping) of disease spread (5) relief, to some extent, of one or more symptoms associated with the disease (6) decreased mortality at a given time point following treatment.

As used herein "tissue sample" is meant a collection of similar cells obtained from a tissue of a subject or individual. The source of the tissue may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue sample is obtained from a disease tissue/organ. For instance, a "tumor sample" is a tissue sample obtained from a tumor or other cancerous tissue. The tissue sample may contain a mixed population of cell types (e.g., tumor cells and non-tumor cells, cancerous cells and non-cancerous cells). The tissue sample may contain compounds which are not naturally intermixed with the tissue in nature such as preservatives, anticoagulants, buffers, fixatives, nutrients, antibiotics, or the like.

The term "prediction" or "predicting" used herein refers to the likelihood that a patient will respond either favorably or unfavorably to a drug (therapeutic agent) or set of drugs or a therapeutic regimen. In one embodiment, the prediction relates to the extent of those responses. In one embodiment, the prediction relates to whether and/or the probability that a patient will survive or improve following treatment, for example treatment with a particular therapeutic agent, or for a certain period of time without disease recurrence. The prediction methods of the invention can be used clinically to make treatment decisions by choosing the most appropriate treatment modalities for any particular patient. The prediction methods of the present invention are valuable tools in prediction if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely "Clinical parameters" encompasses all non-sample or non-NaPi2b status of the subject health status or other characteristics, such as, without limitation, age (Age), ethnicity (RACE), gender (Sex), or family history (FamHX).

"FN" is false negative, which for a disease state test means classifying a disease subject incorrectly as non-disease, non-responsive to treatment, or normal.

"FP" is false positive, which for a disease state test means classifying a normal subject incorrectly as having disease or being responsive to treatment.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity). The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art.

A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4.sup.th edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronary Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935. Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Sensitivity" is calculated by TP/(TP+FN) or the true positive fraction of subjects.

"Specificity" is calculated by TN/(TN+FP) or the true negative fraction of normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is considered highly significant at a p-value of 0.05 or less. Preferably, the p-value is 0.04, 0.03, 0.02, 0.01, 0.005, 0.001 or less.

"Traditional laboratory risk factors" correspond to biomarkers isolated or derived from subject samples and which are currently evaluated in the clinical laboratory and used in traditional global risk assessment algorithms. Traditional laboratory risk factors for tumor recurrence include for example Proliferative index, tumor infiltrating lymphocytes. Other traditional laboratory risk factors for tumor recurrence known to those skilled in the art.

All methods described herein can be performed in any suitable order unless otherwise indicated herein or otherwise clearly contradicted by context. The use of any and all examples, or exemplary language (e.g., "such as") provided herein, is intended merely to better illustrate the disclosure and is not to be construed as a limitation on the scope of the claims unless explicitly otherwise claimed. No language in the specification is to be construed as indicating that any non-claimed element is essential to what is claimed.

EXAMPLES

Example 1: Cloning, Production, and Purification of MERS67

MERS67 is a human-rabbit chimeric antibody that was designed based on the humanized anti-NaPi2b antibody, XMT-1535 (aka. RebMab200 (Lopes dos Santos, 2013)). It consists of the human heavy and light chain variable sequences joined to the Rabbit IgG1 constant region or the Rabbit Ig kappa-b4 chain C region, respectively. Target DNA sequences were designed with codon optimization from the amino acid sequences of the humanized variable heavy and light chain regions and the rabbit constant regions. Gene synthesis, expression vector construction, plasmid preparation, and transient expression was performed at GenScript®. DNA sequences for the chimeric heavy and light chain are provided in FIG. 1. For production, ExpiCHO-S cells were grown in serum-free ExpiCHO™ Expression Medium (Thermo Fisher Scientific). The cells were maintained in Erlenmeyer Flasks (Corning Inc., Acton, Mass.) at 37° C. with 8% $CO_2$ on an orbital shaker (VWR Scientific). One day before transfection, the cells were seeded at an appropriate density in Corning Erlenmeyer Flasks. On the day of transfection, DNA and the transfection reagent were mixed at an optimal ratio and then added into the flask with cells ready for transfection. The recombinant plasmids encoding heavy and light chains of Mers67 were transiently co-transfected into suspension ExpiCHO-S cell cultures. The cells were transferred to 32° C. incubator with 5% $CO_2$ on day 1 post-transfection for remaining culture. Enhancer and feed (Thermo Fisher Scientific) were added on day 1 and feed was added on day 5 post-transfection. The cell culture supernatant collected on day 14 was used for purification.

Figure 3A:
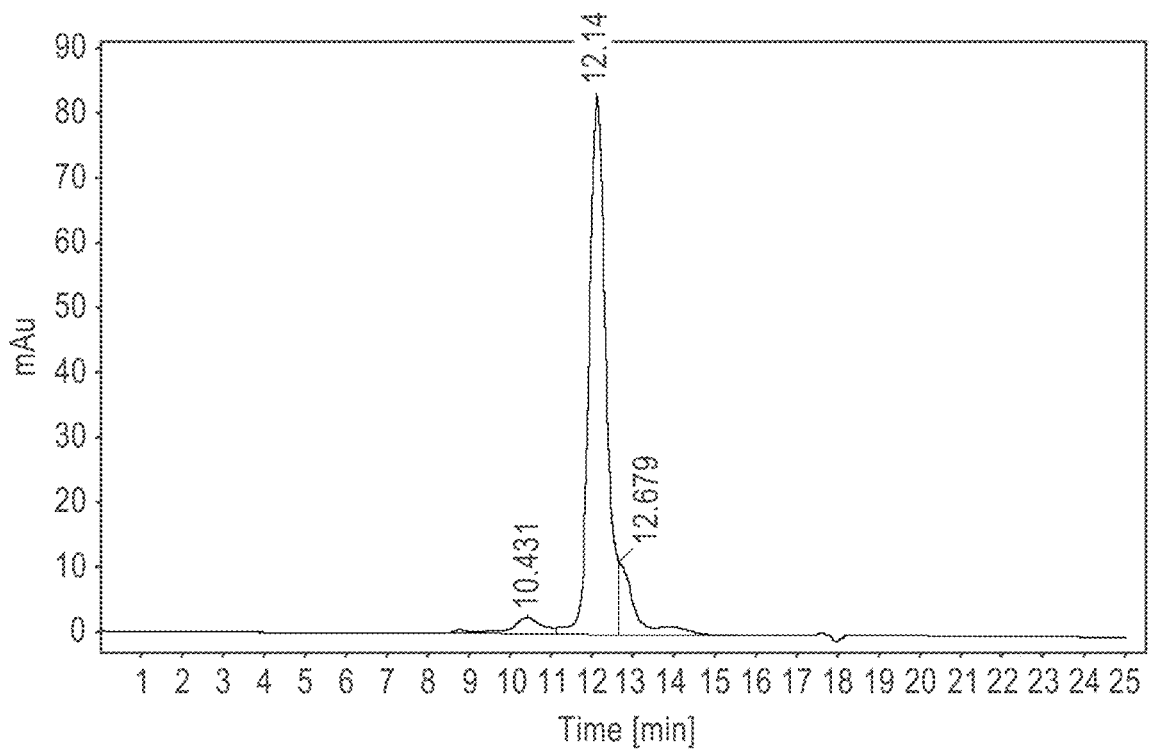
FIG. 3A shows SEC-HPLC analysis of MERS67 after one-step purification.
Figure 3B:
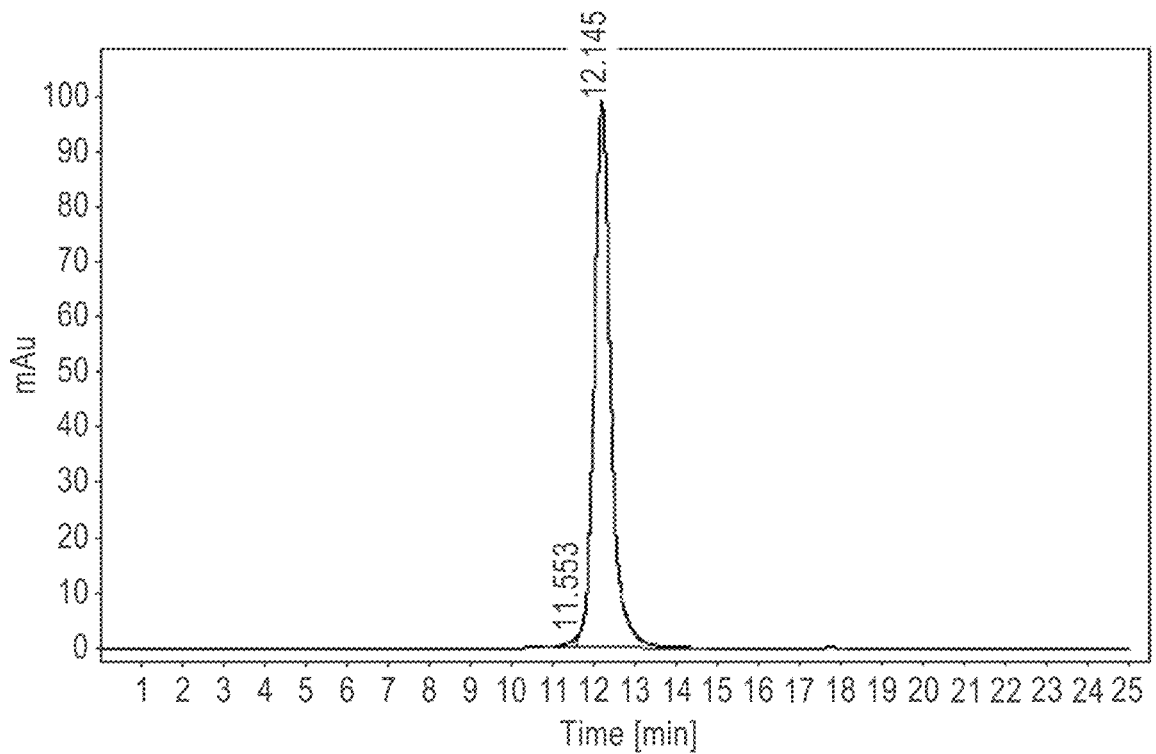
FIG. 3B shows SEC-HPLC analysis of MERS67 after two-step purification

Cell culture broth was centrifuged and followed by filtration. Filtered supernatant was loaded onto protein A Column (GenScript, Cat. No. L00433) at 3 mL/min. After washing and elution with appropriate buffer, the eluted fractions were buffer exchanged to PBS. The target protein was further purified via HiLoad Superdex 200 16/600 pg column (GE Healthcare, Uppsala, Sweden) to remove high molecular weight aggregates. The purified protein was analyzed by SDS-PAGE, Western blot and SEC-HPLC by using standard protocols for molecular weight, yield and purity measurements as shown in FIG. 2 and FIG. 3A (after one step purification, Lot U0859BH) and FIG. 3B (after two step purification, LotU5696BL). 5 µg of sample was loaded on SDS-PAGE and 0.3 µg of total protein was loaded on Western blot. The primary antibody for Western blot was Goat Anti-Rabbit IgG-HRP (GenScript, Cat No. A00131).

Example 2: Binding of MERS67 to Human NaPi2b Peptide

The binding of MERS67 was evaluated in comparison to the binding of the parental antibody, XMT-1535.

Human cyclized NaPi2b peptide were generated and lyophilized covering the amino acids identified in the XMT-1535 epitope (New England Peptide, Gardner, Mass.). For the ELISA, the lyophilized NaPi2b peptide was reconstituted in DMSO. Human NaPi2b peptide was used to coat 96-Well high binding clear ELISA plates (Corning, 3369) at 1 µg/mL in sodium carbonate buffer, pH 9 to a total volume of 100 µl per well. After a 2-hour incubation, plates were washed 4 times with 100 µl per well TBS-Tween 20, blocked with 3% BSA in TBS-Tween 20 (100 µl per well) for 1 hour, and washed again. Test articles, MERS67 (Lot U0859BH and Lot U5569BL), XMT-1535, and the non-binding control (trastuzumab) were added to the wells at a dose concentration range from 100 nM to 0.002 nM using an 8-point 3-fold serial dilution in TBS-Tween 20 buffer at 100 µl per well. Plates were incubated for 1 hour with rocking then washed as above. Peroxidase-Conjugated AffiniPure Goat Anti-Human IgG F(ab')2 Fragment specific secondary antibody (Jackson ImmunoResearch, 109-035-097) was used at 5000× in TBS-Tween 20 buffer at 100 µl per well for XMT-1535 and Trastuzumab and goat anti-rabbit HRP secondary antibody (Abcam, ab6721) was used for MERS67. Plates were again incubated for 1 hour with rocking followed by wash as above. TMB substrate (Bethyl Lab, E102) was added at 50 µl per well and incubated until color appeared then the reaction was quenched with an equal amount of 0.2N $H_2SO_4$. The Optical Density (O.D.) was measured at 450 nm with a SpectraMax M5 microplate reader (Molecular Devices, Sunnyvale, Calif.). The O.D. for each treatment was graphed, and $K_d$ calculated for each antibody with GraphPad Prism software (GraphPad Software Inc., La Jolla, Calif.) by non-linear regression using the one site-specific binding model.

In two lots examined (Lot U0859BH and Lot U5696BL), MERS67 bound to human NaPi2b with $K_d$ of 0.2561 nM and 0.1045 nM, respectively; XMT-1535 bound to human NaPi2b with a $K_d$ of 0.536 nM. A negative control antibody showed no binding.

Example 3 MERS67 can Detect NaPi2b in an FFPE Immunohistochemical Format

Levels of cell surface expression of NaPi2b were confirmed by flow cytometry. 100 µl of 1×10$^6$ of OVCAR3 or JIMT-1 cells were incubated for one hour in ice with phycoerythrin conjugated RebMAB200 at 5 µg/ml. Using a Quantibrite PE fluorescence calibration kit (BD BioSciences) and a MACS Quant Instrument (Miltenyi Biotec, Bergisch Gladbach, Germany), cell surface receptor number was calculated relative to standard curve to be 1.95×10$^5$ and 120 for OVCAR3 and JIMT-1 respectively.

Cell Pellet and xenograft formalin fixed paraffin embedded blocks were prepared from OVCAR3 and JIMT-1 cell lines using standard methods.

For manual immunohistochemistry analysis, the DAKO Envision+System-HRP (DAB) kit (K4010, Agilent, Santa Clara, Calif.) was used according to the manufacturer's directions. Briefly, slides were sectioned at 5µ, baked at 56° C. for 15 minutes and rehydrated through xylene and graded alcohols. Prior to peroxidase blocking, slides were antigen retrieved in a pH 6.0 solution (Vector Laboratories, Burlingame, Calif.) at 99° C. For the primary antibody incubation step, MERS67 was initially titrated over a range of dilutions in DAKO diluent with background reducing components (S3022, Agilant, Santa Clara, Calif.). A "no primary" antibody control was included in some experimental runs to evaluate the method for non-specific background. Slides were counterstained with Mayer's Hematoxylin, dehydrated, and mounted for examination by light microscopy. Various titrations were compared in a series of xenografts with known response to the NaPi2b-targeted polymer antibody-drug conjugate as disclosed in WO 2017/160754 in vivo, and a titration was chosen that yielded IHC staining that by visual light microscopic reading best distinguished responders and non-responders in a series of preclinical xenograft models. Results for control OVCAR3 and JIMT1 xenograft staining are shown in FIG. 4. Immunohistochemistry was also established using an automated TechMate 500 or TechMate 1000 (BioTek Solutions/Ventana medical Systems) platform, where various antigen retrieval conditions and primary antibody titrations were tested to develop a higher through-put protocol. A protocol was selected based on staining of control material and staining of preclinical material with known response to ADC treatment. Briefly, for the established protocol, 4µ sections were cut, dewaxed, and rehydrated through xylene and a series of alcohols. Slides were antigen retrieved in a standard steamer using BioGenex AR-10 retrieval solution. On the TechMate platform, further retrieval was performed with Proteinase K (DAKO). Following serum blocking: the primary antibody was applied for 30 minutes at room temperature, then endogenous peroxidase block and non-biotin polymer-based detection (rabbit Polink-2 Plus detection system, GBI) was used and finally a brief hematoxylin counterstaining.

Example 4: MERS67 was Used to Detect Immunoreactivity in a Human Tumors and in Human Primary Xenograft Models Using the manual method developed for IHC, a human lung tumor tissue microarray consisting of 37 tumors was stained with MERS67. 21/37 (57%) of tissue cores had detectable membrane immunoreactivity. Immunohistochemical staining of two human lung adenocarcinomas is shown in FIG. 5.

An additional tissue microarray with a variety of tumor types was also evaluated, and immunoreactivity was noted in ovarian carcinoma and very focally in a cholangiocarcinoma. Immunoreactivity could also be detected in a human primary xenograft model of salivary duct carcinoma.

Figure 6:
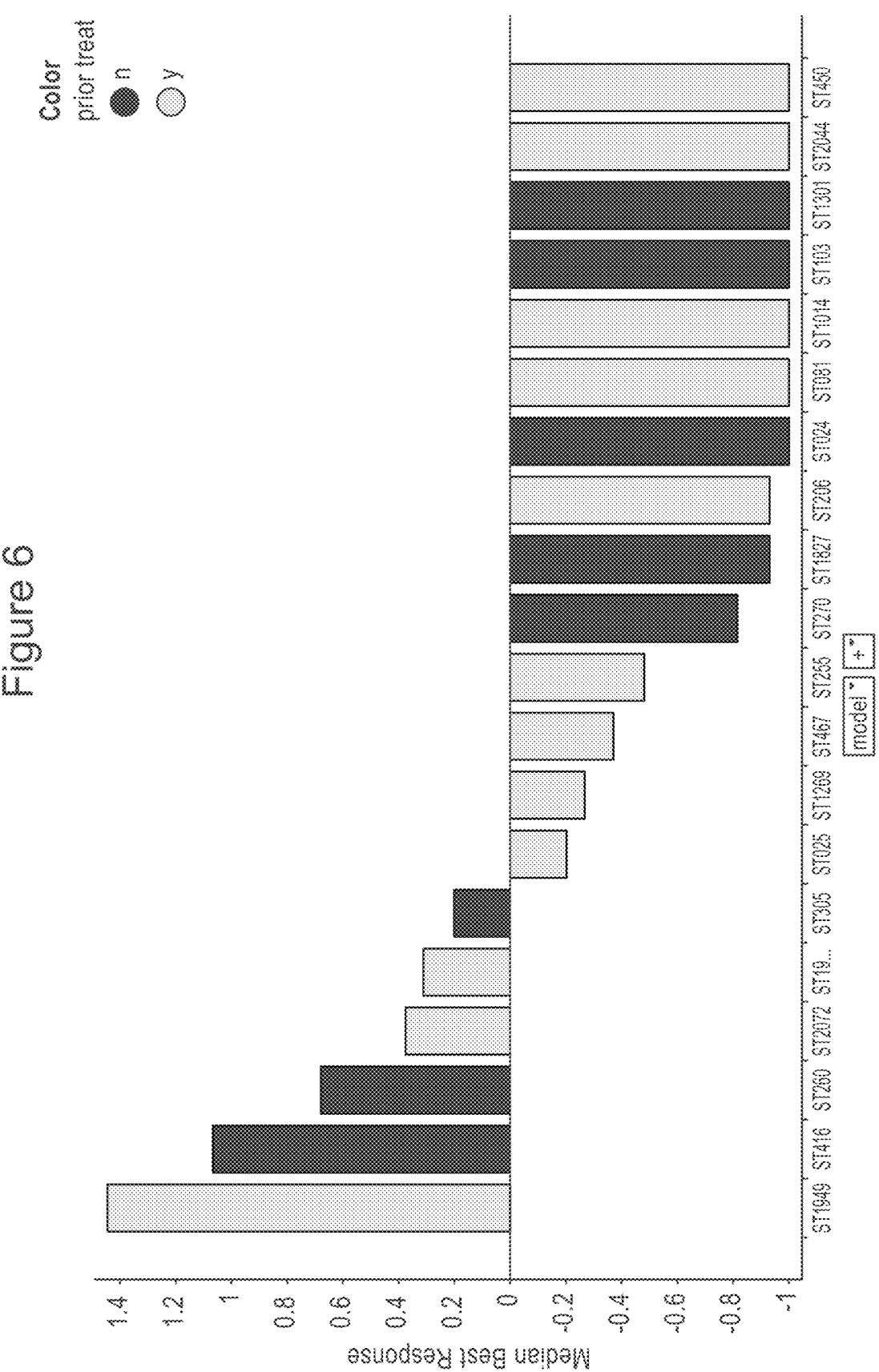
FIG. 6 is a bar chart showing median best response from a mouse ovarian clinical trial using a NaPi2b-targeted polymer antibody-drug conjugate disclosed in WO 2017/160754, n=3, 3 mg/kg qweek×3. The y axis shows the median best response; the x axis shows the model number. The darker colored bars indicate naïve tumors and the lighter colored bars indicate post-treatment tumors.

Example 5: Tumor Growth Response to Administration of NaPi2b-Targeted Polymer Antibody-Drug Conjugate The ovarian primary carcinoma xenograft models were from a set of tumor models derived from serous ovarian or fallopian tube cancers and implanted in immunocompromised mice that were treated with 3 mg/kg NaPi2b-targeted polymer antibody-drug conjugate disclosed in WO 2017/160754 weekly for three weeks in groups of n=3, once tumors reached a stratified mean volume of 125-250 mm$^3$. Untreated animals in groups of n=2-4 were included as a control. The planned study endpoint was a tumor volume of 1 cm$^3$ or 45 days. In a case of complete response, mice were followed for a longer time course to evaluate for tumor regrowth. FIG. 6 is a bar chart shows the median best response calculated relative to day 0 at each timepoint for every animal, and then expressed as the median value of best response for each model. The y axis shows the median best response; the x axis shows the model number. The models were derived both from patients who had received prior treatment and patients who were treatment naïve. Antitumor effect of NaPi2b-targeted polymer antibody-drug conjugate was seen in both tumor classes. Bars are colored as derived from treatment naïve (dark bar) tumors or post-treatment (light bar) tumors. Of the 10 models showing a median best response between −50 and −100, 5 were derived from treatment naïve tumors and 5 from previously treated tumors.

Model ST206, where a sustained antitumor growth effect was seen, was continued for an extended time course. Tissues obtained at the end of study (day 73) in a tumor with incomplete response were evaluated for NaPi2b expression by IHC and showed NaPi2b expression.

Figure 7:
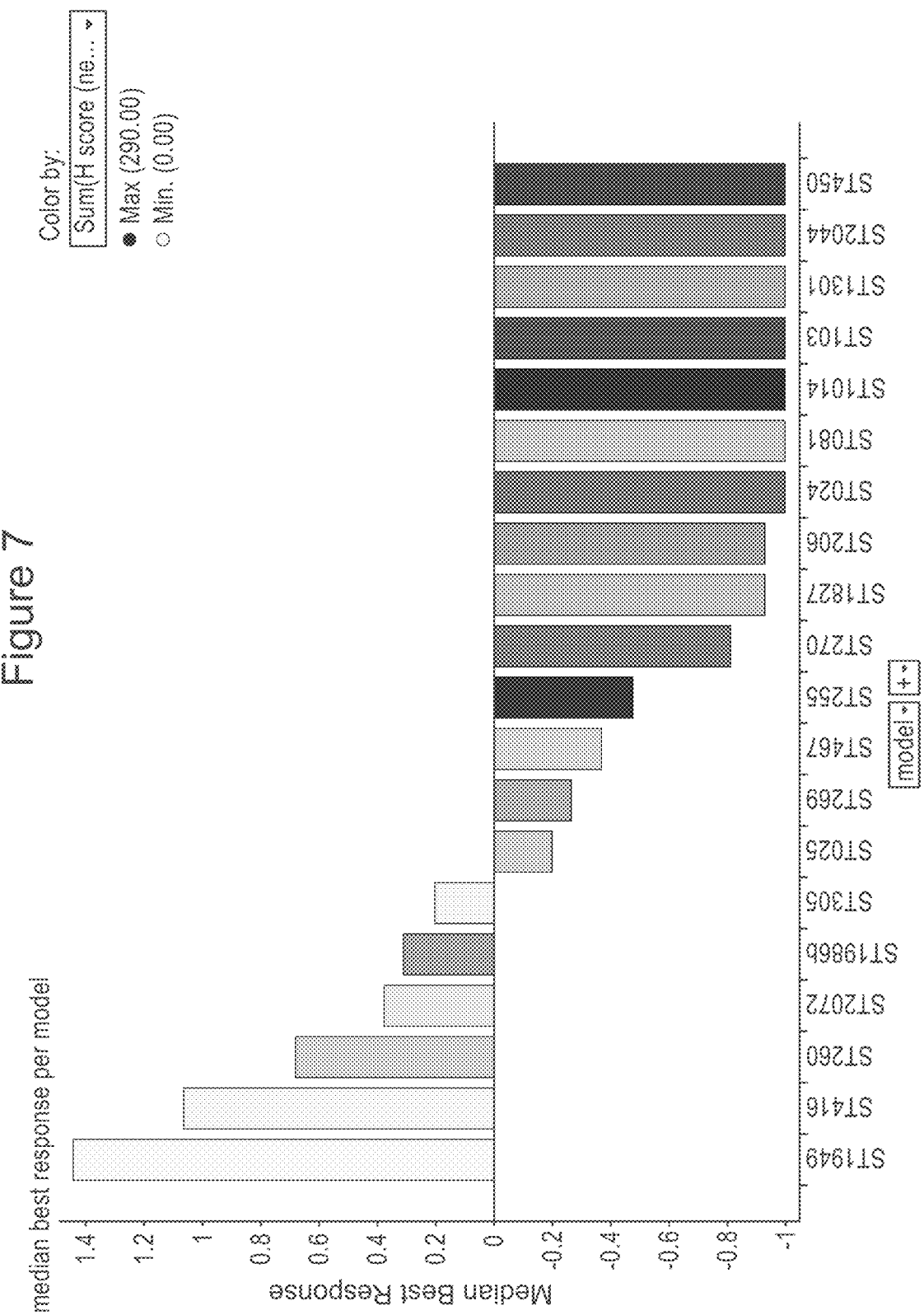
FIG. 7 is a bar chart showing START Ovarian Models, ordered by median best response; and colored by H score (all models). The darker the color the greater the H-score. The y axis shows the median best response; the x axis shows the model number.

Tumor blocks from untreated study animals were evaluated to determine an efficacy/staining pattern relationship. The staining pattern seen in the ovarian cancer models was compared to staining seen in human primary tumors. FIG. 7 is a bar chart showing START Ovarian Models, ordered by median best response; colored by H score (all models). The darker the color the greater the H-score. NaPi2b-targeted polymer antibody-drug conjugate induced at least 50% reduction in tumor volume relative to baseline in 10/20 (50%) models when administered at a dose of 3 mg/kg once weekly for 3 weeks. There was no significant difference in regression rate between treatment-naïve and treatment-exposed tumor models (5/8, 5/12, respectively). Amongst xenograft tumors with H-score ≥70, 10/13 (76%) models achieved 50% or greater reduction in tumor volume after treatment with a NaPi2b-targeted polymer antibody-drug conjugate, vs 0/7 (0%) models with H-score <70. Applying the same IHC assay to primary human ovarian tumors, 12/20 (60%) tested tumors had an H-score ≥70. There was an association between NaPi2b IHC H-score and tumor volume change after NaPi2b-targeted polymer antibody-drug conjugate treatment (Spearman rank coefficient 0.76).

Figure 8:
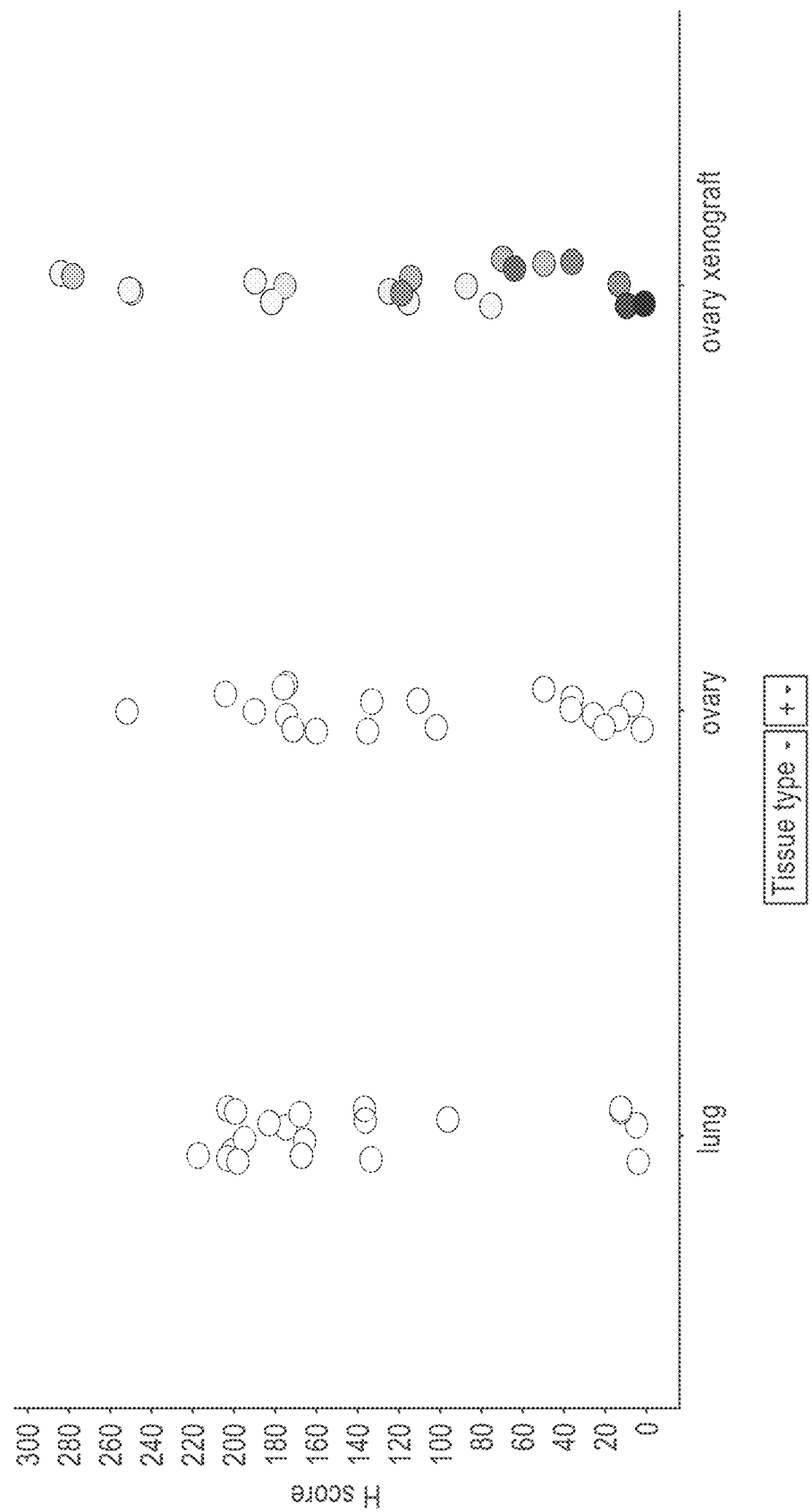
FIG. 8 is a scatter plot showing lung, and ovary human tumors and xenografts. Graphed by H Scores (y axis) and tissue type (x axis), colored by median best response for the xenografts. Lighter colors correspond to more anti-tumor effect; dark colors correspond to less anti-tumor effect.

Using the automated IHC method, a series of 20 human lung adenocarcinomas, 20 ovarian carcinoma and 20 human primary ovarian carcinoma xenograft models were examined, and interpreted using an "H-Score" method. The H-score incorporates staining intensity (determined by increasing intensity from 0 to 3+) as well as percent cells positive detected at the tumor cell membrane. H-Score=(% at <1+×0)+((% at 1+)×1)+((% at 2+)×2)+((%3+)×3). H-Scores ranged from 1-220, 1-250, and 0-290 for the lung, ovarian and xenograft tissues, respectively as shown in a scatter plot in FIG. 8 where the graphed H Scores (y axis) and tissue type (x axis), are colored by median best response for the xenografts.

Example 6: Classification of Lung Cancer

The histopathologic classification of lung cancer is based on morphologic features, but may require ancillary immunohistochemical stains for accurate diagnosis. Non-small cell carcinoma can be divided into a number of subtypes including Squamous Cell Carcinoma (SCC) and Adenocarcinoma (ACA). The use of specific therapeutic agents can be indicated or contraindicated in different lung cancer subtypes (see, for example, Am J Surg Pathol., Volume 35, Number 1, January 2011. Currently, panels of immunohistochemical stains are employed to categorize tumors, for example Cytokeratin 5/6, TTF-1, Napsin A, p40 and p63. NaPi2b protein, detected by MERS67, has expression in normal lung tissue including in cell types that could be precursor to lung ACA (i.e. Type II alveolar cells), and could be a marker for adenocarcinoma. It could be employed as a single stain marker or used to improve current immunohistochemical panels.

Additionally, data from publicly available data sources, RNA expression values of genes commonly assayed at the protein level in an IHC format, mimic the IHC profiles characteristic of adenocarcinoma and squamous cell carcinoma, on a population basis. Viewing the large scale expression data on an individual tumor basis also suggests that understanding the expression level of NaPi2b could help refine the classification of adenocarcinoma and squamous cell carcinoma.

Figure 9:
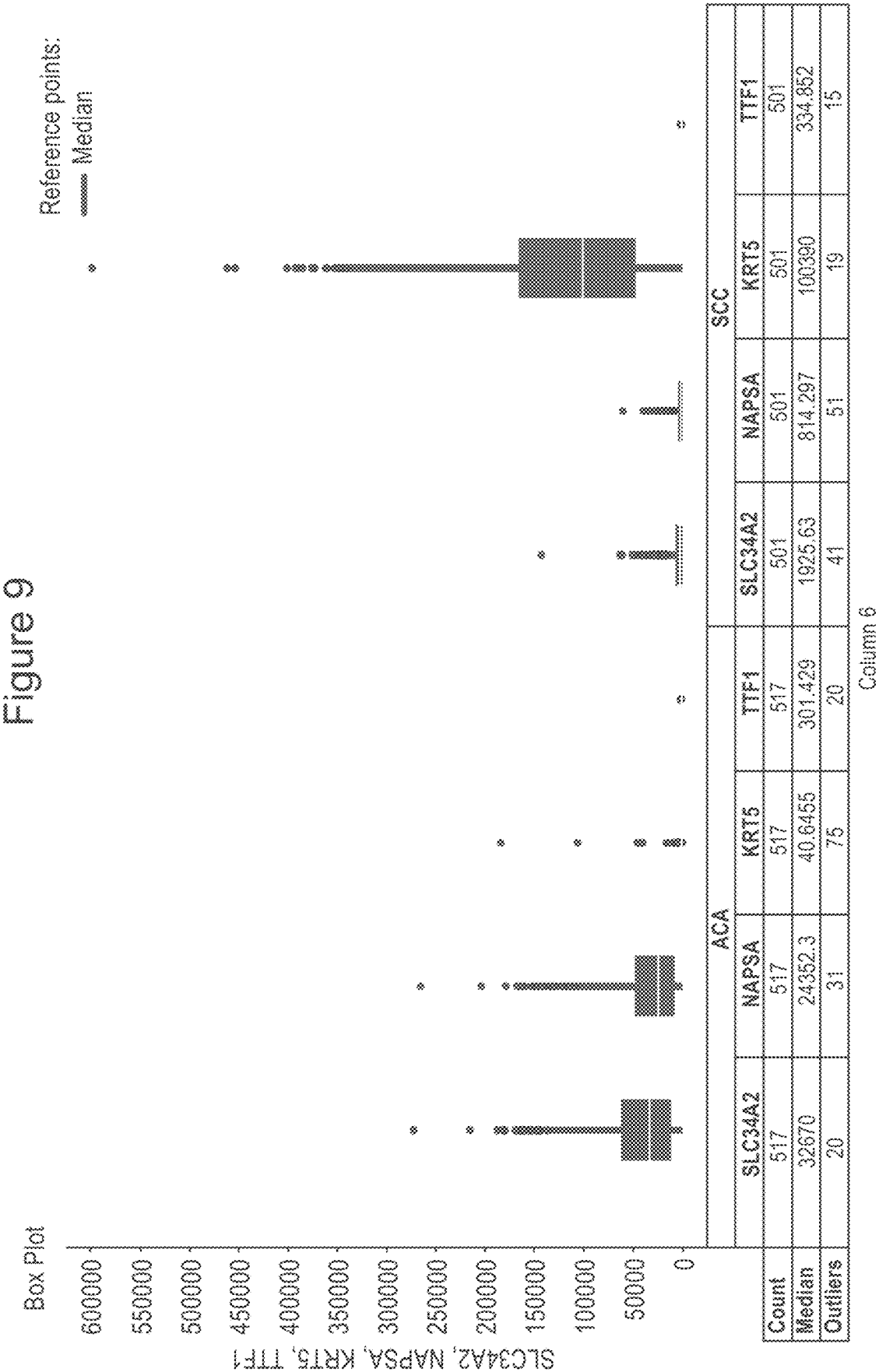
FIG. 9 is a box plot showing RNAseq data extracted from TCGA showing differential expression of NaPi2b, Napsin A, CK5 and TTF1 in Lung SCC and ACC. Immunohistochemical panels detecting protein expression from panels such as Napsin A, CK5 and TTF1 can be used in the classification of squamous cell lung carcinoma and lung adenocarcinoma. Detection of expression of NaPi2b could be used to supplement the currently used panel.

FIG. 9 is a box plot showing RNAseq data extracted from The Cancer Genome Atlas (TCGA) showing differential expression of NaPi2b, Napsin A, CK5 and TTF1 in Lung SCC and ACC. Immunohistochemical panels detecting protein expression from panels such as Napsin A, CK5 and TTF1 from can be used in the classification of squamous cell lung carcinoma and lung adencarcinoma. Detection of expression of NaPi2b could be used to supplement the currently used panel.

Figure 10:
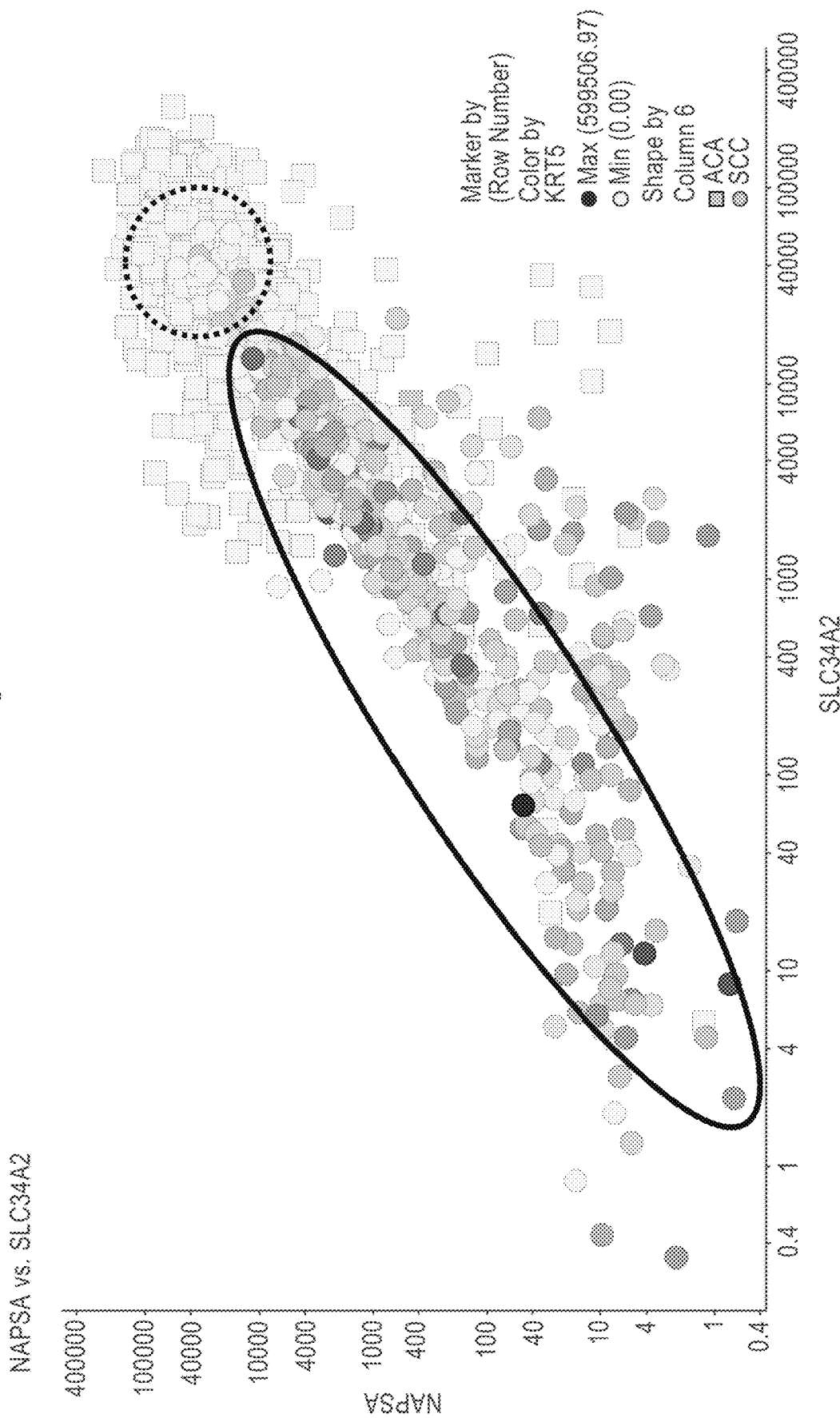
FIG. 10 is a scatter plot showing RNAseq data extracted from TCGA. NaPi2b is shown on the x-axis and Napsin A is shown on the y-axis. Expression of Cytokeratin 5 is indicated by color, with darkest being highest expression level. Most tissues annotated as squamous cell carcinoma (circle shape) are contained within the solid line oval. Most tissues annotated as adenocarcinoma (square shape) are in the upper right quadrant of the graph. Some tumors classified as squamous cell carcinoma area also located in the upper right quadrant, are marked with the dashed circle, and are low expressers of cytokeratin. Use of a protein marker, such as NaPi2b might refine the classification of tumors such as those in the dashed circle.

FIG. 10 is a scatter plot showing RNAseq data extracted from TCGA. NaPi2b is shown on the x-axis and Napsin A is shown on the y-axis. Expression of Cytokeratin 5 is indicated by color, with darkest being highest expression level. Most tissues annotated as squamous cell carcinoma (circle shape) are contained within the solid line oval. Most tissues annotated as adenocarcinoma (square shape) are in the upper right quadrant of the graph. Some tumors classified as squamous cell carcinoma area also located in the upper right quadrant, marked with the dashed circle, and are low expressers of cytokeratin. Use of a protein marker, such as NaPi2b might refine the classification of tumors such as those in the dashed circle.

Figure 11:
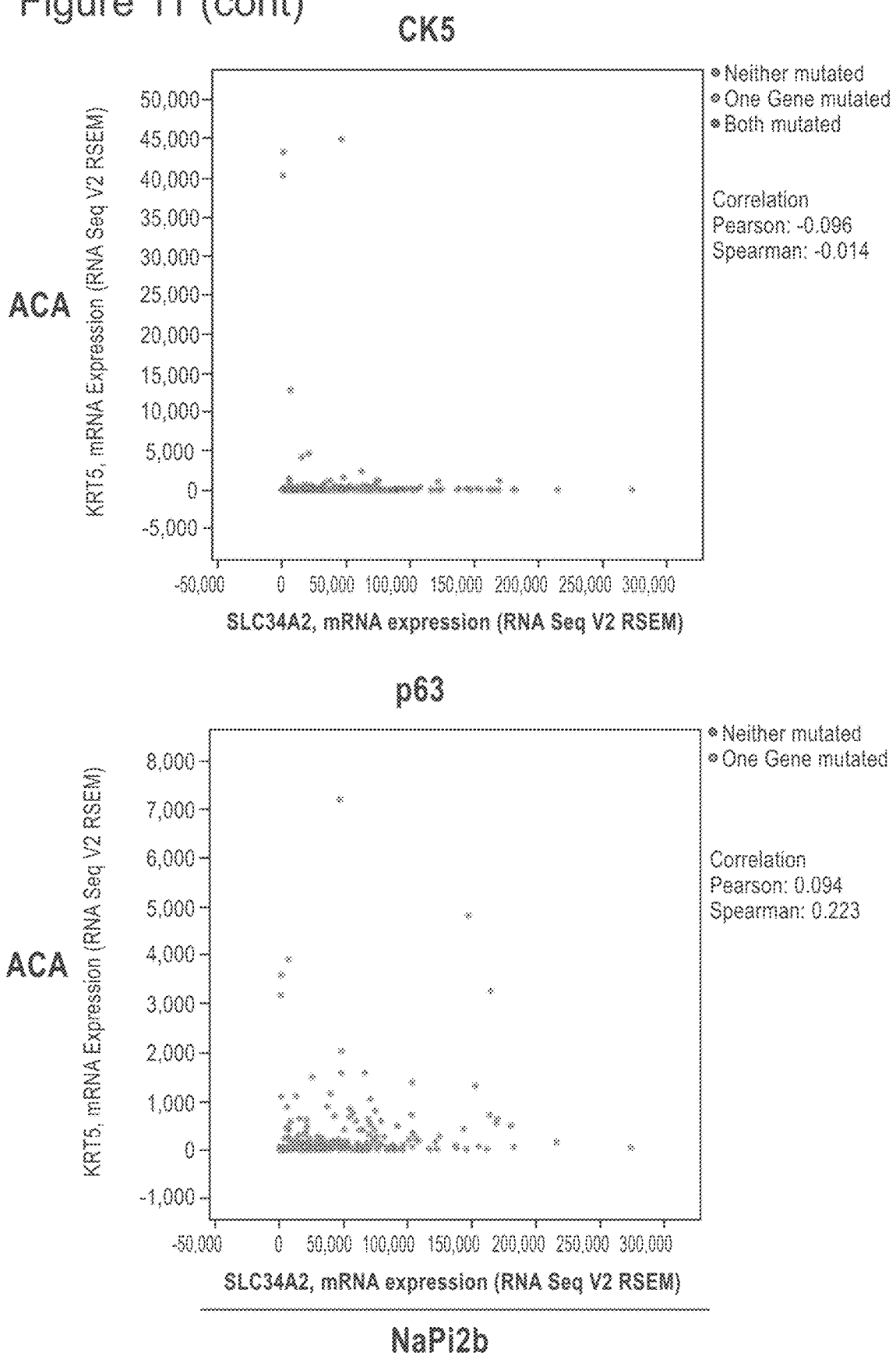
FIG. 11 shows TCGA provisional data as of on May 21, 2018 of lung SCC and ACA extracted from cBioPortal and graphed to show the relationship of NaPi2b RNA expression compared with the TTF-1, Napsin A, CK5 and p63 genes, some genes whose protein products are frequently used to distinguish SCC from ACA. The upper row shows the ACA RNA results and the lower row the SCC RNA results. NaPi2b is shown on the x-axis.
Figure 11:
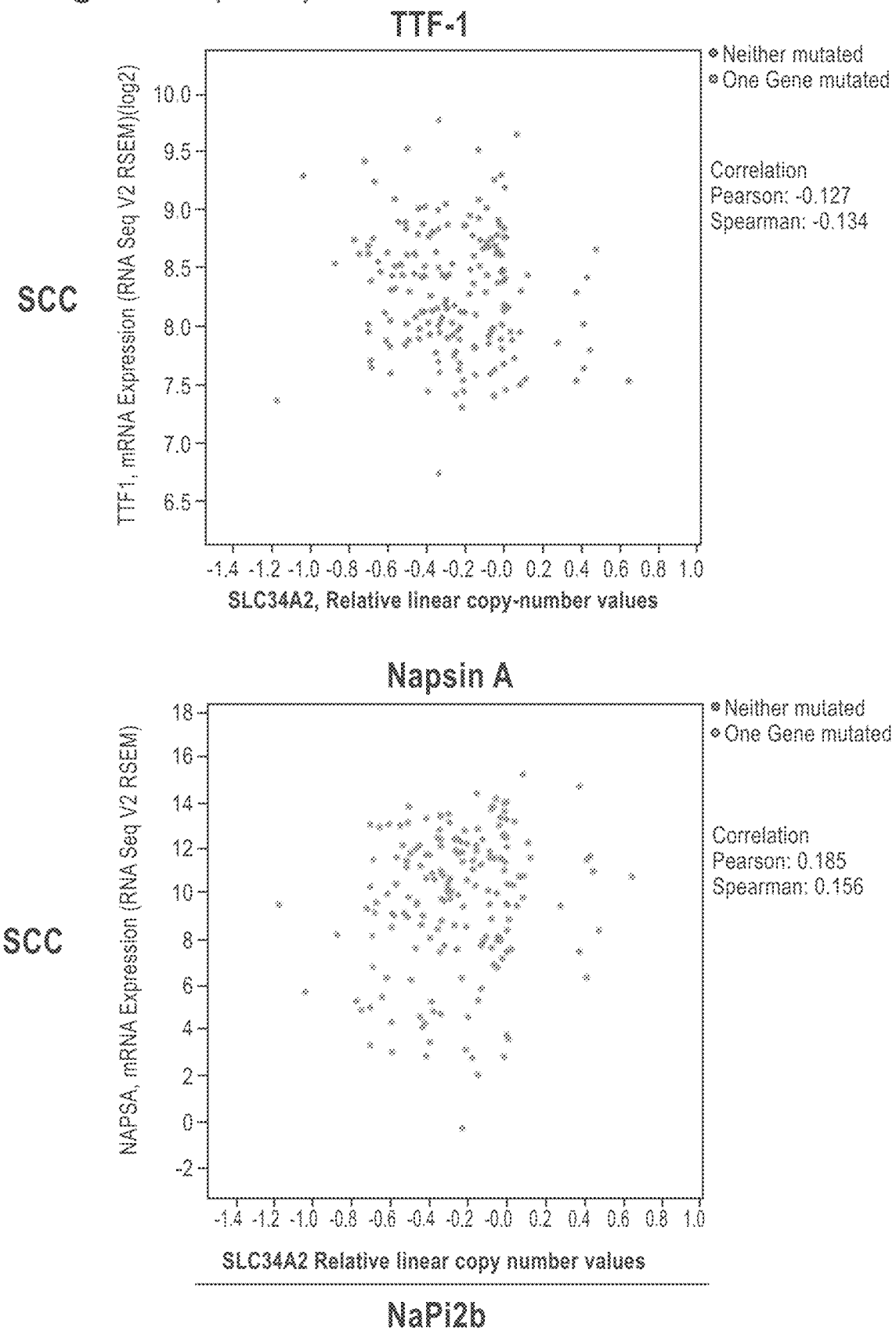
Figure 11:
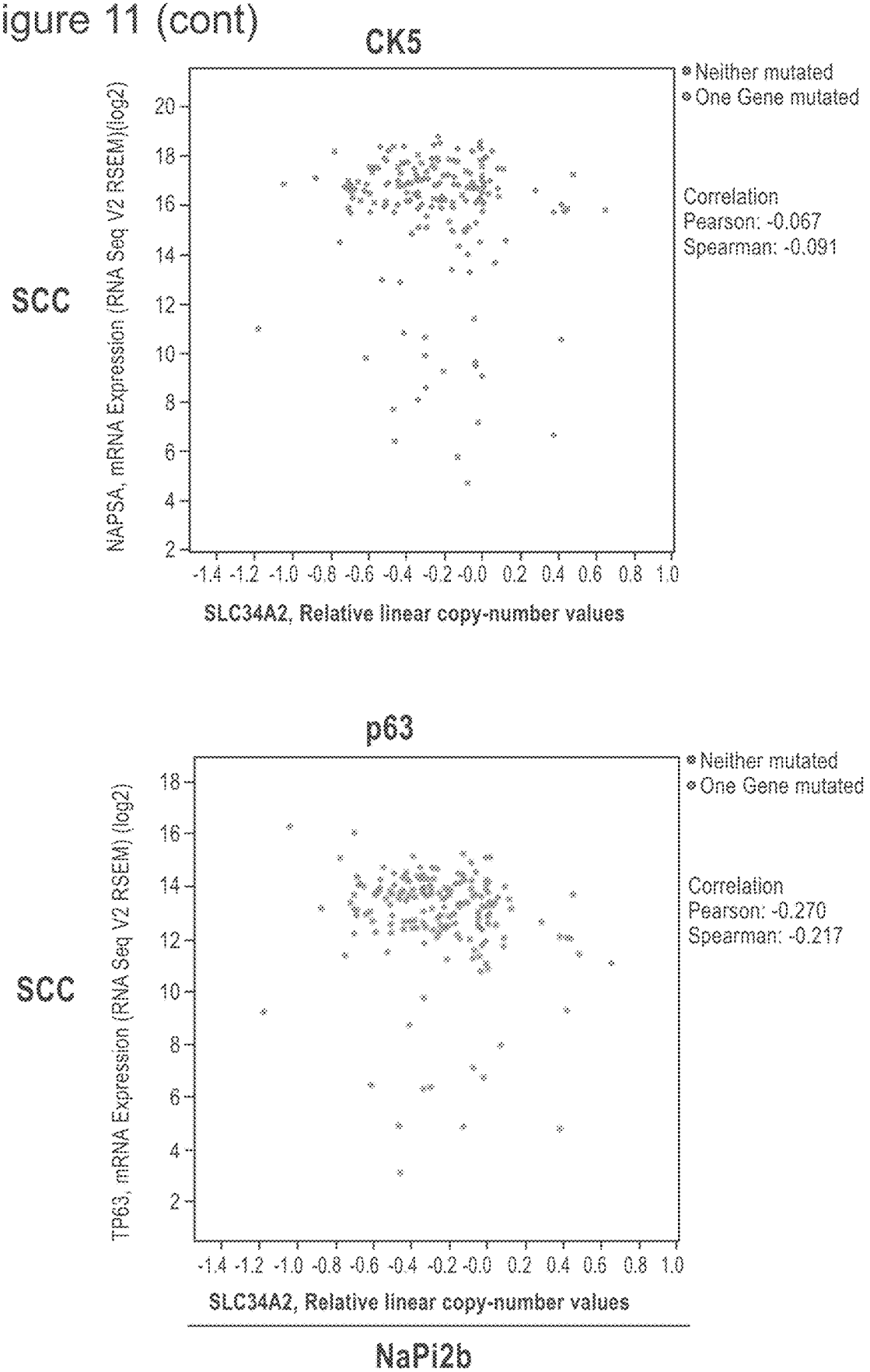

FIG. 11 shows TCGA provisional data as of May 21, 2018 for lung SCC and ACA extracted from cBioPortal (Cerami et al Cancer Discov May 1, 2012 (2) (5) 401-404; Gao et al, Sci. Signal. 2013 Apr. 2; 6(269):pl) and graphed to show the relationship of NaPi2b RNA expression compared with the RNA expression values of the genes TTF-1, Napsin A, CK5, p63 that are more conventionally evaluated by IHC to differentiate SCC and ACA in the clinical setting. The upper row shows the ACA RNA results and the lower row the SCC RNA results. NaPi2b is shown on the x-axis and the gene of interest on the y axes. There appears to be a correlation between the NaPi2b RNA expression with Napsin A genes for ACA, while other genes appear less well or uncorrelated.

Figure 12:
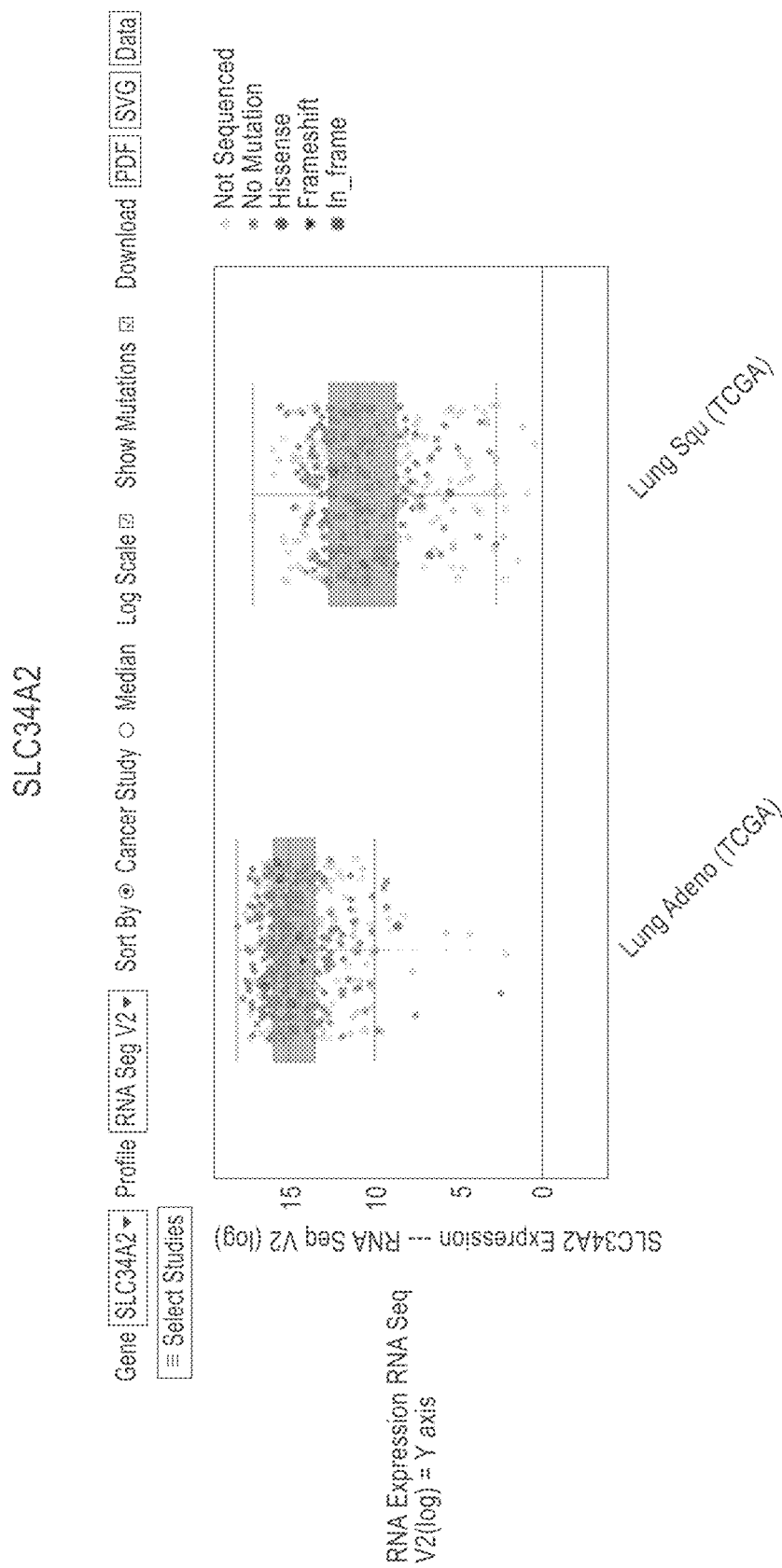
FIG. 12 shows the TCGA provisional RNAseq data as of on May 21, 2018 of lung SCC and ACA extracted from cBioPortal and graphed individually to show the relationship of the SCL34A2, TTF-1, Napsin-A, CK5 and p63 genes for ACA and SCC. In each plot the ACA results are to the left and the SCC data to the right. The y axis is a measure of RNA expression, as determined by RNAseq.
Figure 12:
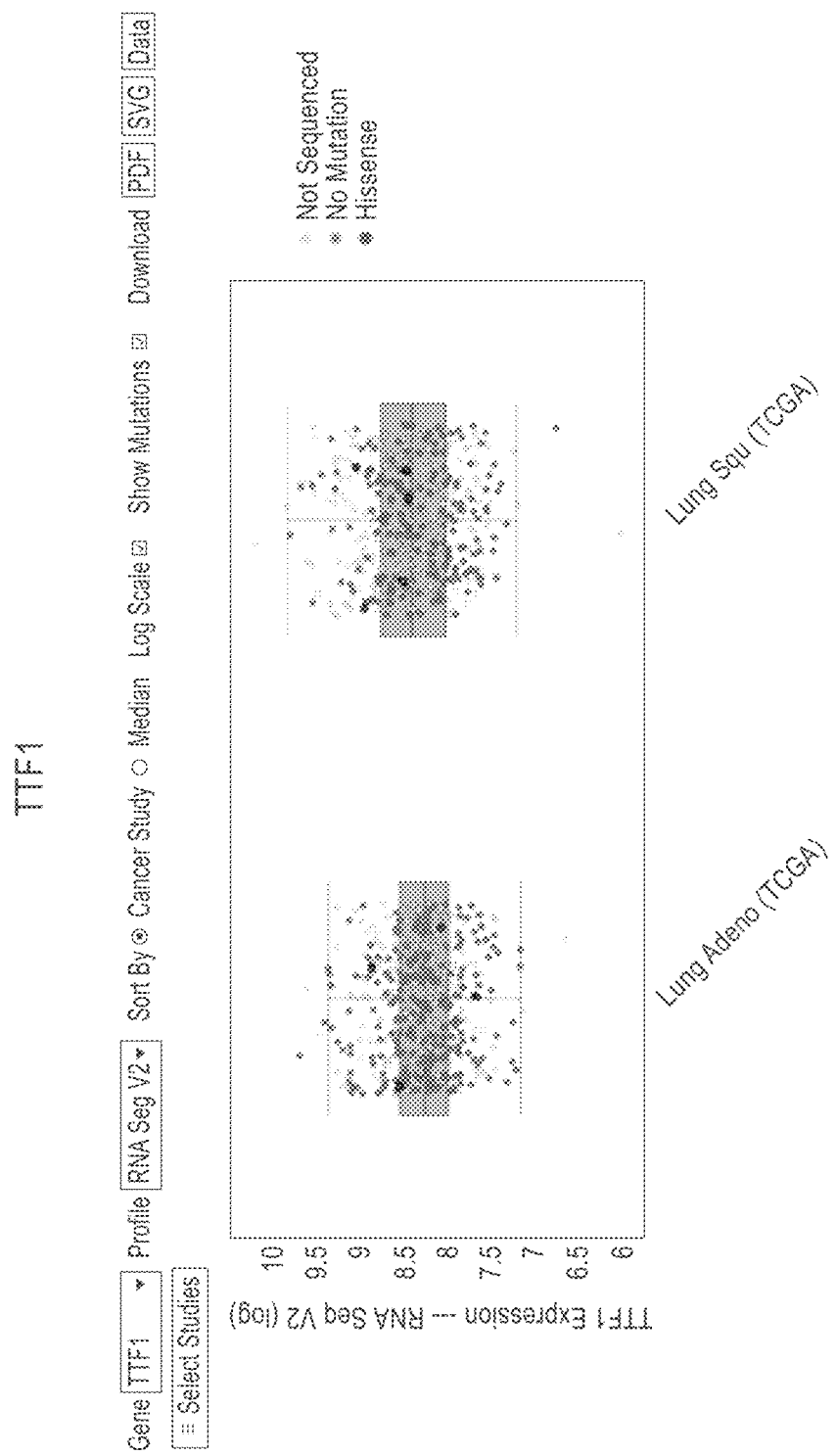
Figure 12:
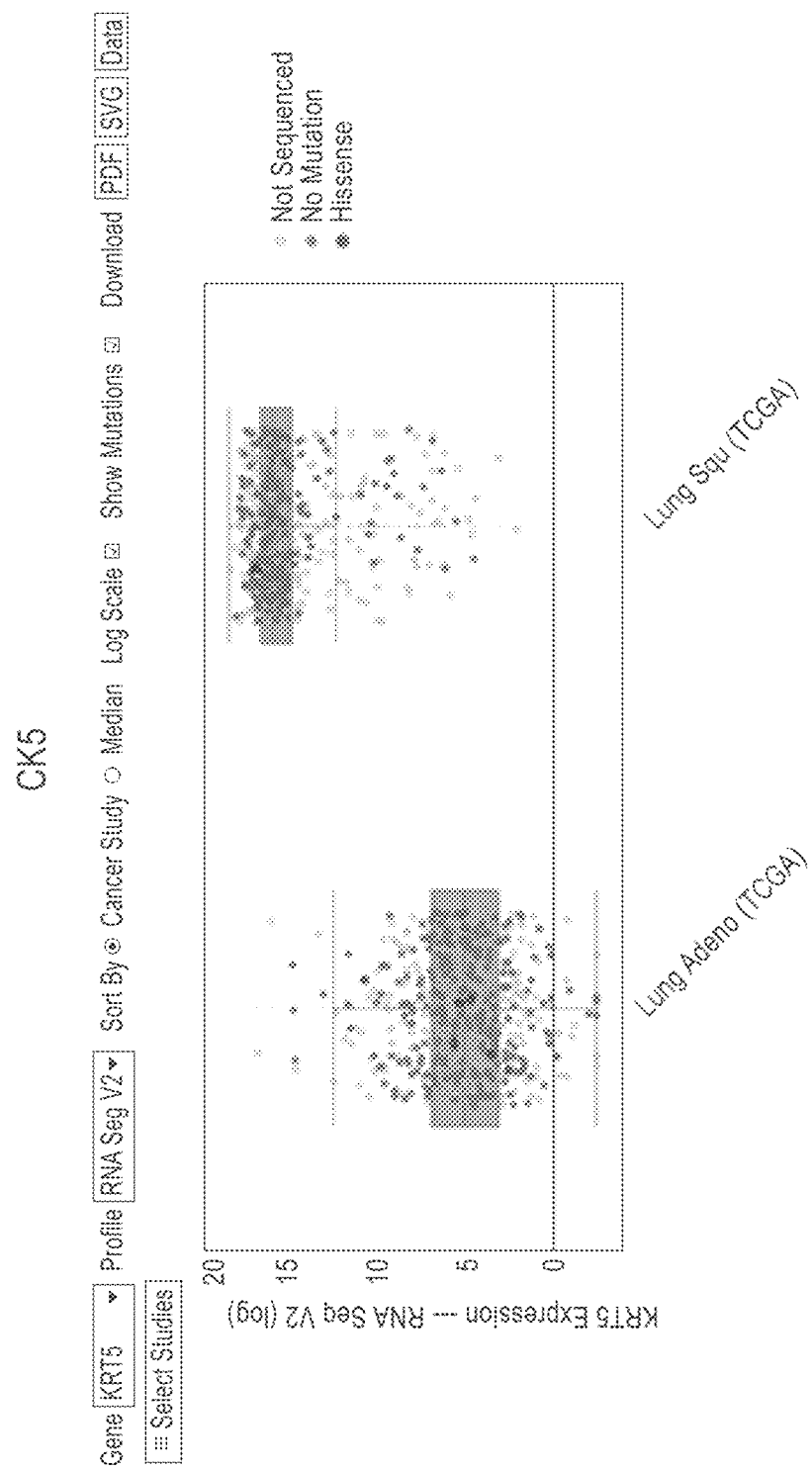
Figure 12:
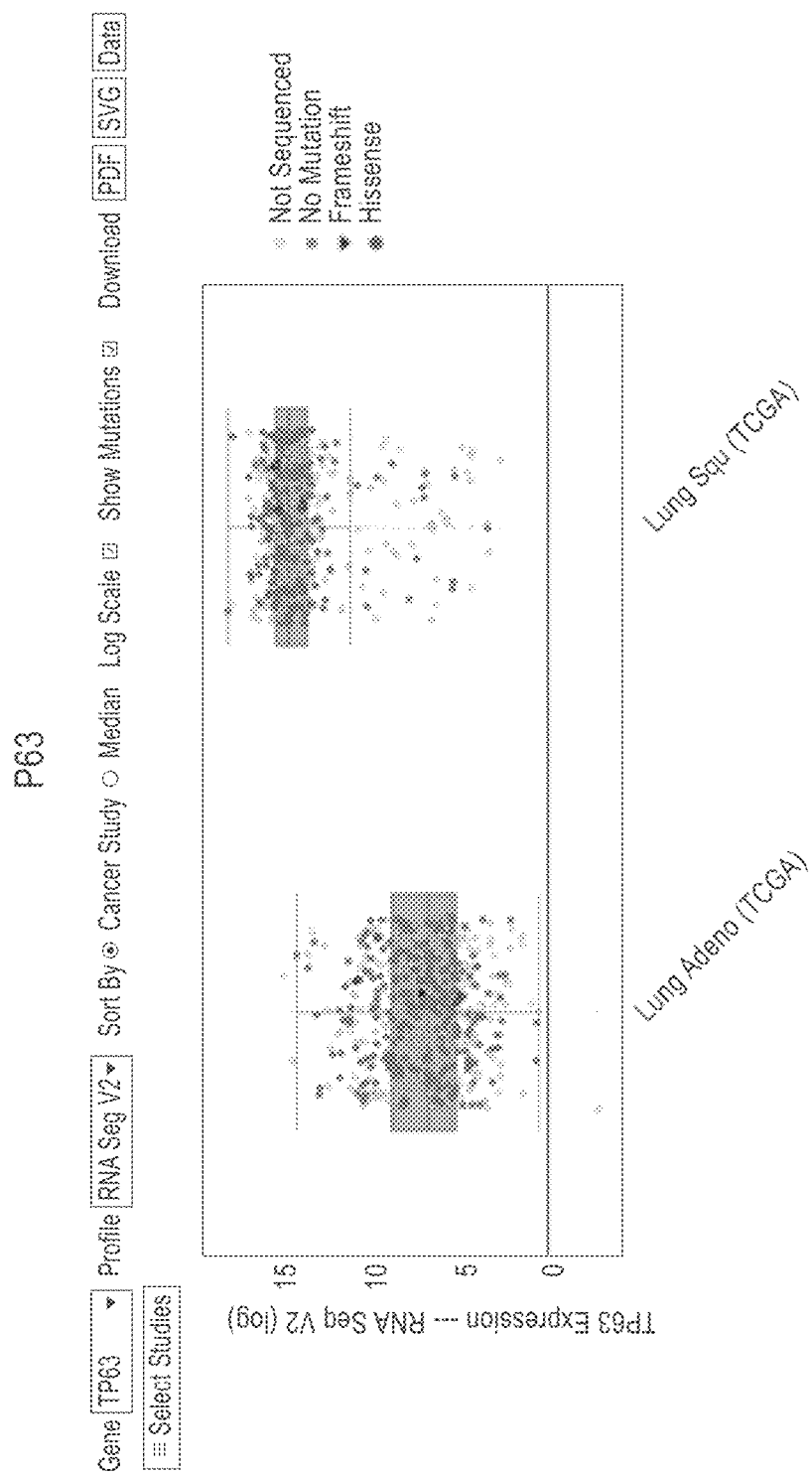

FIG. 12 shows the TCGA provisional data as of May 21, 2018 for lung SCC and ACA extracted from cBioPortal (Cerami et al., Cancer Discov May 1, 2012 (2) (5) 401-404; Gao et al., Sci Signal. 2013 Apr. 2; 6(269):pl) and graphed to show the expression of the SCL34A2, TTF-1, Napsin-A, CK5 and p63 genes in ACA and SCC. In each plot the ACA results are to the left. The y axis is a measure of RNA expression, as determined by RNAseq. The results show that overall, SLC34A2 expression appears higher in adenocarcinoma relative to squamous cell carcinoma.

While the distinctions made based on RNA expression somewhat overlap the proteins that are evaluated in the clinic by IHC, the RNA based classification based on the commonly used genes has not been validated. A published unbiased attempt to find genes most differentially expressed in lung cancer only returned TTF1/TITF 1 in the list of SCC vs ACA genes (Wilkerson et al, Journal of Molecular Diagnostics, 2013 15:4, 485-497), suggesting that RNA profiling based on the genes used for differentiation by IHC is not the best way to make the distinction of ACA vs SCC.

Example 7: Differentiating ACA from SCC Using NaPi2b Protein Expression

An immunohistochemical assay for MERS67 was established on a Leica BondRx Instrument. The assay was performed on tissue microarrays (TMA), including NSCLC and small cell lung cancer (SCLC) cell line arrays, and a NSCLC human tumor array. Tumors in the NSCLC array had previously been classified based on morphologic features only. All arrays were scored based on the H-score method.

Figure 13:
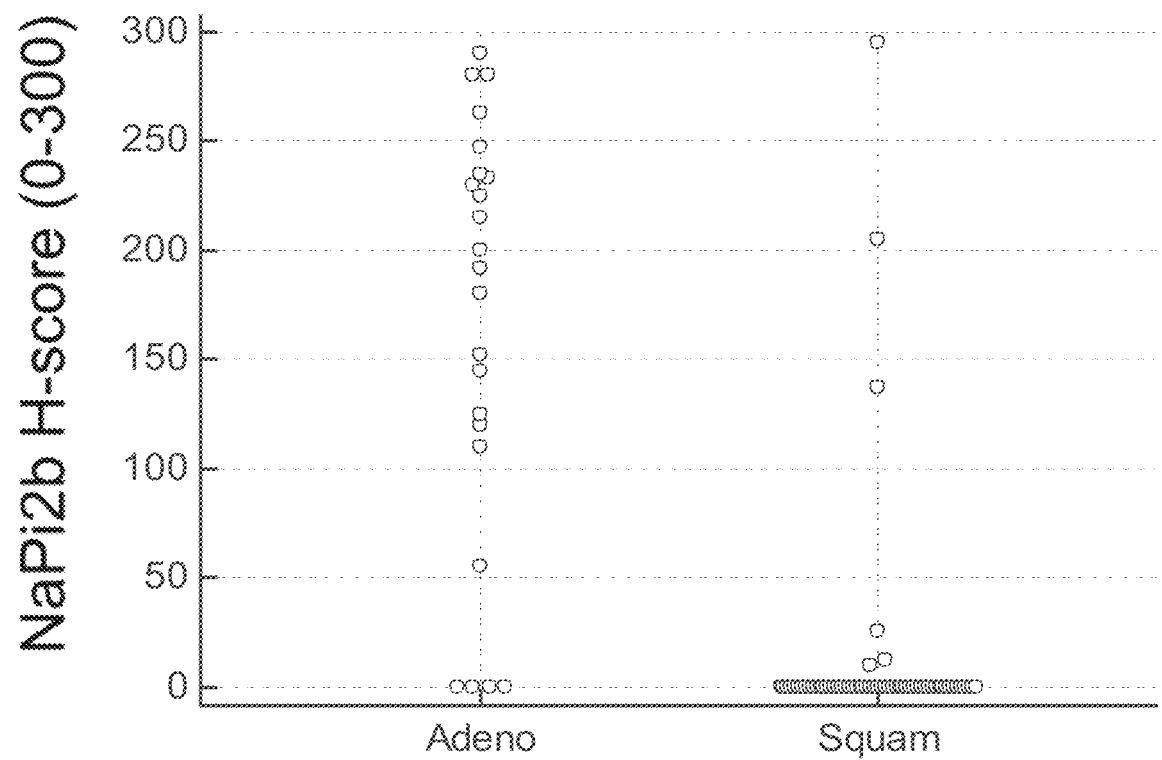
FIG. 13 shows H-scores obtained from NaPi2B IHC evaluation of a tissue microarray of SCC and ACA tumors.

To characterize the primary tumors further, the tumor TMA was stained with TTF-1 and p40, markers of ACA and squamous cell carcinoma (SCC), respectively. Results of this staining were compared to MERS67 staining patterns. H-Scores in the NSCLC cell line TMA ranged from 0-260, and from 0-100 in the small cell lung carcinoma (SCLC) TMA. Within the tissue microarray, 99 individual cases were evaluable. By morphologic classification 63 cases were SCC, and 23 cases were ACA. Using an arbitrary cut point of H=50, there was a statistically significant difference in the number of NaPi2b positive ACA cases (19/23) vs SCC (3/63). FIG. 13 is a box plot of the H scores derived from MERS67 IHC comparing SCC vs ACA, when these tumors were classified by morphology only.

Figure 14:
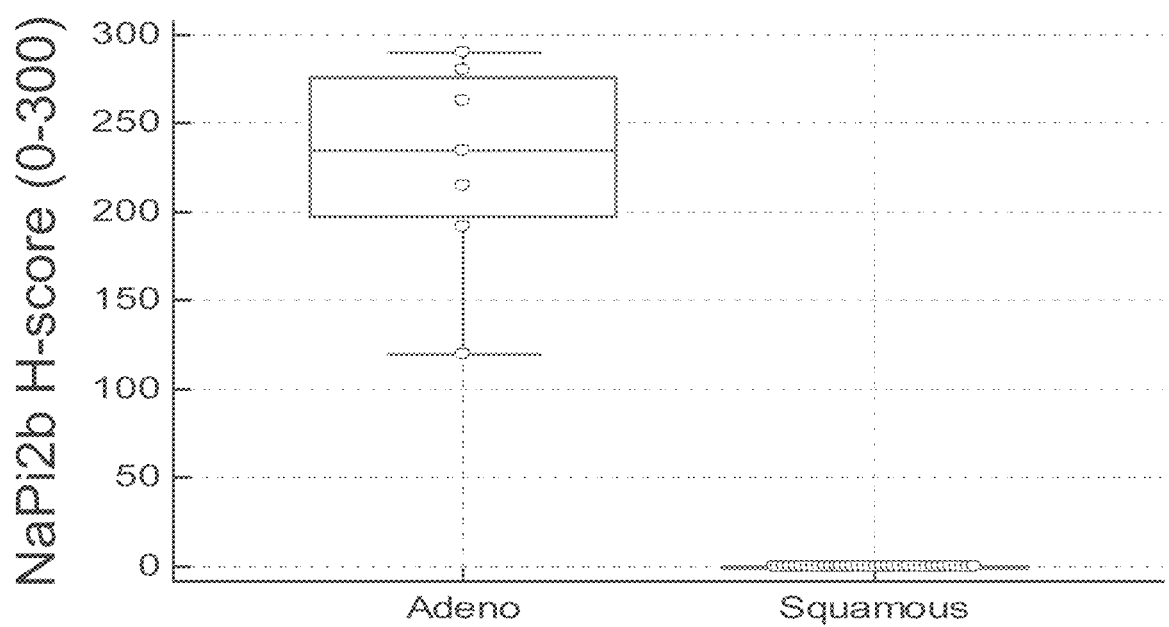
FIG. 14 is a box plot of H-Scores from the same tissue set when the histology subtype was further characterized using p40 and TTF-1 IHC stains.

FIG. 14 shows the NaPi2b staining results based on histology for the NSCLC cohort only in those specimens where classification of ACA vs SCC by histology and TTF-1/p40 IHC results were in agreement. NaPi2b H score as determined by IHC is plotted on the Y-Axis and histology subtype is characterized on the X-axis. Among 43 cases where p40 and TTF-1 were evaluable and were in agreement with morphologic diagnosis, 7/7 cases of ACA were positive for NaPi2b, while 0/36 SCC were positive

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a cancer in a subject with a NaPi2b-targeted antibody drug conjugate comprising:

a. measuring the expression level of NaPi2b in a tumor sample obtained from the subject by contacting the tumor sample with a chimeric anti-NaPi2b antibody, wherein the chimeric anti-NaPi2b antibody comprises a human variable region and a rabbit constant region, wherein the human variable region comprises: a variable heavy chain complementarity determining region 1 (CDRH1) comprising the amino acid sequence GYTFTGYNIH (SEQ ID NO: 3), a variable heavy chain complementarity determining region 2 (CDRH2) comprising the amino acid sequence AIYPGNGDTSYKQKFRG (SEQ ID NO: 4), a variable heavy chain complementarity determining region 3 (CDRH3) comprising the amino acid sequence GETARATFAY (SEQ ID NO: 5), a variable light chain complementarity determining region 1 (CDRL1) comprising the amino acid sequence SASQDIGNFLN (SEQ ID NO: 6), a variable light chain complementarity determining region 2 (CDRL2) comprising the amino acid sequence YTSSLYS (SEQ ID NO: 7), a variable light chain complementarity determining region 3 (CDRL3) comprising the amino acid sequence QQYSKLPLT (SEQ ID NO: 8), and the rabbit constant region comprises a heavy chain constant region comprising the amino acid sequence of SEQ ID NO: 11 and a light chain constant region comprising the amino acid sequence of SEQ ID NO:12;

b. predicting that the subject will be responsive to treatment when the expression level of NaPi2b in the tumor sample is higher than a predetermined quantitative or semi quantitative cut-off score; and c. administering the NaPi2b-targeted antibody drug conjugate to a subject predicted to be responsive;

wherein the NaPi2b-targeted antibody conjugate comprises the NaPi2b-targeted antibody, XMT-1535 comprising a variable heavy chain complementarity determining region 1 (CDRH1) comprising the amino acid sequence GYTFTGYNIH (SEQ ID NO: 3), a variable heavy chain complementarity determining region 2 (CDRH2) comprising the amino acid sequence AIYPGNGDTSYKQKFRG (SEQ ID NO: 4), a variable heavy chain complementarity determining region 3 (CDRH3) comprising the amino acid sequence GETARATFAY (SEQ ID NO: 5), a variable light chain complementarity determining region 1 (CDRL1) comprising the amino acid sequence SASQDIGNFLN (SEQ ID NO: 6), a variable light chain complementarity determining region 2 (CDRL2) comprising the amino acid sequence YTSSLYS (SEQ ID NO: 7), a variable light chain complementarity determining region 3 (CDRL3) comprising the amino acid sequence QQYSKLPLT (SEQ ID NO: 8).

2. The method of claim 1, wherein the cancer is lung cancer, ovarian cancer, breast cancer, colorectal cancer, kidney cancer, thyroid cancer, renal cancer, salivary duct adenocarcinoma, endometrial cancer, cholangiocarcinoma, papillary thyroid cancer or papillary renal cancer.

3. The method of claim 2, wherein the lung cancer is non-small lung carcinoma (NSCLC), wherein the NSCLC is non-squamous NSCLC or adenocarcinoma.

4. The method of claim 2, wherein the ovarian cancer is epithelial ovarian cancer or platinum-refractory ovarian cancer.

5. The method of claim 1, wherein the NaPi2b-targeted antibody drug conjugate is:

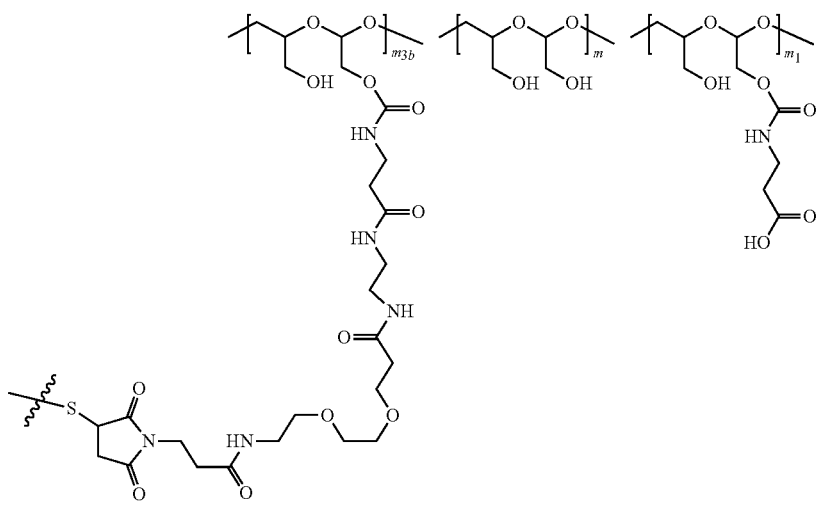

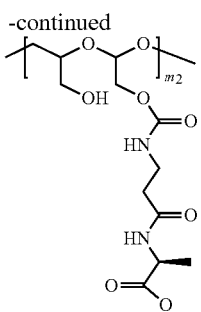
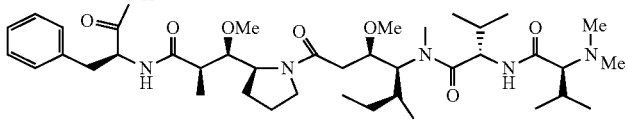
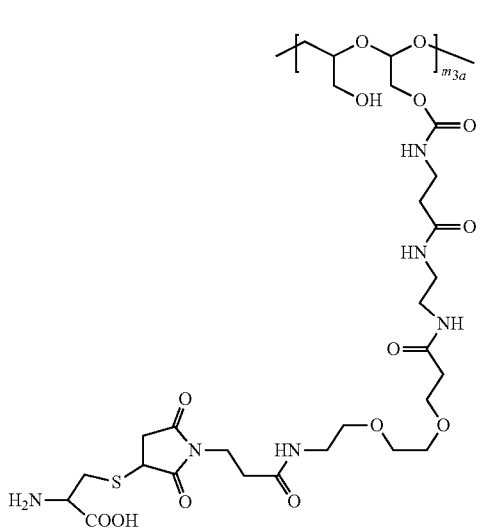

wherein:
 m is an integer from 1 to about 300,
 $m_1$ is an integer from 1 to about 140,
 $m_2$ is an integer from 1 to about 40,
 $m_{3a}$ is an integer from 0 to about 17,
 $m_{3b}$ is an integer from 1 to about 8;
 the sum of $m_{3a}$ and $m_{3b}$ ranges from 1 and about 18; and
 the sum of m, $m_1$, $m_2$, $m_{3a}$, and $m_{3b}$ ranges from 15 to about 300;
 the terminal

denotes the attachment of one or more polymeric scaffolds to the NaPi2b-targeted antibody XMT-1535.

6. The method of claim 1, wherein the antibody comprises the variable heavy chain of SEQ ID NO: 1 and the variable light chain of SEQ ID NO: 2.

7. The method of claim 5, wherein the NaPi2b-targeted antibody, XMT-1535, comprises a variable heavy chain region comprising the amino acid sequence of SEQ ID NO: 1 and a variable light chain region comprising the amino acid sequence of SEQ ID NO: 2.

8. The method of claim 1, wherein the predetermined quantitative or semi quantitative cut-off score is determined by the H-score method, light microscopy or image analysis.

* * * * *

SEQUENCE LISTING

```
<160> NUMBER OF SEQ ID NOS: 18

<210> SEQ ID NO 1
<211> LENGTH: 120
<212> TYPE: PRT
<213> ORGANISM: Artificial Sequence
<220> FEATURE:
<223> OTHER INFORMATION: Synthetic sequence

<400> SEQUENCE: 1

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Gly Tyr
            20                  25                  30

Asn Ile His Trp Val Lys Gln Ala Pro Gly Gln Gly Leu Glu Trp Ile
        35                  40                  45

Gly Ala Ile Tyr Pro Gly Asn Gly Asp Thr Ser Tyr Lys Gln Lys Phe
    50                  55                  60

Arg Gly Arg Ala Thr Leu Thr Ala Asp Thr Ser Thr Ser Thr Val Tyr
65                  70                  75                  80

Met Glu Leu Ser Ser Leu Arg Ser Glu Asp Ser Ala Val Tyr Tyr Cys
                85                  90                  95

Ala Arg Gly Glu Thr Ala Arg Ala Thr Phe Ala Tyr Trp Gly Gln Gly
            100                 105                 110
```

```
Thr Leu Val Thr Val Ser Ser Gly
        115                 120

<210> SEQ ID NO 2
<211> LENGTH: 108
<212> TYPE: PRT
<213> ORGANISM: Artificial Sequence
<220> FEATURE:
<223> OTHER INFORMATION: Synthetic sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Gly Asn Phe
            20                  25                  30

Leu Asn Trp Tyr Gln Gln Lys Pro Gly Lys Thr Val Lys Val Leu Ile
        35                  40                  45

Tyr Tyr Thr Ser Ser Leu Tyr Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Leu Leu Pro Leu
                85                  90                  95

Thr Phe Gly Gln Gly Thr Lys Leu Glu Leu Lys Arg
            100                 105

<210> SEQ ID NO 3
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 3

Gly Tyr Thr Phe Thr Gly Tyr Asn Ile His
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 4

Ala Ile Tyr Pro Gly Asn Gly Asp Thr Ser Tyr Lys Gln Lys Phe Arg
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 5

Gly Glu Thr Ala Arg Ala Thr Phe Ala Tyr
1               5                   10

<210> SEQ ID NO 6
<211> LENGTH: 11
<212> TYPE: PRT
```

```
<213> ORGANISM: Artificial Sequence
<220> FEATURE:
<223> OTHER INFORMATION: Synthetic Sequence

<400> SEQUENCE: 6

Ser Ala Ser Gln Asp Ile Gly Asn Phe Leu Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 7

Tyr Thr Ser Ser Leu Tyr Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 8

Gln Gln Tyr Ser Lys Leu Pro Leu Thr
1               5

<210> SEQ ID NO 9
<211> LENGTH: 357
<212> TYPE: DNA
<213> ORGANISM: Artificial Sequence
<220> FEATURE:
<223> OTHER INFORMATION: Synthetic Sequence

<400> SEQUENCE: 9
caagttcagc tggttcagtc tggcgccgag gttgtgaaac ctggcgcctc tgtgaagatg      60
agctgcaagg ccagcggcta caccttcacc ggctacaaca tccactgggt caagcaggcc     120
cctggacagg gactcgaatg gatcggagcc atctatcccg gcaacggcga caccagctac     180
aagcagaagt tccggggcag agccacactg accgccgata caagcaccag caccgtgtac     240
atggaactga gcagcctgag aagcgaggac agcgccgtgt actattgcgc cagaggcgaa     300
acagccagag ccaccttgc ctattggggc cagggaaccc tggtcaccgt tagctct        357

<210> SEQ ID NO 10
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 10
gatattcaga tgacacagag ccccagcagc ctgtctgcct ctgtgggaga cagagtgacc      60
atcacctgta gcgccagcca ggatatcggc aacttcctga ctggtatca gcagaaaccc     120 ggcaagaccg tgaaggtgct gatctactac acctccagcc tgtacagcgg cgtgcccagc     180 agatttctg gcagcggctc tggcaccgac tacaccctga ccatatctag cctgcagcct     240
gaggacttcg ccacctacta ctgccagcag tacagcaagc tgcccctgac atttggccag     300
ggcaccaagc tggaactgaa g                                                321
```

<210> SEQ ID NO 11
<211> LENGTH: 323
<212> TYPE: PRT
<213> ORGANISM: Oryctolagus cuniculus

<400> SEQUENCE: 11

| Gly | Gln | Pro | Lys | Ala | Pro | Ser | Val | Phe | Pro | Leu | Ala | Pro | Cys | Cys | Gly |
|---|---|---|---|---|---|---|---|---|---|---|---|---|---|---|---|
| 1 | | | | 5 | | | | | 10 | | | | | 15 | |

| Asp | Thr | Pro | Ser | Ser | Thr | Val | Thr | Leu | Gly | Cys | Leu | Val | Lys | Gly | Tyr |
|---|---|---|---|---|---|---|---|---|---|---|---|---|---|---|---|
| | | | 20 | | | | 25 | | | | | 30 | | | |

| Leu | Pro | Glu | Pro | Val | Thr | Val | Thr | Trp | Asn | Ser | Gly | Thr | Leu | Thr | Asn |
|---|---|---|---|---|---|---|---|---|---|---|---|---|---|---|---|
| | | | 35 | | | | 40 | | | | | 45 | | | |

| Gly | Val | Arg | Thr | Phe | Pro | Ser | Val | Arg | Gln | Ser | Ser | Gly | Leu | Tyr | Ser |
|---|---|---|---|---|---|---|---|---|---|---|---|---|---|---|---|
| | 50 | | | | | 55 | | | | | 60 | | | | |

| Leu | Ser | Ser | Val | Val | Ser | Val | Thr | Ser | Ser | Gln | Pro | Val | Thr | Cys |
|---|---|---|---|---|---|---|---|---|---|---|---|---|---|---|
| 65 | | | | | 70 | | | | | 75 | | | | 80 |

| Asn | Val | Ala | His | Pro | Ala | Thr | Asn | Thr | Lys | Val | Asp | Lys | Thr | Val | Ala |
|---|---|---|---|---|---|---|---|---|---|---|---|---|---|---|---|
| | | | | 85 | | | | 90 | | | | | 95 | | |

| Pro | Ser | Thr | Cys | Ser | Lys | Pro | Thr | Cys | Pro | Pro | Glu | Leu | Leu | Gly |
|---|---|---|---|---|---|---|---|---|---|---|---|---|---|---|
| | | | 100 | | | | | 105 | | | | | 110 | |

| Gly | Pro | Ser | Val | Phe | Ile | Phe | Pro | Lys | Pro | Lys | Asp | Thr | Leu | Met |
|---|---|---|---|---|---|---|---|---|---|---|---|---|---|---|
| | | | | 115 | | | | 120 | | | | | 125 | |

| Ile | Ser | Arg | Thr | Pro | Glu | Val | Thr | Cys | Val | Val | Asp | Val | Ser | Glu |
|---|---|---|---|---|---|---|---|---|---|---|---|---|---|---|
| | 130 | | | | | 135 | | | | | 140 | | | |

| Asp | Asp | Pro | Glu | Val | Gln | Phe | Thr | Trp | Tyr | Ile | Asn | Asn | Glu | Gln | Val |
|---|---|---|---|---|---|---|---|---|---|---|---|---|---|---|---|
| 145 | | | | | 150 | | | | | 155 | | | | | 160 |

| Arg | Thr | Ala | Arg | Pro | Pro | Leu | Arg | Glu | Gln | Gln | Phe | Asn | Ser | Thr | Ile |
|---|---|---|---|---|---|---|---|---|---|---|---|---|---|---|---|
| | | | | 165 | | | | | 170 | | | | | 175 | |

| Arg | Val | Val | Ser | Thr | Leu | Pro | Ile | Ala | His | Glu | Asp | Trp | Leu | Arg | Gly |
|---|---|---|---|---|---|---|---|---|---|---|---|---|---|---|---|
| | | | 180 | | | | | 185 | | | | | 190 | | |

| Lys | Glu | Phe | Lys | Cys | Lys | Val | His | Asn | Lys | Ala | Leu | Pro | Ala | Pro | Ile |
|---|---|---|---|---|---|---|---|---|---|---|---|---|---|---|---|
| | | | 195 | | | | | 200 | | | | | 205 | | |

| Glu | Lys | Thr | Ile | Ser | Lys | Ala | Arg | Gly | Gln | Pro | Leu | Glu | Pro | Lys | Val |
|---|---|---|---|---|---|---|---|---|---|---|---|---|---|---|---|
| | 210 | | | | | 215 | | | | | 220 | | | | |

| Tyr | Thr | Met | Gly | Pro | Pro | Arg | Glu | Glu | Leu | Ser | Ser | Arg | Ser | Val | Ser |
|---|---|---|---|---|---|---|---|---|---|---|---|---|---|---|---|
| 225 | | | | | 230 | | | | | 235 | | | | | 240 |

| Leu | Thr | Cys | Met | Ile | Asn | Gly | Phe | Tyr | Pro | Ser | Asp | Ile | Ser | Val | Glu |
|---|---|---|---|---|---|---|---|---|---|---|---|---|---|---|---|
| | | | | 245 | | | | | 250 | | | | | 255 | |

| Trp | Glu | Lys | Asn | Gly | Lys | Ala | Glu | Asp | Asn | Tyr | Lys | Thr | Thr | Pro | Ala |
|---|---|---|---|---|---|---|---|---|---|---|---|---|---|---|---|
| | | | 260 | | | | | 265 | | | | | 270 | | |

| Val | Leu | Asp | Ser | Asp | Gly | Ser | Tyr | Phe | Leu | Tyr | Ser | Lys | Leu | Ser | Val |
|---|---|---|---|---|---|---|---|---|---|---|---|---|---|---|---|
| | | 275 | | | | | 280 | | | | | 285 | | | |

| Pro | Thr | Ser | Glu | Trp | Gln | Arg | Gly | Asp | Val | Phe | Thr | Cys | Ser | Val | Met |
|---|---|---|---|---|---|---|---|---|---|---|---|---|---|---|---|
| | 290 | | | | | 295 | | | | | 300 | | | | |

| His | Glu | Ala | Leu | His | Asn | His | Tyr | Thr | Gln | Lys | Ser | Ile | Ser | Arg | Ser |
|---|---|---|---|---|---|---|---|---|---|---|---|---|---|---|---|
| 305 | | | | | 310 | | | | | 315 | | | | | 320 |

Pro Gly Lys

<210> SEQ ID NO 12
<211> LENGTH: 104
<212> TYPE: PRT
<213> ORGANISM: Oryctolagus cuniculus

<400> SEQUENCE: 12

Arg Asp Pro Val Ala Pro Thr Val Leu Ile Phe Pro Pro Ala Ala Asp

```
            1               5                  10                 15
          Gln Val Ala Thr Gly Thr Val Thr Ile Val Cys Val Ala Asn Lys Tyr
                          20                  25                  30

Phe Pro Asp Val Thr Val Thr Trp Glu Val Asp Gly Thr Thr Gln Thr
                          35                  40                  45

Thr Gly Ile Glu Asn Ser Lys Thr Pro Gln Asn Ser Ala Asp Cys Thr
                  50                  55                  60

Tyr Asn Leu Ser Ser Thr Leu Thr Leu Thr Ser Thr Gln Tyr Asn Ser
          65                  70                  75                  80

His Lys Glu Tyr Thr Cys Lys Val Thr Gln Gly Thr Thr Ser Val Val
                          85                  90                  95

Gln Ser Phe Asn Arg Gly Asp Cys
                          100
```

<210> SEQ ID NO 13
<211> LENGTH: 969
<212> TYPE: DNA
<213> ORGANISM: Oryctolagus cuniculus

<400> SEQUENCE: 13

```
ggacagccta aggctcccag cgtgttccct ctggctcctt gctgtggcga tacccctagc      60
agcacagtga cactgggctg tctggtcaag ggctacctgc ctgaacctgt gaccgtgacc     120
tggaatagcg gcaccctgac caacggcgtg cggacatttc ctagcgtcag acagagcagc     180
ggcctgtact ctctgagcag cgtggtgtct gtgaccagca gctctcagcc tgtgacctgc     240
aatgtggccc atcctgccac caacaccaag gtggacaaaa ccgtggctcc ctccacctgt     300
agcaagccca catgtcctcc accagagctg ctcggaggcc cctccgtgtt tatcttccca     360
cctaagccta aggacaccct gatgatcagc agaacccctg aagtgacctg cgtggtggtg     420
gacgtgtccg aggatgatcc tgaggtgcag ttcacctggt acatcaacaa cgagcaagtg     480
cggaccgcca gacctcctct gagagagcag cagttcaaca gcaccatcag agtggtgtct     540
accctgccta tcgctcacga ggattggctg cggggcaaag agttcaagtg caaggtgcac     600
aacaaggccc tgcctgctcc tatcgagaaa accatctcca aggccagagg ccagccactg     660
gaacccaagg tgtacacaat gggccctcca agagaggaac tgtccagcag atccgtgtct     720
ctgacctgca tgatcaacgg cttctacccc agcgacatca gcgtggaatg ggagaagaat     780
ggcaaggccg aggacaacta caagacaacc cctgccgtgc tggatagcga cggcagctac     840
ttcctgtaca gcaagctgag cgtgcccacc tctgaatggc aacggggaga tgtgtttacc     900
tgcagcgtga tgcacgaggc cctgcacaac cactacaccc agaagtccat cagcaggtcc     960
ccaggcaaa                                                             969
```

<210> SEQ ID NO 14
<211> LENGTH: 312
<212> TYPE: DNA
<213> ORGANISM: Oryctolagus cuniculus

<400> SEQUENCE: 14

```
agggatcctg tggctcccac cgtgctgatt tttccaccag ccgctgatca ggtggccact      60
ggcacagtga caatcgtgtg cgtggccaac aagtacttcc ccgacgtgac cgtgacctgg     120
gaagtcgatg gcaccacaca gaccacaggc atcgagaaca gcaagacccc tcagaacagc     180
gccgactgca cctacaacct gagcagcacc ctgacactga ccagcacaca gtacaacagc     240
cacaaagagt acacctgtaa agtcacccag ggcacaacca gcgtggtgca gagcttcaac     300
```
agaggcgatt gc 312

<210> SEQ ID NO 15
<211> LENGTH: 442
<212> TYPE: PRT
<213> ORGANISM: Artificial Sequence
<220> FEATURE:
<223> OTHER INFORMATION: Synthetic sequence

<400> SEQUENCE: 15

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Gly Tyr
            20                  25                  30

Asn Ile His Trp Val Lys Gln Ala Pro Gly Gln Gly Leu Glu Trp Ile
        35                  40                  45

Gly Ala Ile Tyr Pro Gly Asn Gly Asp Thr Ser Tyr Lys Gln Lys Phe
    50                  55                  60

Arg Gly Arg Ala Thr Leu Thr Ala Asp Thr Ser Thr Ser Thr Val Tyr
65                  70                  75                  80

Met Glu Leu Ser Ser Leu Arg Ser Glu Asp Ser Ala Val Tyr Tyr Cys
                85                  90                  95

Ala Arg Gly Glu Thr Ala Arg Ala Thr Phe Ala Tyr Trp Gly Gln Gly
            100                 105                 110

Thr Leu Val Thr Val Ser Ser Gly Gln Pro Lys Ala Pro Ser Val Phe
        115                 120                 125

Pro Leu Ala Pro Cys Cys Gly Asp Thr Pro Ser Ser Thr Val Thr Leu
    130                 135                 140

Gly Cys Leu Val Lys Gly Tyr Leu Pro Glu Pro Val Thr Val Thr Trp
145                 150                 155                 160

Asn Ser Gly Thr Leu Thr Asn Gly Val Arg Thr Phe Pro Ser Val Arg
                165                 170                 175

Gln Ser Ser Gly Leu Tyr Ser Leu Ser Ser Val Val Ser Val Thr Ser
            180                 185                 190

Ser Ser Gln Pro Val Thr Cys Asn Val Ala His Pro Ala Thr Asn Thr
        195                 200                 205

Lys Val Asp Lys Thr Val Ala Pro Ser Thr Cys Ser Lys Pro Thr Cys
    210                 215                 220

Pro Pro Pro Glu Leu Leu Gly Gly Pro Ser Val Phe Ile Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Glu Asp Pro Glu Val Gln Phe Thr Trp
            260                 265                 270

Tyr Ile Asn Asn Glu Gln Val Arg Thr Ala Arg Pro Pro Leu Arg Glu
        275                 280                 285

Gln Gln Phe Asn Ser Thr Ile Arg Val Val Ser Thr Leu Pro Ile Ala
    290                 295                 300

His Glu Asp Trp Leu Arg Gly Lys Glu Phe Lys Cys Lys Val His Asn
305                 310                 315                 320

Lys Ala Leu Pro Ala Pro Ile Glu Lys Thr Ile Ser Lys Ala Arg Gly
                325                 330                 335

Gln Pro Leu Glu Pro Lys Val Tyr Thr Met Gly Pro Pro Arg Glu Glu
            340                 345                 350

Leu Ser Ser Arg Ser Val Ser Leu Thr Cys Met Ile Asn Gly Phe Tyr
            355                 360                 365

Pro Ser Asp Ile Ser Val Glu Trp Glu Lys Asn Gly Lys Ala Glu Asp
370                 375                 380

Asn Tyr Lys Thr Thr Pro Ala Val Leu Asp Ser Asp Gly Ser Tyr Phe
385                 390                 395                 400

Leu Tyr Ser Lys Leu Ser Val Pro Thr Ser Glu Trp Gln Arg Gly Asp
                405                 410                 415

Val Phe Thr Cys Ser Val Met His Glu Ala Leu His Asn His Tyr Thr
            420                 425                 430

Gln Lys Ser Ile Ser Arg Ser Pro Gly Lys
        435                 440

<210> SEQ ID NO 16
<211> LENGTH: 211
<212> TYPE: PRT
<213> ORGANISM: Artificial Sequence
<220> FEATURE:
<223> OTHER INFORMATION: Synthetic Sequence

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Gly Asn Phe
            20                  25                  30

Leu Asn Trp Tyr Gln Gln Lys Pro Gly Lys Thr Val Lys Val Leu Ile
        35                  40                  45

Tyr Tyr Thr Ser Ser Leu Tyr Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Leu
                85                  90                  95

Thr Phe Gly Gln Gly Thr Lys Leu Glu Leu Lys Arg Asp Pro Val Ala
            100                 105                 110

Pro Thr Val Leu Ile Phe Pro Pro Ala Ala Asp Gln Val Ala Thr Gly
        115                 120                 125

Thr Val Thr Ile Val Cys Val Ala Asn Lys Tyr Phe Pro Asp Val Thr
130                 135                 140

Val Thr Trp Glu Val Asp Gly Thr Thr Gln Thr Thr Gly Ile Glu Asn
145                 150                 155                 160

Ser Lys Thr Pro Gln Asn Ser Ala Asp Cys Thr Tyr Asn Leu Ser Ser
                165                 170                 175

Thr Leu Thr Leu Thr Ser Thr Gln Tyr Asn Ser His Lys Glu Tyr Thr
            180                 185                 190

Cys Lys Val Thr Gln Gly Thr Thr Ser Val Val Gln Ser Phe Asn Arg
        195                 200                 205

Gly Asp Cys
    210

<210> SEQ ID NO 17
<211> LENGTH: 1326
<212> TYPE: DNA
<213> ORGANISM: Artificial Sequence
<220> FEATURE:
<223> OTHER INFORMATION: Synthetic Sequence

<400> SEQUENCE: 17

| | |
|---|---|
| caagttcagc tggttcagtc tggcgccgag gttgtgaaac ctggcgcctc tgtgaagatg | 60 |
| agctgcaagg ccagcggcta caccttcacc ggctacaaca tccactgggt caagcaggcc | 120 |
| cctggacagg gactcgaatg gatcggagcc atctatcccg gcaacggcga caccagctac | 180 |
| aagcagaagt tccggggcag agccacactg accgccgata caagcaccag caccgtgtac | 240 |
| atggaactga gcagcctgag aagcgaggac agcgccgtgt actattgcgc cagaggcgaa | 300 |
| acagccagag ccacctttgc ctattggggc cagggaaccc tggtcaccgt tagctctgga | 360 |
| cagcctaagg ctcccagcgt gttccctctg gctccttgct gtggcgatac ccctagcagc | 420 |
| acagtgacac tgggctgtct ggtcaagggc tacctgcctg aacctgtgac cgtgacctgg | 480 |
| aatagcggca ccctgaccaa cggcgtgcgg acatttccta gcgtcagaca gagcagcggc | 540 |
| ctgtactctc tgagcagcgt ggtgtctgtg accagcagct ctcagcctgt gacctgcaat | 600 |
| gtggcccatc ctgccaccaa caccaaggtg gacaaaaccg tggctccctc cacctgtagc | 660 |
| aagcccacat gtcctccacc agagctgctc ggaggcccct ccgtgtttat cttcccacct | 720 |
| aagcctaagg acaccctgat gatcagcaga acccctgaag tgacctgcgt ggtggtggac | 780 |
| gtgtccgagg atgatcctga ggtgcagttc acctggtaca tcaacaacga gcaagtgcgg | 840 |
| accgccagac ctcctctgag agagcagcag ttcaacagca ccatcagagt ggtgtctacc | 900 |
| ctgcctatcg ctcacgagga ttggctgcgg ggcaaagagt tcaagtgcaa ggtgcacaac | 960 |
| aaggccctgc ctgctcctat cgagaaaacc atctccaagg ccagaggcca gccactggaa | 1020 |
| cccaaggtgt acacaatggg ccctccaaga gaggaactgt ccagcagatc cgtgtctctg | 1080 |
| acctgcatga tcaacggctt ctaccccagc gacatcagcg tggaatggga agaatggcaa | 1140 |
| aaggccgagg acaactacaa gacaaccccc gccgtgctgg atagcgacgg cagctacttc | 1200 |
| ctgtacagca agctgagcgt gcccacctct gaatggcaac ggggagatgt gtttacctgc | 1260 |
| agcgtgatgc acgaggccct gcacaaccac tacacccaga gtccatcag caggtcccca | 1320 |
| ggcaaa | 1326 |

<210> SEQ ID NO 18
<211> LENGTH: 633
<212> TYPE: DNA
<213> ORGANISM: Artificial Sequence
<220> FEATURE:
<223> OTHER INFORMATION: Synthetic Sequence

<400> SEQUENCE: 18

| | |
|---|---|
| gatattcaga tgacacagag cccagcagc ctgtctgcct ctgtgggaga cagagtgacc | 60 |
| atcacctgta gcgccagcca ggatatcggc aacttcctga ctggtatca gcagaaaccc | 120 |
| ggcaagaccg tgaaggtgct gatctactac acctccagcc tgtacagcgg cgtgcccagc | 180 |
| agattttctg gcagcggctc tggcaccgac tacaccctga ccatatctag cctgcagcct | 240 |
| gaggacttcg ccacctacta ctgccagcag tacagcaagt gcccctgac atttggccag | 300 |
| ggcaccaagc tggaactgaa gagggatcct gtggctccca ccgtgctgat ttttccacca | 360 |
| gccgctgatc aggtggccac tggcacagtg acaatcgtgt gcgtggccaa caagtacttc | 420 |

```
cccgacgtga ccgtgacctg ggaagtcgat ggcaccacac agaccacagg catcgagaac    480
agcaagaccc ctcagaacag cgccgactgc acctacaacc tgagcagcac cctgacactg    540
accagcacac agtacaacag ccacaaagag tacacctgta aagtcaccca gggcacaacc    600
agcgtggtgc agagcttcaa cagaggcgat tgc                                 633
```